(12) United States Patent
Monnier et al.

(10) Patent No.: US 10,874,712 B2
(45) Date of Patent: Dec. 29, 2020

(54) METHODS, COMPOUNDS AND COMPOSITIONS FOR MODULATING BLOOD BRAIN BARRIER INTEGRITY AND RE-MYELINATION

(71) Applicant: University Health Network, Toronto (CA)

(72) Inventors: Philippe Patrick Monnier, Toronto (CA); Nardos G. Tassew, Toronto (CA); Yuriy Baglaenko, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 16/528,033

(22) Filed: Jul. 31, 2019

(65) Prior Publication Data

US 2020/0016237 A1 Jan. 16, 2020

Related U.S. Application Data

(63) Continuation of application No. 15/762,497, filed as application No. PCT/CA2016/051122 on Sep. 23, 2016, now Pat. No. 10,398,753.

(60) Provisional application No. 62/338,793, filed on May 19, 2016, provisional application No. 62/222,697, filed on Sep. 23, 2015.

(51) Int. Cl.

| | | |
|---|---|---|
| *A61K 38/17* | (2006.01) | |
| *A61K 49/00* | (2006.01) | |
| *C07K 14/47* | (2006.01) | |
| *A61K 39/395* | (2006.01) | |
| *A61P 25/14* | (2006.01) | |
| *A61P 21/00* | (2006.01) | |
| *A61P 25/28* | (2006.01) | |

(52) U.S. Cl.
CPC ........ *A61K 38/1709* (2013.01); *A61K 38/179* (2013.01); *A61K 39/395* (2013.01); *A61K 49/00* (2013.01); *A61P 21/00* (2018.01); *A61P 25/14* (2018.01); *A61P 25/28* (2018.01); *C07K 14/47* (2013.01)

(58) Field of Classification Search
None
See application file for complete search history.

(56) References Cited

U.S. PATENT DOCUMENTS

| 7,981,420 B2 | 7/2011 | Mueller et al. |
| 2015/0139993 A1 | 5/2015 | Lin et al. |

FOREIGN PATENT DOCUMENTS

| WO | WO 2004/003150 A2 * | 1/2004 |
| WO | WO 2008/124768 | 10/2008 |
| WO | WO 2015/039212 | 3/2015 |

OTHER PUBLICATIONS

Bell et al., Structure of the Repulsive Guidance Molecule (RGM)—Neogenin Signaling Hub , Jul. 5, 2013, Science 341(6141): 77-80 (Year: 2013).*
Vielmetter et al., Molecular Characterization of Human Neogenin, a DCC-Related Protein, and the Mapping of Its Gene (NEO1) to Chromosomal Position 15q22.3-q23, 1997, Genomics 41:414-421 (Year: 1997).*
Alvarez et al., "Disruption of central nervous system barriers in multiple sclerosis," *Biochimica et Biophysica Acta*, 2011, 1812:252-264.
Alvarez et al., "Glial Influence on the Blood Brain Barrier," *GLIA*, 2013, 61:1939-1958.
Andriopoulos Jr. et al., "BMP-6 is a key endogenous regulator of hepcidin expression and iron metabolism," *Nat. Genet.*, 2009, 41(4):482-487.
Babitt et al., "Modulation of bone morphogenetic protein signaling in vivo regulates systemic iron balance," *The Journal of Clinical Investigation*, 2007, 117(7):1933-1939.
Becher et al., "Experimental autoimmune encephalitis and inflammation in the absence of interleukin-12," *J. Clin. Invest.*, 2002, 110:493-497.
Bell et al., "Structure of the Repulsive Guidance Molecule (RGM)—Neogenin Signaling Hub." *Science*, 2013, 341(6141):77-80.
Bettelli et al., "Th17: The third member of the effector T cell Trilogy," *Curr Opin Immunol.*, 2007, 19(6):652-657.
Biernacki et al., "Regulation of th1 and th2 Lymphocyte Migration by Human Adult Brain Endothelial Cells," *Journal of Neuropathology and Experimental Neurology*, 60(12):1127-1136.
Bitsch et al., "Acute axonal injury in multiple sclerosis correlation with demyelination and inflammation," *Brain*, 2000, 123:1174-1183.
Chaturvedi & Robinson, "Slit2-Robo signaling in inflammation and kidney injury," *Pediatr. Nephrol.*, 2015, 30:561-566.
Chaturvedi et al., "Slit2 Prevents Neutrophil Recruitment and Renal Ischemia-Reperfusion Injury," *J. Am. Soc. Nephrol.*, 2013, 24:1274-1287.
Cole et al., "Neogenin: A multi-functional receptor regulating diverse developmental processes," *The International Journal of Biochemistry & Cell Biology*, 2007, 39:1569-1579.
Conrad et al., "Neogenin-RGMa Signaling at the Growth Cone is Bone Morphogenetic Protein-independent and Involves RhoA, ROCK and PKC," *The Journal of Biological Chemistry*, 2007, 282(22):16423-16433.
Core et al., "Hemojuvelin and bone morphogenetic protein (BMP) signaling in iron homeostasis," *Frontiers in Pharmacology*, 2014, 5:104.

(Continued)

*Primary Examiner* — John D Ulm
(74) *Attorney, Agent, or Firm* — Norton Rose Fulbright US LLP

(57) ABSTRACT

Disclosed herein are methods and compositions for increasing and decreasing the permeability of the blood brain barrier for the treatment of diseases and conditions and to facilitate the delivery of agents to the brain, as well as methods and compositions for promoting re-myelination and preventing de-myelination. Compositions include RGMa, soluble RGMa, and functional fragments and variants thereof, RGMc, soluble RGMc, and functional fragments and variants thereof, and Neogenin peptides including 4Ig.

19 Claims, 25 Drawing Sheets

Specification includes a Sequence Listing.

(56) References Cited

OTHER PUBLICATIONS

Cua et al., "Interleukin-23 rather than interleukin-12 is the critical cytokine for autoimmune inflammation of the brain," *Nature*, 2003, 421:744-748.

Demicheva et al., "Targeting Repulsive Guidance Molecule A to Promote Regeneration and Neuroprotection in Multiple Sclerosis," *Cell Reports*, 2015, 10:1887-1898.

Engelhardt & Ransohoff, "The ins and outs of T-lymphocyte trafficking to the CNS: anatomical sites and molecular mechanisms," *Trends in Immunology*, 2005, 26(9):485-495.

Enns et al., "Neogenin Interacts with Matriptase-2 to Facilitate Hemojuvelin Cleavage," *Journal of Biological Chemistry*, 2012, 287(42):35104-35117.

Extended European Search Report for European Patent Application No. 16847698.4 dated Apr. 12, 2019 (11 pages).

Ferguson et al., "Axonal damage in acute multiple sclerosis lesion," *Brain*, 1997, 120:393-399.

Fillatreau et al., "B cells regulate autoimmunity by provision of IL-10," *Nature Immunology*, 2002, 3(10):944-950.

Friese et al., "Mechanisms of neurodegeneration and axonal dysfunction in multiple sclerosis," *Nat. Rev. Neurol.*, 2014, 10:225-238.

Gaitan et al., "Evolution of the Blood-Brain Barrier in Newly Forming Multiple Sclerosis Lesions," *Ann. Neurol.*, 2011, 70:22-29.

Ganz, Tomas, "Molecular Control of Iron Transport," *J. Am. Soc. Nephrol.*, 2007, 18:394-400.

Gemmati et al., "Polymorphisms in the genes coding for iron binding and transporting proteins are associated with disability, severity, and early progression in multiple sclerosis" *BMC Medical Genetics*, 2012, 13:70.

Gold et al., "Understanding pathogenesis and therapy of multiple sclerosis via animal models: 70 years of merits and culprits in experimental autoimmune encephalomyelitis research," *Brain*, 2006, 129:1953-1971.

Grant et al., "Iron-Deficient Mice Fail to Develop Autoimmune Encephalomyelitis," *The Journal of Nutrition*, 2003, 133(8):2635-2638.

Guan et al., "Neuronal Repellent Slit2 Inhibits dendritic Cell Migration and the Development of Immune Responses," *The Journal of Immunology*, 2003, 171:6519-6526.

Hata et al., "RGMa inhibition promotes axonal growth and recovery after spinal cord injury," *The Journal of Cell Biology*, 2006, 173(1):47-58.

International Search Report and Written Opinion issued in International Patent Application No. PCT/CA2016/051122, dated Dec. 5, 2016.

Jones et al., "Robo4 stabilizes the vascular network by inhibiting pathologic angiogenesis and endothelial hyperpermeability," *Nat Med.*, 2008, 14(4):448-453.

Jones et al., "Slit2-Robo4 signaling promotes vascular stability by blocking Arf6 activity," *Nat Cell Biol.*, 2009, 11(11):1325-1331.

Kebir et al., "Human $T_H17$ lymphocytes promote blood-brain barrier disruption and central nervous system inflammation," *Nat. Med.*, 2007, 13(10):1173-1175.

Kitayama et al., "Activated Microglia Inhibit Axonal Growth through RGMa," *PLoS One*, 2011, 6(9):e25234.

Koh et al., "Less Mortality by Mre Relapses in Experimental Allergic Encephalomyelitis in CD8$^{-/-}$ Mice," *Science*, 1992, 256:1210-1213.

Konig et al., "The Axonal Guidance Receptor Neogenin Promotes Acute Inflammation," *PLoS One*, 2012, 7(3):e32145.

Kroenke et al., "IL-12- and IL-23-modulated T Cells induce distinct types of EAE based on histology, CNS chemokine profile, and response to cytokine inhibition," *Journal of Experimental Medicine*, 2008, 205(7):1535-1541.

Kubo et al., "Repulsive guidance molecule-a and demyelination implications for multiple sclerosis," *J. Neuroimmune Pharmacol.*, 2012, 7:524-528.

Kuninger et al., "Pro-protein convertases control the maturation and processing of the iron-regulatory protein, RGMc/hemojuvelin," *BMC Biochemistry*, 2008, 9:9.

Kuns-Hashimoto et al., "Selective binding of RGMc/hemojuvelin, a key protein in systemic iron metabolism, to BMP-2 and neogenin," *Am J. Physiol. Cell Physiol.*, 2008, 294:C994-C1003.

Lassmann et al., "Progressive multiple sclerosis: pathology and pathogenesis," *Nat. Rev. Neurol.*, 2012, 8:647-656.

Lee et al., "Neogenin inhibits HJV secretion and regulates BMP-induced hepcidin expression and iron homeostasis," *Blood*, 2010, 115(15):3136-3145.

LeVine et al., "Iron accumulation in multiple sclerosis: an early pathogenic event," *Expert Review of Neurotherapeutics*, 2014, 13(3):247-250.

LeVine et al., "The Role of Iron in the Pathogenesis of Experimental Allergic Encephalomyelitis and Multiple Sclerosis," *Ann. N.Y. Acad. Sci.*, 2004, 1012:252-266.

Liu et al., "Effects of treadmill exercise on the expression of netrin-1 and its receptors in rate brain after cerebral ischemia," *Neuroscience*, 2011, 194:349-358.

Ly et al., "Netrin-1 inhibits leukocyte migration in vitro and in vivo," *PNAS*, 2005, 102(41):14729-14734.

Ma et al., "The BMP co-receptor RGMb promotes while the endogenous BMP antagonist Noggin reduces neurite outgrowth and peripheral nerve regeneration by modulating BMP signaling," *J. Neurosci.*, 2011, 31(5):18391-18400.

Meynard et al., "Lack of the bone morphogenetic protein BMP6 induces massive iron overload," *Nature Genetics*, 2009, 41(4):478-481.

Mirakaj et al., "Repulsive guidance molecule-A (RGM-A) inhibits leukocyte migration nd mitigates inflammation," PNAS, 2011, 108(16):6555-6560.

Montero et al., "Regulation of experimental autoimmune encephalomyelitis by CD4+, CD25+ and CD8+ T cells: analysis using depleting antibodies" *Journal of Autoimmunity*, 2004, 23:1-7.

Mueller et al., "Rho Kinase, a Promising Drug Target for Neurological Disorders," *Nature Reviews*, 2005, 4:387-398.

Muramatsu et al., "RGMa modulates T cell repsonses and is involved in autoimmune encephalomyelitis," *Nature Medicine*, 2011, 17(4):488-495.

Nili et al., "Proteomic Analysis and Molecular Modeling Characterize the Iron-Regulatory Protein, Hemojuvelin/Repulsive Guidance Molecule c," *Biochem J.*, 2013, 452(1):87-95.

Nohra et al., "RGMA and IL21R show association with experimental inflammation and multiple sclerosis," *Genes and Immunity*, 2010, 11:279-293.

Noseworthy et al., "Multiple Sclerosis," *The New England Journal of Medicine*, 2000, 343(13):938-952.

O'Leary et al., "RGMa Regulates Cortical Interneuron Migration and Differentiation," *PLoS One*, 2013, 8(11):e81711.

Park et al., "A distinct lineage of CD4 T cells regulates tissue inflammation by producing interleukin 17," *Nat. Immunol.*, 2005, 6(11):113-1141.

Paterson, Philip, "Transfer of Allergic Encephalomyelitis in Rates by Means of Lymph Node Cells," *The Journal of Experimental Medicine*, 1960, 111:119-136.

Pawate et al., "Analysis of T2 Intensity by Magnetic Resonance Imaging of Deep Gray Matter Nuclei in Multiple Sclerosis Patients: Effect of Immunomodulatory Therapies," *J. Neuroimaging*, 2012, 12:137-144.

Persidsky et al., "Rho-mediated regulation of tight junctions during monocyte migration across the blood-brain barrier in HIV-1 encephalitis (HIVE)," *Blood*, 2006, 107(12):4770-4780.

Rajagopalan et al., "Neogenin mediates the action of repulsive guidance molecule," *Nature Cell Biology*, 2004, 6(8):756-762.

Rangachari & Kauchroo, "Using EAE to better understand principles of immune function and autoimmune pathology," *J. Autoimmun.*, 2013, 45:31-39.

Satoh et al. "Accumulation of a repulsive axonal guidance molecule RGMa in amyloid plaques: a possible hallmark of regenerative failure in Alzheimer's disease brains: RGMA accumulation in amyloid plaques", *Neuropathology and Applied Neurobiology*, vol. 39, No. 2, Jan. 25, 2013.

(56) References Cited

OTHER PUBLICATIONS

Schwab et al., "Spinal cord injury-induced lesional expression of the repulsive guidance molecule (RGM)" *Eur. J. Neurosci.*, 2005, 21:1569-1576.

Severyn et al., "Molecular biology, genetics and biochemistry of the repulsive guidance molecule family," *Biochem J.*, 2014, 422(3):393-403.

Stankiewicz & Brass, "Role of iron in neurotoxicity: a cause for concern in the elderly?" *Current opinion in Clinical Nutrition and Metabolic Care*, 2009, 12:22-29.

Stankiewicz et al., "Iron and multiple sclerosis," *Neurobiology of Aging*, 2014, 35:S51-S58.

Stromnes et al., "Differential regulation of central nervous system autoimmunity by $T_H1$ and $T_H17$ cells," *Nat. Med.*, 2008, 14(3):337.

Suzuki et al., "Semaphorin 7A initiates T-cell-mediated inflammatory responses through $\alpha 1\beta 1$ integrin," *Nature*, 2007, 446:680-684.

Tassew et al., "Modifying Lipid Rafts Promotes Regeneration and Functional Recovery," *Cell Reports*, 2014, 8:1146-1159.

Tassew et al., "SKI-1 and Furin Generate Multiple RGMa Fragments that Regulate Axonal Growth," *Developmental Cell*, 2012, 22:391-402.

Tole et al., "The axonal repellent, Slit2, inhibits directional migration of circulating neutrophils," *J. Leukoc. Biol.*, 2009, 86:1403-1415.

Traugott & Lebon, "Multiple Sclerosis: Involvement of Interferons in lesion Pathogenesis," *Ann Neurol.*, 1988, 24:243-251.

Viglietta et al., "Loss of Functional Suppression by CD4+CD25+ Regulatory T Cells in Patients with Multiple Sclerosis," *The Journal of Experimental Medicine*, 2004, 199(7):971-979.

Vigouroux, Robin J "Identifying the role of RGMc in an animal model of Multiple Sclerosis" Jan. 1, 2015, pp. iv-104, Retrieved from the Internet: https://tinyurl.com/yyatznwx. Note: Although this thesis was finished in 2015, it was embargoed from publication and not public until Jun. 14, 2017, therefore, its publication date is Jun. 14, 2017.

Weigel et al., "Iron Chelation and multiple sclerosis," *ASN Neuro*, 2014, 6(1):e00136.

Wen et al., "Overexpression of netrin-1 increases the expression of tight junction-associated proteins, claudin-5, occluding, and ZO-1, following traumatic brain injury in rats," *Experimental and Therapeutic Medicine*, 2014, 8:881-886.

Wilson & Key, "Neogenin interacts with RGMa and Netrin-1 to guide axons within the embryonic vertebrate forebrain," *Developmental Biology*, 2006, 296:485-498.

Wong et al., "Signal Transduction in Neuronal Migration: Roles of FTPase Activating Proteins and the Small GTPase Cdc42 in the Slit-Robo Pathway," *Cell*, 2001, 107:209-221.

Wu et al., "The neuronal repellent Slit inhibits leukocyte chemotaxis induced by chemotactic factors," *Nature*, 2001, 410(6831):947-952.

Xu et al., "Structure of Netrin-1 Bound to two Receptors Provide Insight into its Axon Guidance Mechanism," *Science*, 2014, 344(6189):1275-1279.

Yang et al., "Neogenin interacts with hemojuvelin through its two membrane-proximal fibronectin type III domains," *Biochemistry*, 2008, 47(14):4237.

Zhao et al., "Slit2-Robo4 pathway modulates LPS-induced endothelial inflammation and its expression is dysregulated during endotoxemia," *J. Immunol.*, 2014, 192(1):385-393.

\* cited by examiner

A

B

A

B

SEQUENCE LISTING

```
<160> NUMBER OF SEQ ID NOS: 6

<210> SEQ ID NO 1
<211> LENGTH: 359
<212> TYPE: PRT
<213> ORGANISM: Homo sapiens

<400> SEQUENCE: 1

Cys Lys Ile Leu Arg Cys Asn Ala Glu Tyr Val Ser Ser Thr Leu Ser
1               5                   10                  15

Leu Arg Gly Gly Gly Ser Ser Gly Ala Leu Arg Gly Gly Gly Gly Gly
            20                  25                  30

Gly Arg Gly Gly Gly Val Gly Ser Gly Gly Leu Cys Arg Ala Leu Arg
        35                  40                  45

Ser Tyr Ala Leu Cys Thr Arg Arg Thr Ala Arg Thr Cys Arg Gly Asp
    50                  55                  60

Leu Ala Phe His Ser Ala Val His Gly Ile Glu Asp Leu Met Ile Gln
65                  70                  75                  80

His Asn Cys Ser Arg Gln Gly Pro Thr Ala Pro Pro Pro Arg Gly
                85                  90                  95

Pro Ala Leu Pro Gly Ala Gly Ser Gly Leu Pro Ala Pro Asp Pro Cys
            100                 105                 110

Asp Tyr Glu Gly Arg Phe Ser Arg Leu His Gly Arg Pro Pro Gly Phe
        115                 120                 125

Leu His Cys Ala Ser Phe Gly Asp Pro His Val Arg Ser Phe His His
    130                 135                 140

His Phe His Thr Cys Arg Val Gln Gly Ala Trp Pro Leu Leu Asp Asn
145                 150                 155                 160

Asp Phe Leu Phe Val Gln Ala Thr Ser Ser Pro Met Ala Leu Gly Ala
                165                 170                 175

Asn Ala Thr Ala Thr Arg Lys Leu Thr Ile Ile Phe Lys Asn Met Gln
            180                 185                 190

Glu Cys Ile Asp Gln Lys Val Tyr Gln Ala Glu Val Asp Asn Leu Pro
        195                 200                 205
```

```
Val Ala Phe Glu Asp Gly Ser Ile Asn Gly Gly Asp Arg Pro Gly Gly
    210                 215                 220
Ser Ser Leu Ser Ile Gln Thr Ala Asn Pro Gly Asn His Val Glu Ile
225                 230                 235                 240
Gln Ala Ala Tyr Ile Gly Thr Thr Ile Ile Arg Gln Thr Ala Gly
                245                 250                 255
Gln Leu Ser Phe Ser Ile Lys Val Ala Glu Asp Val Ala Met Ala Phe
                260                 265                 270
Ser Ala Glu Gln Asp Leu Gln Leu Cys Val Gly Cys Pro Pro Ser
            275                 280                 285
Gln Arg Leu Ser Arg Ser Glu Arg Asn Arg Gly Ala Ile Thr Ile
    290                 295                 300
Asp Thr Ala Arg Arg Leu Cys Lys Glu Gly Leu Pro Val Glu Asp Ala
305                 310                 315                 320
Tyr Phe His Ser Cys Val Phe Asp Val Leu Ile Ser Gly Asp Pro Asn
                325                 330                 335
Phe Thr Val Ala Ala Gln Ala Ala Leu Glu Asp Ala Arg Ala Phe Leu
            340                 345                 350
Pro Asp Leu Glu Lys Leu His
        355
```

<210> SEQ ID NO 2
<211> LENGTH: 1077
<212> TYPE: DNA
<213> ORGANISM: Homo sapiens

<400> SEQUENCE: 2

```
tgcaagatcc tccgctgcaa tgctgagtac gtatcgtcca ctctgagcct tagaggtggg     60
ggttcatcag gagcacttcg aggaggagga ggaggaggcc ggggtggagg ggtgggctct    120
ggcggcctct gtcgagccct ccgctcctat gcgctctgca ctcggcgcac cgcccgcacc    180
tgccgcgggg acctcgcctt ccattcggcg gtacatggca tcgaagacct gatgatccag    240
cacaactgct cccgccaggg ccctacagcc cctcccccgc cccggggccc cgcccttcca    300
ggcgcgggct ccggcctccc tgccccggac ccttgtgact atgaaggccg ttttccccgg    360
ctgcatggtc gtccccgggg gttcttgcat gcgcttcct tcggggaccc ccatgtgcgc    420
agcttccacc atcactttca cacatgccgt gtccaaggag cttggcctct actgataat    480
gacttcctct ttgtccaagc caccagctcc ccatggcgt gggggccaa cgctaccgcc    540
accggaagc tcaccatcat atttaagaac atgcaggaat gcattgatca gaaggtgtat    600
caggctgagg tggataatct tcctgtagcc tttgaagatg gttctatcaa tggaggtgac    660
cgacctgggg gatccagttt gtcgattcaa actgctaacc ctgggaacca tgtggagatc    720
caagctgcct acattggcac aactataatc attcggcaga cagctgggca gctctccttc    780
tccatcaagg tagcagagga tgtggccatg gccttctcag ctgaacagga cctgcagctc    840
tgtgttgggg ggtgccctcc aagtcagcga ctctctcgat cagagcgcaa tcgtcgggga    900
gctataacca ttgatactgc cagacggctg tgcaaggaag gcttccagt ggaagatgct    960
tacttccatt cctgtgtctt tgatgtttta atttctggtg atcccaactt taccgtggca   1020
gctcaggcag cactggagga tgcccgagcc ttcctgccag acttagagaa gctgcat      1077
```

<210> SEQ ID NO 3
<211> LENGTH: 357
<212> TYPE: PRT
<213> ORGANISM: Mus musculus

<400> SEQUENCE: 3

```
Cys Lys Ile Leu Arg Cys Asn Ala Glu Tyr Val Ser Ser Thr Leu Ser
 1               5                  10                  15
Leu Arg Gly Gly Gly Ser Pro Asp Thr Pro Arg Gly Gly Arg Gly
             20                  25                  30
Gly Leu Ala Ser Gly Gly Leu Cys Arg Ala Leu Arg Ser Tyr Ala Leu
             35                  40                  45
Cys Thr Arg Arg Thr Ala Arg Thr Cys Arg Gly Asp Leu Ala Phe His
 50                  55                  60
Ser Ala Val His Gly Ile Glu Asp Leu Met Ile Gln His Asn Cys Ser
 65                  70                  75                  80
Arg Gln Gly Pro Thr Ala Pro Pro Ala Arg Gly Pro Ala Leu Pro
                 85                  90                  95
Gly Ala Gly Pro Ala Pro Leu Thr Pro Asp Pro Cys Asp Tyr Glu Ala
                100                 105                 110
Arg Phe Ser Arg Leu His Gly Arg Ala Pro Gly Phe Leu His Cys Ala
            115                 120                 125
Ser Phe Gly Asp Pro His Val Arg Ser Phe His Asn Gln Phe His Thr
130                 135                 140
Cys Arg Val Gln Gly Ala Trp Pro Leu Leu Asp Asn Asp Phe Leu Phe
145                 150                 155                 160
Val Gln Ala Thr Ser Ser Pro Val Ser Ser Gly Ala Asn Ala Thr Thr
                165                 170                 175
Ile Arg Lys Ile Thr Ile Ile Phe Lys Asn Met Gln Glu Cys Ile Asp
            180                 185                 190
Gln Lys Val Tyr Gln Ala Glu Val Asp Asn Leu Pro Ala Ala Phe Glu
        195                 200                 205
Asp Gly Ser Ile Asn Gly Gly Asp Arg Pro Gly Gly Ser Ser Leu Ser
    210                 215                 220
Ile Gln Thr Ala Asn Leu Gly Ser His Val Glu Ile Arg Ala Ala Tyr
225                 230                 235                 240
Ile Gly Thr Thr Ile Ile Arg Gln Thr Ala Gly Gln Leu Ser Phe
                245                 250                 255
Ser Ile Arg Val Ala Glu Asp Val Ala Arg Ala Phe Ser Ala Glu Gln
            260                 265                 270
Asp Leu Gln Leu Cys Val Gly Gly Cys Pro Pro Ser Gln Arg Leu Ser
        275                 280                 285
Arg Ser Glu Arg Asn Arg Arg Gly Ala Ile Ala Ile Asp Thr Ala Arg
    290                 295                 300
Arg Leu Cys Lys Glu Gly Leu Pro Val Glu Asp Ala Tyr Phe Gln Ser
305                 310                 315                 320
Cys Val Phe Asp Val Ser Val Ser Gly Asp Pro Asn Phe Thr Val Ala
                325                 330                 335
Ala Gln Thr Ala Leu Asp Asp Ala Arg Ile Phe Leu Thr Asp Leu Glu
            340                 345                 350
Asn Leu His Leu Phe
        355

<210> SEQ ID NO 4
<211> LENGTH: 1071
<212> TYPE: DNA
<213> ORGANISM: Mus musculus
```

-continued

```
<400> SEQUENCE: 4
tgcaagatcc tccgctgcaa tgccgagtat gtctcgtcca ctctgagtct tcggggaggt      60
ggctcaccgg acacgccgcg tggaggcggc cgtggtgggc tggcctcagg tggcttgtgt     120
cgcgccctgc gctcctacgc tctctgcacg cggcgcacgg cccgcacctg ccgcggggac     180
cttgctttcc actctgcggt gcatggcata gaggacctga tgatccagca caactgctca     240
cgccagggtc ccacgccccc gccccgggcc cggggccccg ccctgcccgg ggccgggcca     300
gcgcccctga ccccagatcc ctgtgactat gaggcccggt tttccaggct gcacggtcga     360
gccccgggct tcttgcattg cgcatccttt ggagatcccc atgtgcgcag tttccacaac     420
caatttcaca catgccgtgt ccaaggagct tggcccttgc tagataacga cttcctcttt     480
gtccaggcca ccagctcccc ggtttcgtcg ggagccaacg ctaccaccat ccggaagatc     540
actatcatat ttaaaaacat gcaggaatgc attgaccaga aagtctacca ggctgaggtg     600
gacaatcttc ctgcagcctt tgaagatggt tctatcaatg ggggcgaccg acctggggc      660 tcgagtttgt ccattcaaac tgctaacctt gggagtcacg tggagattcg agctgcctac     720
attggaacaa ctatcatcat tcgacagaca gctgggcagc tctccttctc catcagggta     780
gcagaggatg tggcgcgggc cttctccgca gagcaggacc tacagctgtg tgttggggga     840
tgccctccga gccagcgact ctctcgctca gagcgcaacc gccgtggggc tatagccata     900
gatactgcca gaaggctgtg taaggaaggg cttccggttg aagatgccta cttccaatcc     960
tgcgtctttg atgtttcagt ctccggtgac cccaacttta ctgtggcagc tcagacagct    1020
ctggacgatg cccgaatctt cttgacggat ttagagaact tacatctctt t             1071

<210> SEQ ID NO 5
<211> LENGTH: 47
<212> TYPE: DNA
<213> ORGANISM: Artificial Sequence
<220> FEATURE:
<223> OTHER INFORMATION: Forward Primer

<400> SEQUENCE: 5
cttggtaccc atcatcatca tcatcatcag tgcaagatcc tccgctg                    47

<210> SEQ ID NO 6
<211> LENGTH: 41
<212> TYPE: DNA
<213> ORGANISM: Artificial Sequence
<220> FEATURE:
<223> OTHER INFORMATION: Reverse Primer

<400> SEQUENCE: 6
gcgtctagac actcgagcgt cgagctgccc agctgtctgt c                          41
```

METHODS, COMPOUNDS AND COMPOSITIONS FOR MODULATING BLOOD BRAIN BARRIER INTEGRITY AND RE-MYELINATION

CROSS-REFERENCE TO RELATED APPLICATIONS

This application is a continuation of U.S. Ser. No. 15/762,497 filed Mar. 22, 2018, which is a national phase application under 35 U.S.C. § 371 of International Application No. PCT/CA2016/051122 filed Sep. 23, 2016, which claims the benefit of U.S. Provisional Patent Application Ser. No. 62/222,697, filed Sep. 23, 2015, and of U.S. Provisional Patent Application Ser. No. 62/338,793, filed May 19, 2016, the entire contents of each of which are hereby incorporated by reference in their entireties.

SEQUENCE LISTING

The present application includes as part of its description a sequence listing that includes 6 sequences and which was filed with this application in electronic form and this sequence listing is incorporated into the present application in its entirety.

TECHNICAL FIELD

The present invention relates to methods of modulating blood brain barrier (BBB) integrity, and methods of treating a disease in which BBB disruption are detrimental to a subject, for example, multiple sclerosis, ischemia (e.g. stroke), Alzheimer's disease, Parkinson's disease, epilepsy, and spinal cord injury.

BACKGROUND

Multiple sclerosis (MS) is a debilitating disease and is one of the leading causes of non-traumatic neurological disability among the young population in North America and Europe. The clinical progression of the disease is variable with ~85% of patients at diagnosis exhibiting unpredictable and recurring episodes of neurological deficits that spontaneously subside. Over time, MS patients endure a slow, progressive and irreversible neurological decline, which may be delayed with early therapeutic intervention. The neurodegeneration and ensuing axonal loss in MS patients results in permanent clinical deficits, including limb paralysis, vision loss, spinal cord symptoms, and cognitive deficit. [Noseworthy J H, Lucchinetti C, Rodriguez M, & Weinshenker B G (2000) Multiple sclerosis. *The New England Journal of Medicine* 343(13):938-952] Because of the long duration of disability and high prevalence among young adults, MS is an enormous public health issue with high socio-economic burden and significant impact on the quality of life.

The pathophysiology of MS is thought to have an autoimmune origin with multifocal lesions in the Central Nervous System (CNS) that are characterized by inflammation, demyelination, and axonal injury. This is compounded by the pronounced loss of neuronal connections, which lack the innate capacity to self-repair and an increased susceptibility of adult CNS neurons to apoptotic cell death. It is accepted that irreversible axonal and neuronal loss is a major determinant of the progressive and permanent neurological impairment in MS patients. [Noseworthy J H, Lucchinetti C, Rodriguez M, & Weinshenker B G (2000) Multiple sclerosis. *The New England Journal of Medicine* 343(13):938-952] The heterogeneity in the pathology and clinical progression of MS has led to numerous etiological hypotheses, but none have yet to be confirmed. Furthermore, it remains unknown whether neurodegeneration precedes the autoimmune attack in MS or vice versa.

Of interest, elevated circulating iron levels and deposition of iron in the brains of MS have been reported. [Stankiewicz J M & Brass S D (2009) Role of iron in neurotoxicity: a cause for concern in the elderly? *Current Opinion in Clinical Nutrition and Metabolic Care* 12(1):22-29; LeVine S M, Bilgen M, & Lynch S G (2013) Iron accumulation in multiple sclerosis: an early pathogenic event. *Expert Review of Neurotherapeutics* 13(3):247-250.] Two genes FPN1 (encodes an iron exporter protein) and HEPC (encodes hepcidin, an enzyme that is crucial in iron regulation) were found to increase the incidence of MS by more than 4-fold and 2.5-fold respectively. [Gemmati D, et al. (2012) Polymorphisms in the genes coding for iron binding and transporting proteins are associated with disability, severity, and early progression in multiple sclerosis. *BMC Medical Genetics* 13:70] Furthermore, reducing levels of iron resulted in reduced disease severity. [Grant S M, Wiesinger J A, Beard J L, & Cantorna M T (2003) Iron-deficient mice fail to develop autoimmune encephalomyelitis. *The Journal of Nutrition* 133(8):2635-2638; Stankiewicz J M, Neema M, & Ceccarelli A (2014) Iron and multiple sclerosis. *Neurobiology of Aging* 35S2:S51-S58; Weigel K J, Lynch S G, & Levine S M (2014) Iron chelation and multiple sclerosis. *ASN Neuro* 6(1):e00136; LeVine S M & Chakrabarty A (2004) The role of iron in the pathogenesis of experimental allergic encephalomyelitis and multiple sclerosis. *Annals of the New York Academy of Sciences* 1012:252-266] Notably, MS patients undergoing treatment show decreased levels of iron as compared to patients receiving placebo, thus implying a possible role for iron in mediating disease progression. [Pawate S, Wang L, Song Y, & Sriram S (2012) Analysis of T2 intensity by magnetic resonance imaging of deep gray matter nuclei in multiple sclerosis patients: effect of immunomodulatory therapies. *Journal of Neuroimaging: Official Journal of the American Society of Neuroimaging* 22(2):137-144] The role of iron in MS remains speculative with no clear understanding on whether iron deposition is the result of neurodegeneration or whether it contributes to the development of the disease.

The identification of the MHC II risk allele in MS patients alluded to a central role played by cluster of differentiation (CD4$^+$) T cells in the development of MS. Analyses of blood and CSF from MS patients further suggested that the disease implicated the recruitment of auto-reactive CD4$^+$ T lymphocytes from the periphery to the CNS, where they tethered, rolled, and adhered to endothelial cells lining the blood vessels. [Friese M A, Schattling B, & Fugger L (2014) Mechanisms of neurodegeneration and axonal dysfunction in multiple sclerosis. *Nature Reviews. Neurology* 10(4):225-238] The subsequent infiltration of these cells to the parenchyma is associated with breakdown of the blood brain barrier (BBB). [Gaitan M I, et al. (2011) Evolution of the blood-brain barrier in newly forming multiple sclerosis lesions. *Annals of Neurology* 70(1):22-29] The initial infiltration of CD4$^+$ effector cells of the T helper 17 (Th17) or Th1 subtypes lead to the secretion of pro-inflammatory cytokines, such as IL-17α and IFN-γ. [Kebir H, et al. (2007) Human TH17 lymphocytes promote blood-brain barrier disruption and central nervous system inflammation. *Nature Medicine* 13(10):1173-1175] These cytokines are cytotoxic and stimulate the recruitment of other immune cells, such as CD8⁺ effector T cells, which are able to further secrete cytotoxic cytokines or antigen-presenting cells, such as CD11c⁺ cells, which further prime and activate effector T cells within the CNS. This immune cascade together with the activation of CNS resident microglia releases cytotoxic cytokines and reactive oxygen or nitrogen species to damage the network of supporting oligodendrocytes. In addition to this aberrant immune activation, MS patients display a decreased ability to negatively regulate effector T cells, further impacting this immune activation. [Bettelli E, Korn T, & Kuchroo V K (2007) Th17: the third member of the effector T cell trilogy. *Current Opinion in Immunology* 19(6):652-657; Viglietta V, Baecher-Allan C, Weiner H L, & Hafler D A (2004) Loss of functional suppression by CD4+ CD25+ regulatory T cells in patients with multiple sclerosis. *The Journal of Experimental Medicine* 199(7):971-979] Axonal damage occurs early in demyelinating lesions, which correlate highly with infiltration of immune cells. [Ferguson B, Matyszak M K, Esiri M M, & Perry V H (1997) Axonal damage in acute multiple sclerosis lesions. *Brain: a Journal of Neurology* 120 (Pt 3):393-399]

The complexity of MS is highlighted by the heterogeneity of pathological patterns that occur in MS patients. These pathological hallmarks are subdivided in four distinct patterns. The initial pathological damage is predominantly regulated by the infiltration of T and B cells at the site of plaque formation (patterns I and II). Typically these pathological patterns coincide with the novel occurrence of plaques. Subsequently, there is a shift towards decreased cellular infiltration and increased neurodegeneration represented by sites of hypoxic insult leading to neuronal death and apoptosis (patterns III and IV). MS was originally thought to target white matter tissue, however extensive gray matter lesions have been identified in the early phases of MS progression. In the progressive stages of the disease, BBB breakdown does occur, but to a lesser extent in comparison to relapsing-remitting (RRMS). Furthermore, immune cell infiltrates are present in areas that maintain BBB permeability. [Lassmann H, van Horssen J, & Mahad D (2012) Progressive multiple sclerosis: pathology and pathogenesis. *Nature Reviews. Neurology* 8(10:647-656] This suggests that in progressive stages, immune activation takes place within the CNS independently of peripheral infiltration. At this stage of the disease, patients suffer from extensive brain atrophy and dilatation of ventricles.

In MS, loss of BBB integrity occurs early in the disease progression. Breakdown of the BBB primes tissue for the recruitment of leukocytes and subsequent neuronal damage. While the BBB normally sequesters immune cells outside of the CNS, it can also promote the penetration of immune cells to localized regions of inflammation within the CNS. Early in MS, endothelial cells (ECs) can enhance leukocyte infiltration by up-regulating both E- and P-selectin proteins on their membranes. [Engelhardt B & Ransohoff R M (2005) The ins and outs of T-lymphocyte trafficking to the CNS: anatomical sites and molecular mechanisms. *Trends in Immunology* 26(9):485-495] Furthermore, ECs can secrete leukocytes attractants such as chemokine ligand 2 (CCL2). [Biernacki K, Prat A, Blain M, & Antel J P (2001) Regulation of Th1 and Th2 lymphocyte migration by human adult brain endothelial cells. *Journal of Neuropathology and Experimental Neurology* 60(12):1127-1136] Following activation by inflammatory cytokines, ECs can express adhesion molecules, such as intracellular adhesion molecule-1 (ICAM-1) and vascular adhesion molecule-1, which enhance the extravasation of leukocytes through ECs. [Alvarez J I, Katayama T, & Prat A (2013) Glial influence on the blood brain barrier. *Glia* 61(12):1939-1958]

In the Experimental Autoimmune Encephalomyelitis (EAE) animal model, which is an accepted animal model of MS, invading immune cells most prominently target the spinal cord replicating the pathological patterns I and II of MS. [Rangachari M & Kuchroo V K (2013) Using EAE to better understand principles of immune function and autoimmune pathology. *Journal of Autoimmunity* 45:31-39] The adoptive transfer of CD4⁺ T cells from immunized mice into naïve mice confirmed that EAE was also a CD4⁺ T cell-mediated disease. [Paterson P Y (1960) Transfer of allergic encephalomyelitis in rats by means of lymph node cells. *The Journal of Experimental Medicine* 111:119-136] Initially, IFN-γ producing Th1 effector cells were believed to mediate the disease, as adoptive transfers of Th1 cells induced EAE in mice. However, the discovery that the induction of EAE was in fact dependent on a novel cytokine, IL-23, led to the identification of a novel CD4⁺ T cell subtype, the IL-17 producing Th17 cells. [Cua D J, et al. (2003) Interleukin-23 rather than interleukin-12 is the critical cytokine for autoimmune inflammation of the brain. *Nature* 421(6924):744-748; Becher B, Durell B G, & Noelle R J (2002) Experimental autoimmune encephalitis and inflammation in the absence of interleukin-12. *The Journal of Clinical Investigation* 110(4):493-497; Park H, et al. (2005) A distinct lineage of CD4 T cells regulates tissue inflammation by producing interleukin 17. *Nature Immunology* 6(11):1133-1141] Thus, both Th1 and Th17 CD4⁺ T cell subsets can mediate EAE. Importantly, both IFN-γ and IL-17 secreting cells were shown to be enriched in the CSF of MS patients. [Kebir H, et al. (2007) Human TH17 lymphocytes promote blood-brain barrier disruption and central nervous system inflammation. *Nature Medicine* 13(10):1173-1175; Traugott U & Lebon P (1988) Multiple sclerosis: involvement of interferons in lesion pathogenesis. *Annals of Neurology* 24(2):243-251] In EAE, both subtypes of T cells have been shown to promote differential immune cell recruitments, with Th1 promoting monocytic inflammation and Th17 promoting neutrophilic infiltrates. [Kroenke M A, Carlson T J, Andjelkovic A V, & Segal B M (2008) IL-12- and IL-23-modulated T cells induce distinct types of EAE based on histology, CNS chemokine profile, and response to cytokine inhibition. *The Journal of Experimental Medicine* 205(7):1535-1541] In addition, atypical forms of EAE may arise from a shift in the expression of these pro-inflammatory cytokines. Higher expression of IL-17 is associated with more prevalent brain lesions whereas it may be protective in the spinal cord. [Stromnes I M, Cerretti L M, Liggitt D, Harris R A, & Goverman J M (2008) Differential regulation of central nervous system autoimmunity by T(H)1 and T(H)17 cells. *Nature Medicine* 14(3):337-342] These studies raise the possibility that T cell subsets may mediate differential functions depending on their tissue localization.

In addition to the well-established role of CD4⁺ T-cells in the development of EAE, studies have also identified other subsets of T cells that play a crucial role in EAE. Adoptive transfers of CD8⁺ T cells induce an atypical form of EAE with lesions localized to white matter of the cerebellum. In addition, this model induces wide-scale oligodendrocyte death resembling patterns III and IV of MS patients. [Bitsch A, Schuchardt J, Bunkowski S, Kuhlmann T, & Bruck W (2000) Acute axonal injury in multiple sclerosis. Correlation with demyelination and inflammation. *Brain: a Journal of Neurology* 123 (Pt 6):1174-1183] Recent findings highlight the occurrence of multiple subsets of CD8⁺ T cells present in both EAE and MS. Initial studies using CD8$^{-/-}$ knockout mice have shown increased severity of the disease and more frequent relapses, indicating a possible regulatory role of CD8$^+$ T cells in EAE. [Jiang H, Zhang S I, & Pernis B (1992) Role of CD8+ T cells in murine experimental allergic encephalomyelitis. *Science* 256(5060):1213-1215; Koh D R, et al. (1992) Less mortality but more relapses in experimental allergic encephalomyelitis in CD8-/- mice. *Science* 256(5060):1210-1213] Furthermore, CD8$^+$/CD28$^{-/-}$ T cells have been shown to induce immunosuppressive phenotypes in EAE by interrupting co-stimulatory molecule expression on the surface of CD4$^+$ T cells. [Montero E, et al. (2004) Regulation of experimental autoimmune encephalomyelitis by CD4+, CD25+ and CD8+ T cells: analysis using depleting antibodies. *Journal of Autoimmunity* 23(1):1-7]

Although T cells have been shown to mediate disease, B cells could also be involved in the pathophysiology of EAE. MS patients possess higher IgG levels in the CSF compared to age-matched controls, suggesting the presence of antibody-releasing cells within the CSF. Studies have found that B cells enhance EAE severity by promoting differentiation of Th1 and Th17 cells. Prior to EAE onset, a regulatory subset of B cells, able to regulate immune response, exist. This may provide a novel biomarker from which the shift of B cells from regulatory to pathogenic may correlate with MS onset. [Fillatreau S, Sweenie C H, McGeachy M J, Gray D, & Anderton S M (2002) B cells regulate autoimmunity by provision of IL-10. *Nature Immunology* 3(10):944-950]

SUMMARY

A novel molecular interplay between two members of the RGM family (RGMc and RGMa) is described and its application in modulating the permeability of the blood brain barrier (BBB), which finds utility in the treatment or prevention of various diseases and conditions, as well as in drug delivery applications.

In one embodiment, the disclosure provides use, methods of using and use in the manufacture of a medicament of RGMc, sRGMc or a functional fragment, variant or mimic thereof for decreasing the permeability of the BBB in a subject.

The disclosure further provides, use, methods of use and use in the manufacture of a medicament of RGMc, sRGMc or a functional fragment, variant or mimic thereof for stabilizing or restoring the BBB in a subject.

The disclosure further provides, use, methods of use and use in the manufacture of a medicament of an agent that inhibits RGMa for decreasing the permeability of the BBB in a subject.

The disclosure further provides, use, methods of use and use in the manufacture of a medicament of an agent that inhibits RGMa for stabilizing or restoring the BBB in a subject.

The disclosure further provides, use, methods of use and use in the manufacture of a medicament of an agent that inhibits RGMc for disrupting BBB integrity in a subject.

The disclosure further provides, use, methods of use and use in the manufacture of a medicament of an agent, wherein the agent is RGMa, sRGMa, a functional fragment, variant or mimic thereof or stimulates RGMa, for disrupting BBB integrity in a subject.

The disclosure further provides, use, methods of use and use in the manufacture of a medicament of an agent that inhibits RGMc for increasing the permeability of the BBB of a subject to a molecule present in the blood stream of the subject.

The disclosure further provides, use, methods of use and use in the manufacture of a medicament of an agent, wherein the agent is RGMa, sRGMa, a functional fragment, variant or mimic thereof or stimulates RGMa, for increasing the permeability of the BBB of a subject to a molecule present in the blood stream of the subject.

Also provided are pharmaceutical compositions comprising RGMc, sRGMc or a functional fragment, variant or mimic thereof and a pharmaceutically acceptable carrier or excipient for decreasing the permeability of the BBB in a subject and/or for stabilizing or restoring the BBB in a subject.

Also provided are pharmaceutical compositions comprising an agent that inhibits RGMa and a pharmaceutically acceptable carrier or excipient for decreasing the permeability of the BBB in a subject and/or for stabilizing or restoring the BBB in a subject.

Also provided are pharmaceutical compositions comprising an agent that inhibits RGMc and a pharmaceutically acceptable carrier or excipient for disrupting BBB integrity in a subject.

Also provided are pharmaceutical compositions comprising an agent, wherein the agent is RGMa, sRGMa, a functional fragment, variant or mimic thereof or stimulates RGMa and a pharmaceutically acceptable carrier or excipient, for disrupting BBB integrity in a subject.

Also provided are pharmaceutical compositions comprising an agent that inhibits RGMc and a pharmaceutically acceptable carrier or excipient, for increasing the permeability of the BBB of a subject to a molecule present in the blood stream of the subject.

Also provided are pharmaceutical compositions comprising an agent, wherein the agent is RGMa, sRGMa, a functional fragment, variant or mimic thereof or stimulates RGMa and a pharmaceutically acceptable carrier or excipient for increasing the permeability of the BBB of a subject to a molecule present in the blood stream of the subject.

The disclosure further provides use, methods of using and use in the manufacture of a medicament of RGMc, sRGMc or a functional fragment, variant or mimic thereof for promoting re-myelination in a subject.

The disclosure further provides use, methods of using and use in the manufacture of a medicament of RGMc, sRGMc or a functional fragment, variant or mimic thereof for preventing de-myelination in a subject.

Also provided are pharmaceutical compositions comprising RGMc, sRGMc or a functional fragment, variant or mimic thereof and a pharmaceutically acceptable carrier or excipient for promoting re-myelination in a subject.

Also provided are pharmaceutical compositions comprising RGMc, sRGMc or a functional fragment, variant or mimic thereof and a pharmaceutically acceptable carrier or excipient for preventing de-myelination in a subject.

BRIEF DESCRIPTION OF DRAWINGS

FIG. 1B shows Neogenin binds RGMa, RGMb and RGMc at various sites. RGMa was shown to bind the Fibronectin type-III$_{(3-4)}$ domain of Neogenin, whereas the binding sites for RGMb and RGMc are located on the Fibronectin type-III$_{(5-6)}$ domains.

FIG. 3A-3B—FIG. 3 show RGMc levels in control and EAE animals. (A) RGMc protein expression in sera of control or EAE mice at days 5, 10, 18, and 30 post-induction measured by ELISA; (B) RGMc protein in sera of control and EAE mice at day 18 post-induction analyzed by Western blotting. Quantification of RGMc levels is normalized to transferrin. Data are means±SEM (n=3). **p<0.01.

FIG. 4A-4F—FIG. 4 shows sRGMc treatment decreases the clinical severity of EAE-induced mice. Purified sRGMc protein expression was analyzed by Western blot under non-reducing conditions and by coomassie staining (A). Body condition score in EAE-induced animals treated with vehicle or injected with 20 mM sRGMc intravenously (i.v.) every 3 days for the duration of disease course (arrowheads) (B) or 20 mM sRGMc intraperitoneally (i.p.) injected at days 3, 6, and 9 for the duration of disease course (arrowheads) (C). Relative incidence of EAE in animals treated with vehicle or 20 mM sRGMc by i.p. (D). Day of onset of EAE in animals treated with vehicle or 20 mM sRGMc i.p. (E). sRGMc treatment is stable for 24 h post treatment and restores sRGMC levels to control levels, as observed by ELISA (F). Data are means±SEM (n=3-15 animals per group). p<0.01; *p<0.0001.

FIG. 5A-5C—FIG. 5 shows RGMc knockout animals (KO) could be susceptible to EAE. (A) Body condition score in EAE-induced wild type (WT) animals or selective homozygous deletion of RGMc (129S-Hfe2$^{tm1Nca}$/J) (RGMc KO). (B) Day of onset of EAE in RGMc KO and control (WT). (C) EAE incidence in RGMc knockout animals (KO) or control (WT). Data are means±SEM (n=10 animals per group).

FIG. 6A-6D—FIG. 6 shows sRGMa is up-regulated in EAE and interferes with sRGMc for binding to Neogenin. (A) sRGMa expression in the sera of control mice and in mice induced with EAE at days 5, 10, 18, and 30 analyzed using an RGMa ELISA kit as described in the Examples. (B) Body condition scores of 6-week old EAE-induced mice treated with PBS (Vehicle), every three days with 20 mM sRGMc, or with 20 mM sRGMc in conjunction with 40 mM sRGMa. (C) Binding of Neogenin to bovine serum albumin (Neogenin+BSA), to RGMa (Neogenin+RGMa), and to RGMc (Neogenin+RGMc) in RGMa-AP and in RGMc-AP. Constructs overexpressing His-tagged sRGMa, sRGMc and the extracellular domains of Neogenin (Ec-Neogenin) were coated onto Poly-L-Lysine coated wells. Alkaline Phosphatase (AP)-tagged proteins (EC-Neogenin or RGMa or RGMc) were then added to each well and incubated at 37° C. for 1 h. Each well was washed and equilibrated with AP developing buffer (100 mM NaHCO$_3$, 1 mM MgCl$_2$). The reaction was initiated using AP developing buffer supplemented with p-nitrophenyl phosphate and then stopped following color development by adding 50 µl (0.1M) NaOH. The absorbance of each reaction was measured using a microplate autoreader at 405 nm as described in the Examples. (D) Binding of Neogenin-AP to bovine serum albumin (Neogenin-AP+BSA), to RGMa (Neogenin-AP+RGMa), and to RGMc (Neogenin-AP+RGMc). Competition assay was performed as described in the Examples and above but in which the constructs were reversed. Data are means±SEM (n=3-10 animals per group, A-B); n=3 in triplicates (binding assays, C-D). *p<0.05, **p<0.01.

FIG. 8A-8D—FIG. 8 shows sRGMc treatment has no effect on naïve antigen-presenting cells. Mice induced with EAE were treated with PBS (Vehicle) or with 20 mM sRGMc (RgMc) and were sacrificed 10 days post-induction. Splenocytes were harvested and analyzed as described in the Examples for the percentage of (A) CD11c (dendritic cell), (B) CD11b (myeloid cell), and (C) coactivation markers CD80 on B cells and (D) coactivation markers CD86 cells on B cells. Data are means±SEM (n=15 animals per group).

FIG. 9A-9C—FIG. 9 shows sRGMc treatment has no effect on the adhesion properties of naïve T and B cells. Mice induced with EAE were treated with PBS (Vehicle) or with 20 mM sRGMc (RgMc) and were sacrificed 10 days post-induction. Splenocytes were harvested and analyzed as described in the Examples for (A) ICAM-1 expression on B cell, (B) ICAM-1 expression on CD8$^+$ T cells, (C) ICAM-1 and CD62L expressions in CD4$^+$ T cells. Data are means±SEM (n=15 animals per group).

FIG. 10A-10B—FIG. 10 shows sRGMc treatment has no effect on activated immune cells. Mice induced with EAE were treated with either PBS (Vehicle) or with sRGMc (RgMc) and sacrificed 10 days post induction. Splenocytes or draining lymph nodes (caudal, sciatic, lumbar) cells were harvested, stimulated with PMA and ionomycin as described in the Examples. Expression of activated CD4$^+$ T cells secreting IL-17A or IFN-γ in (A) splenocytes or (B) Draining lymph nodes (caudal, sciatic, lumbar) cells. Data are means±SEM (n=15 animals per group).

FIG. 11A-11B—FIG. 11 shows sRGMc treatment has no effect on antigen-specific immune cells. Mice induced with EAE were treated with PBS or RGMc. Splenocytes were harvested 10 days post-induction as described in the Examples. (A) CD4$^+$ T cell proliferation as measured using CFSE incorporation in splenocytes treated with 0 or 30 µg/mL MOG(35-55) (B) Levels of IL-17 and IFN-γ in splenocytes pulsed with 0, 30, or 100 µg/mL MOG(35-55). Data are means±SEM (n=15 animals per group).

FIG. 13A-13C—FIG. 13 shows sRGMc treatment reduces the number of cellular infiltrates and the extent of de-myelination in EAE-induced mice. Cervical cord sections were isolated from mice induced with EAE (day 18) and treated with either PBS (Vehicle) or sRGMc (RGMc)

and stained with H&E in combination with Luxol Fast Blue as described in the Examples. (A) Representative images of cervical spinal cord sections showing less demyelinating foci in EAE-induced mice treated with sRGMc. (B) Quantification of Luxol fast blue staining (mean pixel intensity) in vehicle-treated (normalized to sham animals) and in RGM-treated EAE animals. (C) Inflammatory index scores in cervical sections in vehicle-treated and in RGM-treated EAE animals. Data are means±SEM (n=6 animals per group). **$p<0.01$.

Figures 14A, 14B:
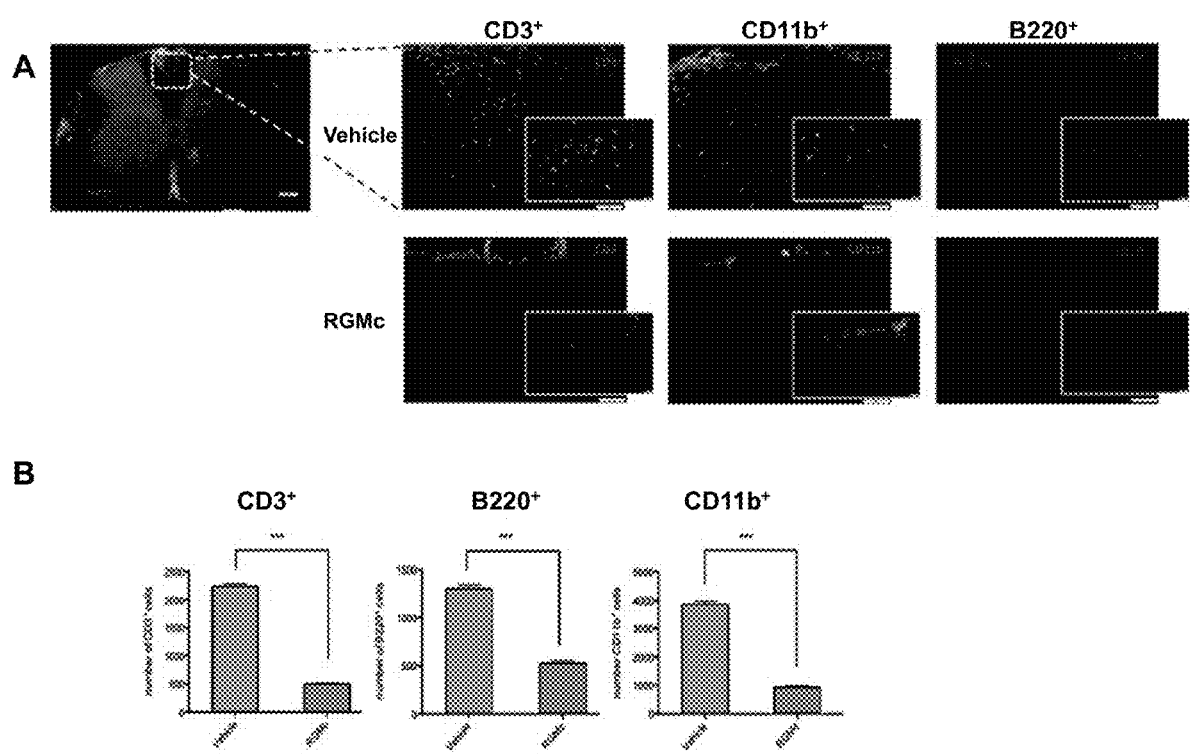

FIG. 14A-14B—FIG. 14 shows sRGMc reduces the amount of immune infiltrates in the spinal cord of EAE-induced mice. Cervical cord sections were isolated from mice induced with EAE (day 18) and treated with either PBS (Vehicle) or sRGMc (RGMc), cryo-sectioned and stained with CD3, CD11b, or B220 surface markers as described in the Examples. Representative images (A) and quantification of cells in 7 regions of spinal cord sections (B) stained with CD3, CD11b, or B220 surface markers. Data are means±SEM (n=6 animals per group). ***$p<0.001$.

FIG. 15A-15D—FIG. 15 shows sRGMc decreases blood brain barrier (BBB) endothelial cell permeability by interfering with RGMa-mediated Rho activation. (A) Neogenin expression was analyzed on the membrane of b.end3 cells using immunohistochemical staining and by Western blot. (B) Crystal violet staining showing the b.end3 cell monolayer, (C) Representative diagram of the boyden chamber set up and (D) BBB permeability in b.end3 cells. Serum-starved cells were incubated for 4 h with RGMa (10 μg/ml), C3 Transferase (10 μg/mL) or Y27632 (10 μM) or sRGMc (10 μg/mL) and were then incubated with sRGMa (5 μg/mL) for 18 h followed by seeding of Dextran-FITC onto the upper chamber. Extravasation was measured over a period of 60 min as described in the Examples. n=3, performed in triplicates.

Figures 16A, 16B:
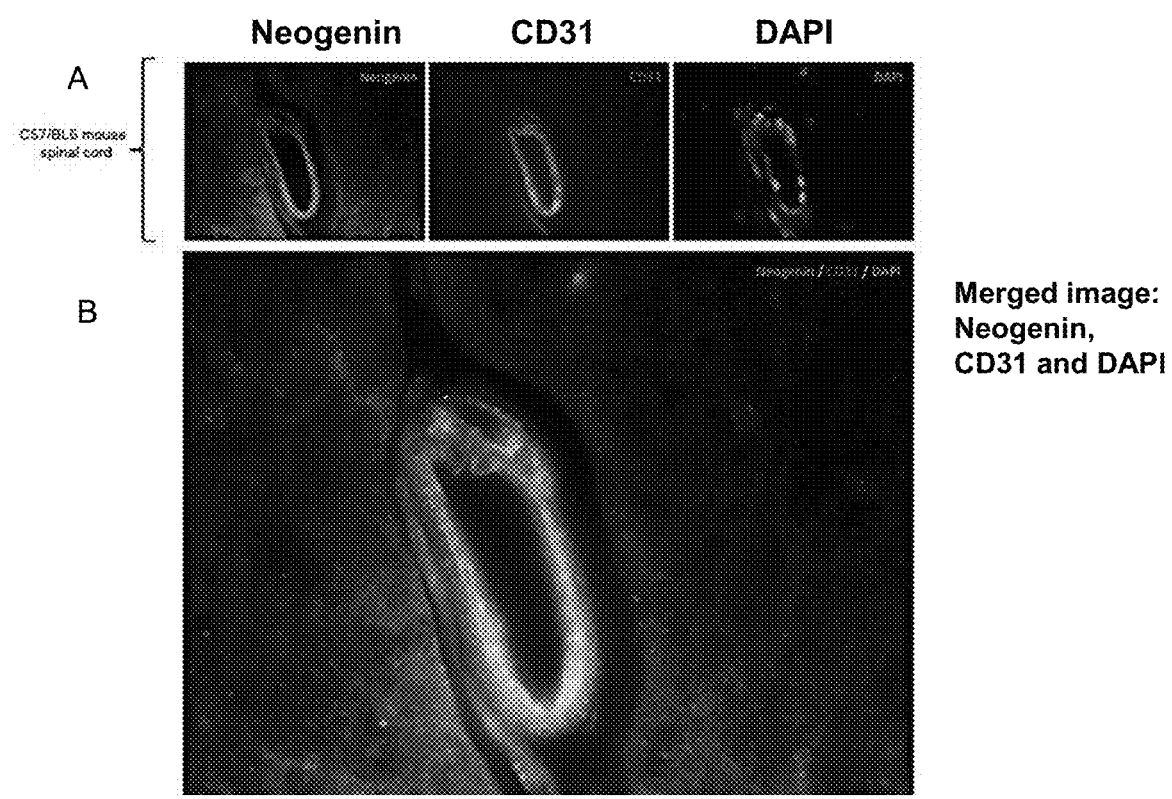

FIG. 16A-16B—FIG. 16 shows Neogenin expression in endothelial cells in mouse spinal cord. (A) Composition images of cervical spinal cord sections of C57/BL6 mice stained for Neogenin shown in red (color not shown), for endothelial cell stained with anti-CD31 antibody shown in green (color not shown) and for nucleus stained with DAPI in blue (color not shown) (B) Merged image of Neogenin staining, CD31 staining and DAPI staining, indicated by alteration in color (color not shown), which indicated colocalization of Neogenin and CD31 (endothelial cell marker).

Figures 17A, 17B:
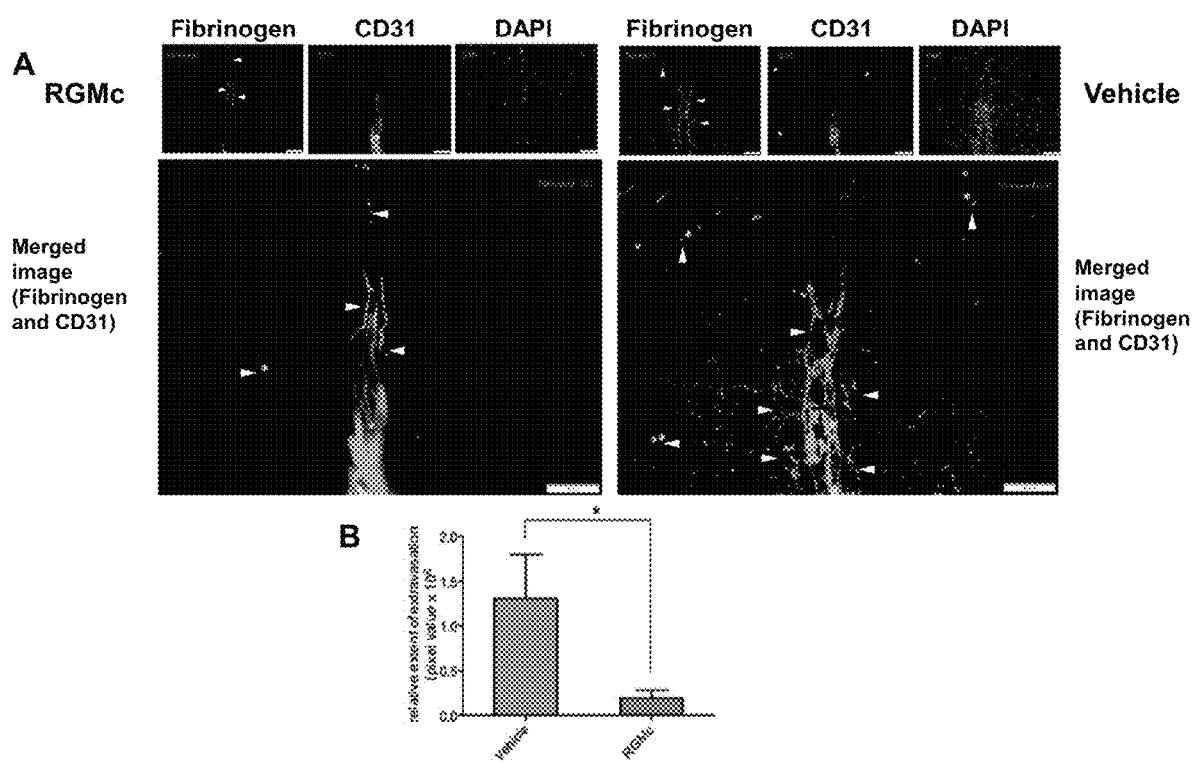

FIG. 17A-17B—FIG. 17 shows sRGMc reduces BBB permeability. (A) Immunohistochemical staining of cervical spinal cords of 18 days EAE-induced mice treated every 3 days with sRGMc or Vehicle. Shown are representative images of fibrinogen extravasation in red (color not shown) and arrowheads around blood vessels stained with anti-CD31 antibody in green (color not shown) and asterisks, nuclei stained with DAPI in blue (color not shown), and merged images of fibrinogen staining and CD31 staining indicated by alteration in color (color not shown), which indicated colocalization of fibrinogen and blood vessels. Scale bars, 50 μm. (B) Quantitative analysis of perivascular extravasation of fibrinogen by measuring the relative pixel intensity in sRGMc-treated and vehicle-treated animals (n=6).

Figure 18A:
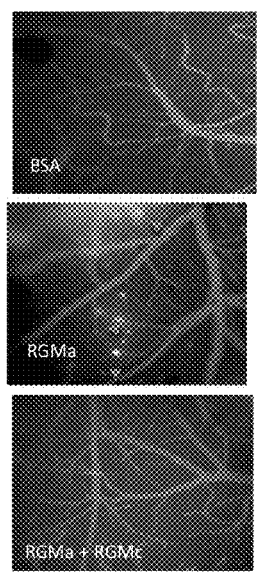
Figure 18B:
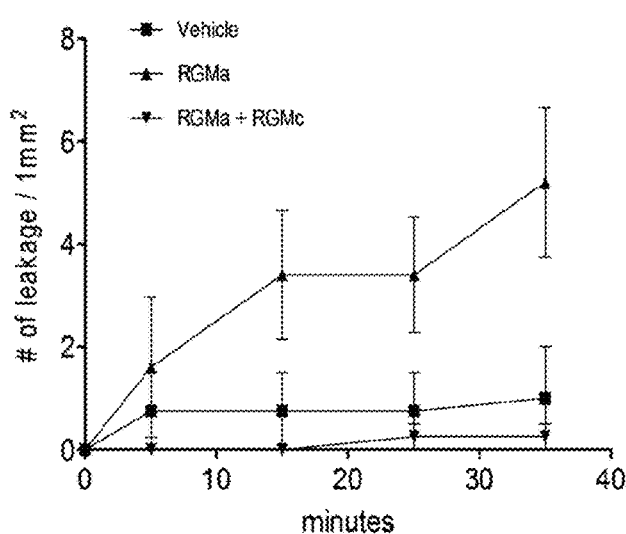

FIG. 18A-18B—FIG. 18 shows RGMc protects BBB integrity. Mice were treated with RGMa (70 ug), RGMa (70 ug)+RGMc (70 ug), or Vehicle (1% BSA) 18 h prior to widefield imaging (100-300 ms exposure) prior to and following intravenous injection of Texas Red dye (0.5 mg) over time. (A) Representative images showing the leakage of Texas Red dye. (B) Quantification of the leakage of Texas Red dye (measured as the number of leakage sites/mm²).

Figure 19:
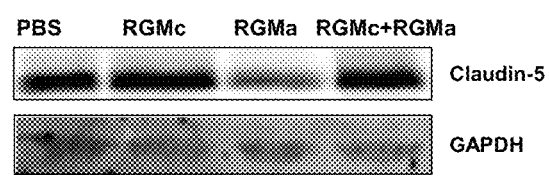

FIG. 19—FIG. 19 shows a representative immunoblot of Claudin 5 expression in endothelial cells treated with PBS, RGMc, RGMa or RGMc+RGMa. End3-endothelial cells (ECs) were used to generate an in vitro model of the human endothelial cell barrier lining the choroid plexus. b.end3-ECs were plated at 2×10⁵ cells per dish in DMEM, and were allowed to reach confluency at which point they were serum-starved for 6 h. Cells were pretreated for 6 h with PBS, RGMc, RGMa or RGMc+RGMa. Western blotting was performed on the lysates with Claudin-5 and GAPDH antibodies. This shows that RGMa induces a downregulation of Claudin 5, which is restored by RGMc.

Figure 20:
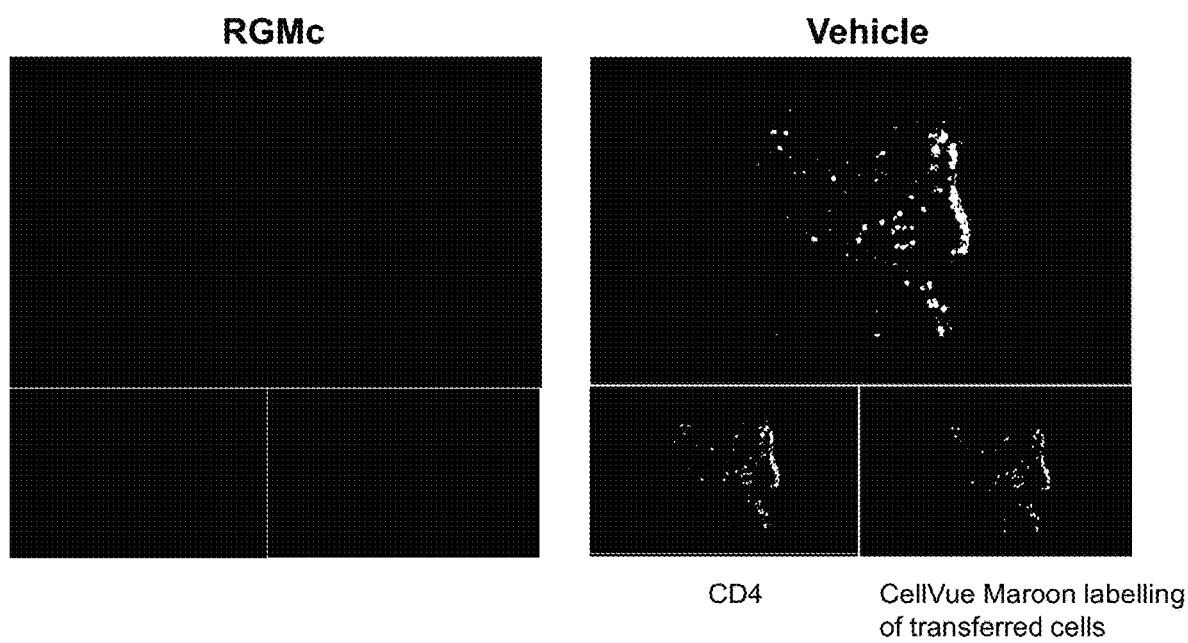
Figures 21A, 21B, 21C:
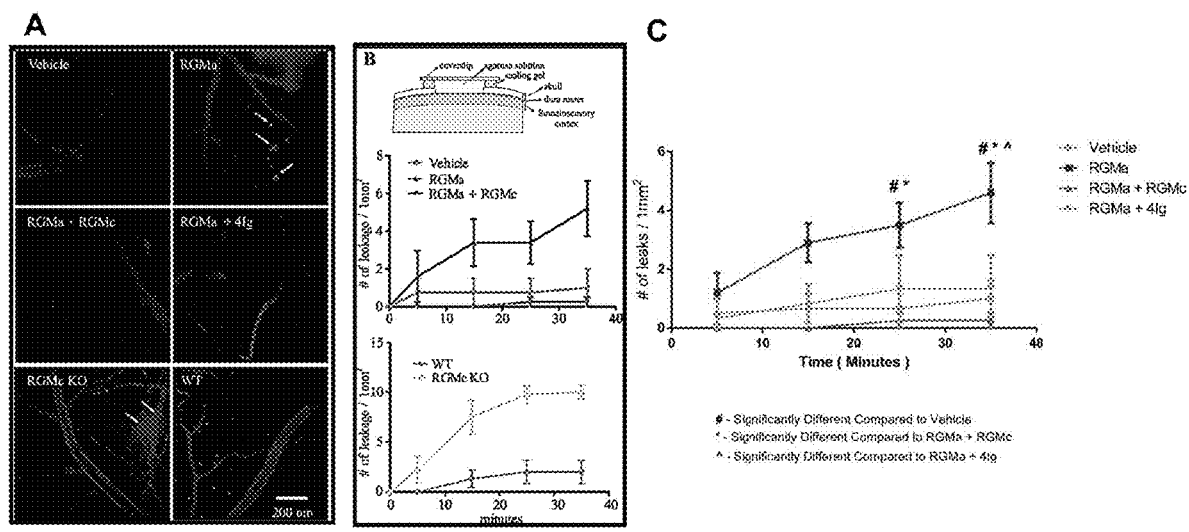

FIG. 20—FIG. 20 shows CD4 positive transplanted cells are observed in cells treated with Vehicle but not RGMc. EAE was passively induced in 6-8 week old C57Bl/6 mice and sacrificed. Donor animals were immunized with 100 ug MOG(35-55) and sacrificed at day 10. Splenocytes were harvested and re-stimulated for three days with 33 ug/mL MOG(35-55) in the presence of 20 ng/ml rmIL-23. Cells were then labelled with CellVue Maroon and injected into recipient animals treated with RGMc or vehicle as well as PTx on day 0 and day 2. Recipient animals were treated every 3 days (with PBS or RGMc) and sacrificed on day 8 and spinal cords sectioned for immunofluorescence staining with CD4 antibody, or using the labelling from cell vue. This shows that in PBS, but not in RGMc, CD4 positive transplanted cells were penetrating the BBB.

FIG. 21A-21C—FIG. 21 shows the effects of RGMc on BBB integrity in vivo. BBB integrity was assessed in mice treated with PBS (Vehicle), RGMa, RGMc, RGMa+ immunoglobulin domain of Neogenin (4Ig). Widefield imaging was then carried out under a Olympus microscope (BX6 1WI) prior to and following the injection of Texas red dye (100 uL, I.V., 5 mg/ml) using 100-300 ms exposure. Recording was performed from 0 min to 35 min following injection. Texas dye leakage was also assessed in RGMc knockout (KO) and wild type (WT) mice. The leakage of Texas-red dye was quantified by a blind experimenter measuring the number of leakage sites/mm². (A) Representative images of Texas red dye: PBS (Vehicle), RGMa, RGMa+RGMc and RGMa+4Ig (immunoglobulin domain of Neogenin). Quantification of the leakage of Texas Red dye in animals treated with (B) PBS (Vehicle), RGMa or RGMa+RGMc or in RGMc KO and WT mice or (C) PBS (Vehicle), RGMa, RGMa+RGMc or RGMa+4Ig.

Figure 22:
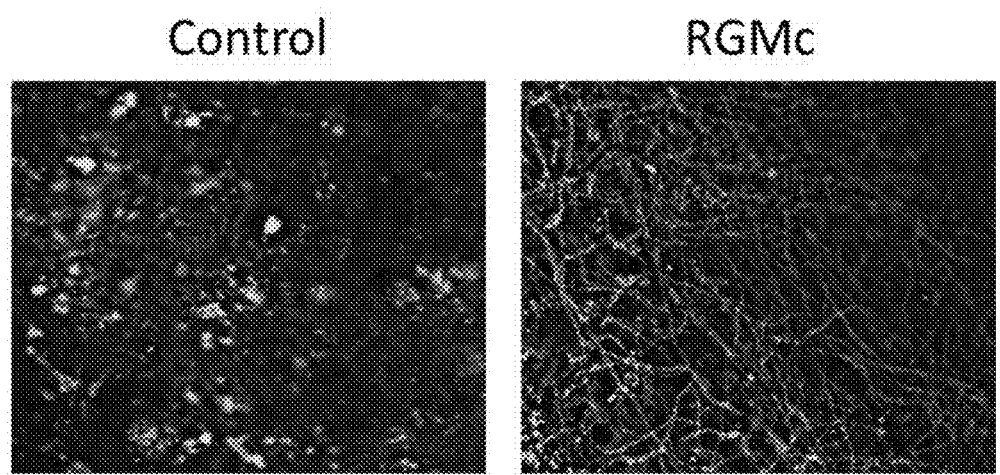

FIG. 22—FIG. 22 shows sRGMc treatment promotes extensive remyelination in cerebral explants. Explants were demyelinated with lysolecithin and treated with sRGMc. Explants were stained for myelin basic protein (MBP).

Figure 23:
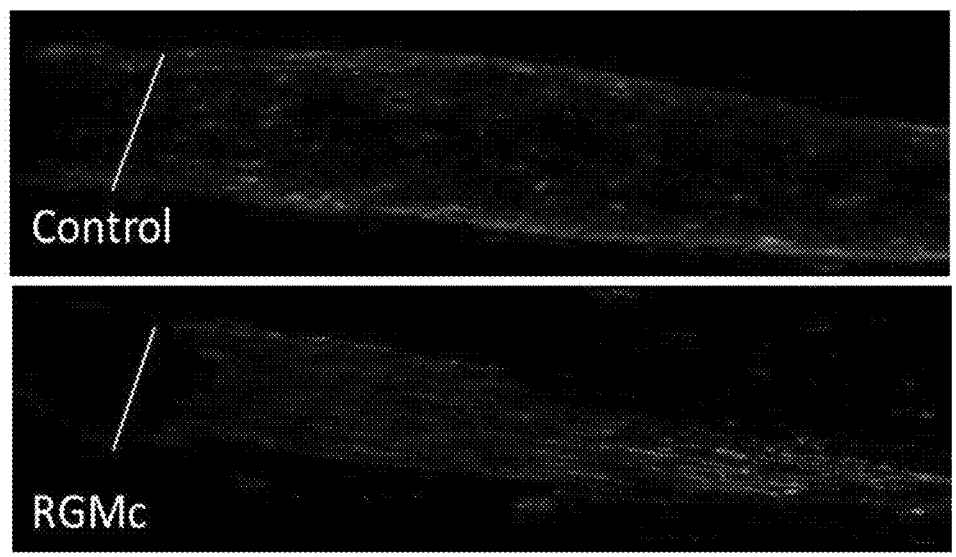

FIG. 23—FIG. 23 shows treatment with sRGMc promotes regeneration in an optic crush model. Optic nerves were treated with sRGMc and stained for axonal fibers with GAP43. Line represents the site of injury.

Figure 24A:
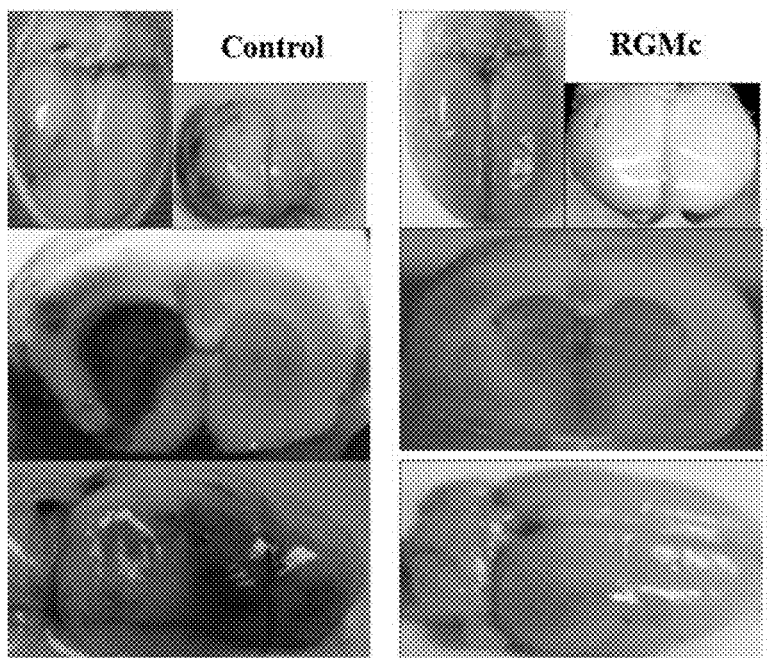
Figure 24B:
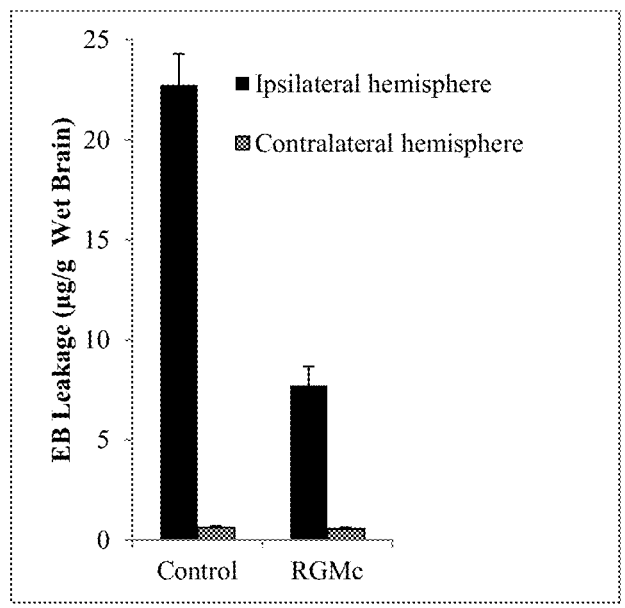

FIG. 24A-24B—FIG. 24 shows treatment with sRGMc reduces Evans Blue penetration into CNS tissue in a middle cerebral artery occlusion model.

Figure 25:
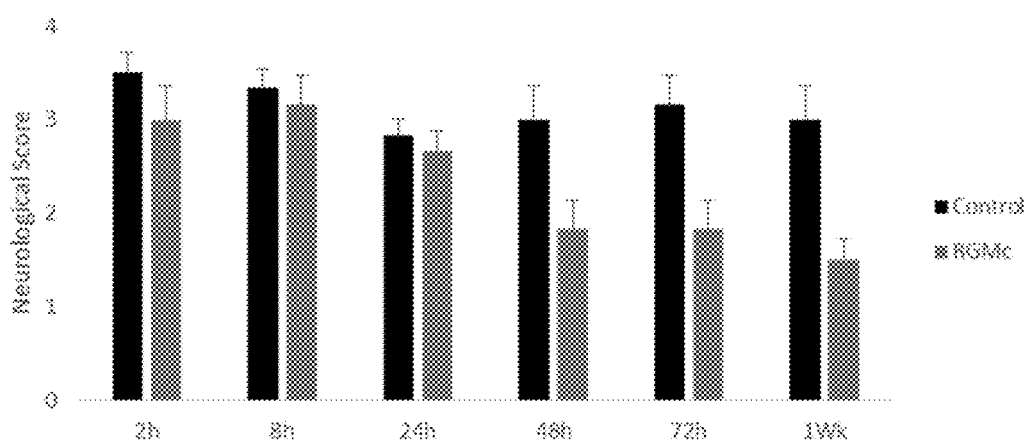

FIG. 25—FIG. 25 shows treatment with sRGMc promotes functional recovery after middle cerebral artery occlusion.

DETAILED DESCRIPTION

Figures 1A, 1B:
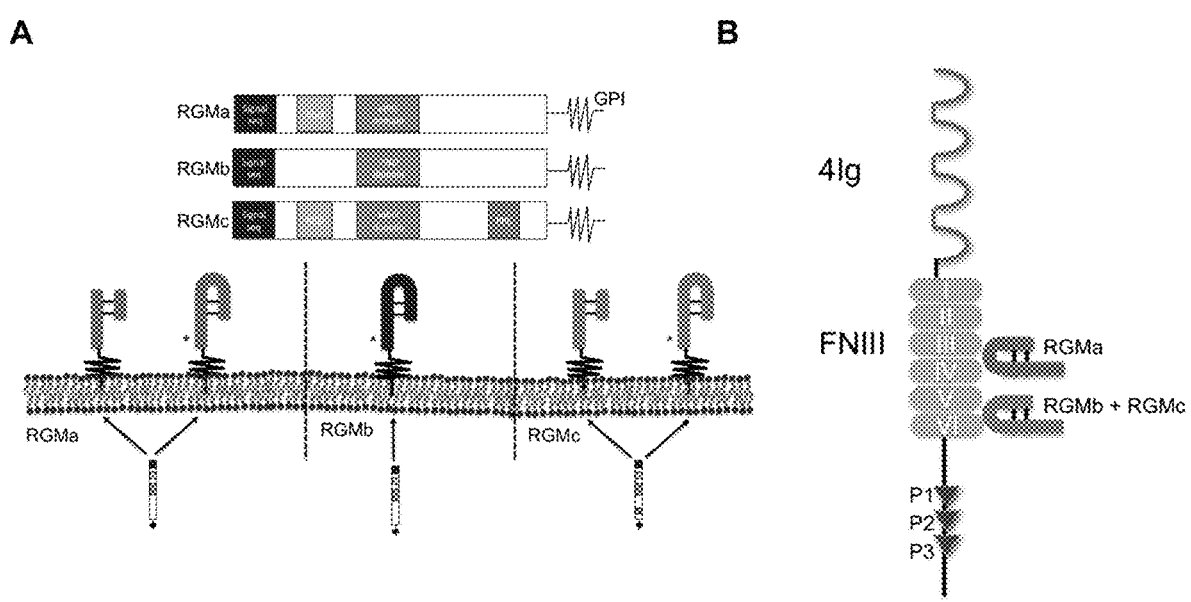
FIG. 1A-1B—FIG. 1A shows the structure of RGM proteins. All RGM proteins share ~40% primary amino acid sequence. All members possess an N-terminal signal sequence targeting the proteins to the membrane where they are anchored using a GPI-anchor sequence on the most C-terminal portion. All RGMs possess a von Willebrand factor domain whereas both RGMa and RGMc possess an auto-catalytic RGD motif able to generate a single-chain and a two-chain membrane-bound protein. RGMb is only expressed as a single-chain membrane-bound protein. Single-chain isoforms can be cleaved from the membrane to generate soluble protein fragments (asterisks).

The RGMa/Neogenin pathway is involved in neuronal survival, as well as regenerative failure and the immune response in EAE animals. Two other members of the RGM family have also been characterized in mammals: RGMb (DRAGON), and RGMc (Hemojuvelin, HFE2). These proteins share ~40% identity in primary amino acid sequences and all three express an N-terminal signal peptide sequence followed by an arginine-asparagine-aspartic acid (RGD) motif. Other key structures include the presence of a partial von Willebrand type D domain and a carboxy-terminal GPI anchor [Severyn C J, Shinde U, & Rotwein P (2009) Molecular biology, genetics and biochemistry of the repulsive guidance molecule family. *The Biochemical Journal* 422(3):393-403] (FIG. 1A). Both RGMa and RGMc can undergo autocatalytic cleavage generating a membrane-bound isoform that can further undergo post-translational cleavage to secrete soluble fragments. [Tassew N G, Charish J, Seidah N G, & Monnier P P (2012) SKI-1 and Furin generate multiple RGMa fragments that regulate axonal growth. *Developmental Cell* 22(2):391-402; Nili M, David L, Elferich J, Shinde U, & Rotwein P (2013) Proteomic analysis and molecular modelling characterize the iron-regulatory protein haemojuvelin/repulsive guidance molecule c. *The Biochemical Journal* 452(1):87-95] These proteins regulate complex biological activities, including cell adhesion, axonal outgrowth, axonal guidance, immune regulation, and systemic iron regulation. All of these functions are mediated through the trans-membrane receptor Neogenin, which is broadly expressed in the body.

Neogenin is a type-I transmembrane protein that is homologous to the well-known tumor suppressor receptor, Deleted in Colorectal Cancer (DCC). Both of these receptors possess an extracellular domain containing four immuno-globulin (4Ig) domains and six-fibronectin type III (FNIII) domains (FIG. 1B). The intracellular regions differ between the two receptors except for 3 conserved regions termed P1, P2, and P3. Unlike DCC, Neogenin is expressed broadly outside of the CNS in tissues including: lung, heart, gut, kidney, liver, skeletal muscle, and bone. The well-known Netrin-1 ligand, known to bind DCC at the $FNIII_{(4-5)}$ domains was also shown to bind to Neogenin at the same location [Cole S J, Bradford D, & Cooper H M (2007) Neogenin: A multi-functional receptor regulating diverse developmental processes. *The International Journal of Biochemistry & Cell Biology* 39(9):1569-1575] and promote attraction of supraoptic axons in the *Xenopus* forebrain. [Xu K, et al. (2014) Neural migration. Structures of netrin-1 bound to two receptors provide insight into its axon guidance mechanism. *Science* 344(6189):1275-1279] Neogenin was also shown to bind RGM proteins, with the RGMa-Neogenin interaction first identified through its chemo-repulsive effect in temporal retinal axons of the chick anterior optic tectum. [Wilson N H & Key B (2006) Neogenin interacts with RGMa and netrin-1 to guide axons within the embryonic vertebrate forebrain. *Developmental Biology* 296(2):485-498] As shown in FIG. 1B, the binding site of RGMa on Neogenin resides within the $FNIII_{(3-4)}$ domain whereas the binding sites for RGMb and RGMc are located on the $FNIII_{(5-6)}$ domains. [Tassew N G, Charish J, Seidah N G, & Monnier P P (2012) SKI-1 and Furin generate multiple RGMa fragments that regulate axonal growth. *Developmental Cell* 22(2):391-402 Yang F, West A P, Jr., Allendorph G P, Choe S, & Bjorkman P J (2008) Neogenin interacts with hemojuvelin through its two membrane-proximal fibronectin type III domains. *Biochemistry* 47(14):4237-4245; Bell C H, et al. (2013) Structure of the repulsive guidance molecule (RGM)-neogenin signaling hub. *Science* 341(6140):77-80] Furthermore, the functions of both RGMb and RGMc are mediated through Neogenin signaling. [Enns C A, Ahmed R, & Zhang A S (2012) Neogenin interacts with matriptase-2 to facilitate hemojuvelin cleavage. *The Journal of Biological Chemistry* 287(42):35104-35117; Ma C H, et al. (2011) The BMP coreceptor RGMb promotes while the endogenous BMP antagonist noggin reduces neurite outgrowth and peripheral nerve regeneration by modulating BMP signaling. *The Journal of Neuroscience: the Official Journal of the Society for Neuroscience* 31(50):18391-18400]

The discovery of RGMc, also known as Hemojuvelin, was completed by mapping the gene locus associated with an autosomal recessive disease, juvenile hemochromatosis (JH). [Enns C A, Ahmed R, & Zhang A S (2012) Neogenin interacts with matriptase-2 to facilitate hemojuvelin cleavage. *The Journal of Biological Chemistry* 287(42):35104-35117] JH presents as an early onset of iron overload typically in the first and second decade of life, and is caused by the lack of function of a liver-derived enzyme, hepcidin. [Ganz T (2007) Molecular control of iron transport. *Journal of the American Society of Nephrology: JASN* 18(2):394-400] RGMc knockout mice develop iron overload and a decreased hepcidin expression, which is similar to observations in JH. [Core A B, Canali S, & Babitt J L (2014) Hemojuvelin and bone morphogenetic protein (BMP) signaling in iron homeostasis. *Frontiers in Pharmacology* 5:104] RGMc protein also undergoes complex post-translational processing. The presence of an autocatalytic sequence results in two cell membrane proteins: i) a single-chain 50 KDa; and 2) a two-chain 30 KDa protein linked to a 20 KDa protein by di-sulfide bonds. The single-chain protein can be further processed by a pro-protein convertase, Furin, to release a 50 KDa fragment. [Kuninger D, Kuns-Hashimoto R, Nili M, & Rotwein P (2008) Pro-protein convertases control the maturation and processing of the iron-regulatory protein, RGMc/hemojuvelin. *BMC biochemistry* 9:9] Furthermore, single-chain RGMc can be cleaved by a serine-protease Matriptase-2 (MT2) to release a 36 KDa fragment. [Enns C A, Ahmed R, & Zhang A S (2012) Neogenin interacts with matriptase-2 to facilitate hemojuvelin cleavage. *The Journal of Biological Chemistry* 287(42):35104-35117] In hepatocytes, single-chain membrane-bound RGMc acts as a co-receptor for BMP-6 and induces hepcidin expression. [Andriopoulos B, Jr., et al. (2009) BMP6 is a key endogenous regulator of hepcidin expression and iron metabolism. *Nature Genetics* 41(4):482-487; Meynard D, et al. (2009) Lack of the bone morphogenetic protein BMP6 induces massive iron overload. *Nature Genetics* 41(4):478-481] Interestingly, the double-, but not the single-chain RGMc binds to Neogenin. [Yang F, West A P, Jr., Allendorph G P, Choe S, & Bjorkman P J (2008) Neogenin interacts with hemojuvelin through its two membrane-proximal fibronectin type III domains. *Biochemistry* 47(14):4237-4245; Kuns-Hashimoto R, Kuninger D, Nili M, & Rotwein P (2008) Selective binding of RGMc/hemojuvelin, a key protein in systemic iron metabolism, to BMP-2 and neogenin. *American Journal of Physiology. Cell Physiology* 294(4):C994-C1003] However, Neogenin knockout animals experience iron overload, have low levels of hepcidin, and reduced BMP signaling. [Lee D H, et al. (2010) Neogenin inhibits HJV secretion and regulates BMP-induced hepcidin expression and iron homeostasis. *Blood* 115(15):3136-3145] The mechanism by which Neogenin regulates iron is poorly understood with reports that it increases [Enns C A, Ahmed R, & Zhang A S (2012) Neogenin interacts with matriptase-2 to facilitate hemojuvelin cleavage. *The Journal of Biological Chemistry* 287(42):35104-35117] and decreases [Lee D H, et al. (2010) Neogenin inhibits HJV secretion and regulates BMP-induced hepcidin expression and iron homeostasis.

*Blood* 115(15):3136-3145] RGMc cleavage at the membrane. Soluble fragments of RGMc (sRGMc) play crucial roles in iron regulation. Whereas membrane-bound RGMc promotes hepcidin expression, sRGMc inhibits hepcidin expression by competing with BMP receptors for BMP ligands. [Babitt J L, et al. (2007) Modulation of bone morphogenetic protein signaling in vivo regulates systemic iron balance. *The Journal of Clinical Investigation* 117(7): 1933-1939]

RGMa serves a pivotal role in the proper development of the CNS, but its role ex-CNS has been largely understudied. Reports of increased RGMa expression on activated macrophages following spinal cord injury raised a potential route by which RGMa may mediate its chemo-repulsive signal on regenerating axonal fibers following injury. [Hata K, et al. (2006) RGMa inhibition promotes axonal growth and recovery after spinal cord injury. *The Journal of Cell Biology* 173(1):47-58; Kitayama M, Ueno M, Itakura T, & Yamashita T (2011) Activated microglia inhibit axonal growth through RGMa. *PloS One* 6(9):e25234] Indeed, in vitro co-cultures of mouse cortical neurons with macrophages supplemented with LPS inhibited neurite outgrowth and growth cone collapse. This RGMa effect is mediated through its interaction with Neogenin since knockdown of Neogenin decreased the chemorepulsive effect of activated macrophages. [Kitayama M, Ueno M, Itakura T, & Yamashita T (2011) Activated microglia inhibit axonal growth through RGMa. *PloS One* 6(9):e25234] Thus, RGMa is expressed on the surface of macrophages at the site of injury and is able to repulse regenerating fibers.

RGMa was recently linked to murine EAE, shifting our understanding of the physiological role of RGMa. This study was extended by genotyping polymorphisms in the RGMa locus of MS patients, which revealed to be highly correlative and followed a female bias, as observed in clinical onsets of the disease. RGMa polymorphisms correlated with elevated TNF-α and IFN-γ in the CSF and the peripheral blood mononuclear cells (PBMCs) of MS patients. [Nohra R, et al. (2010) RGMA and IL21R show association with experimental inflammation and multiple sclerosis. *Genes and Immunity* 11(4):279-293] In addition, soluble fragments of RGMa were found in the cerebrospinal fluid of RRMS patients, which decreased in patients undergoing intrathecal corticosteroid triamcinolone acetonide treatment. [Demicheva E, et al. (2015) Targeting Repulsive Guidance Molecule A to Promote Regeneration and Neuroprotection in Multiple Sclerosis. *Cell Reports*] LPS administration upregulated full-length and auto-catalytically cleaved forms of RGMa on the surface of bone marrow-derived dendritic cells, whereas its receptor, Neogenin, was expressed on the surface of CD4+ T cells. Western blot analysis identified a small GTPase, Rap1, which upon RGMa expression becomes elevated leading to an increase in T cell adhesion (observed via increased ICAM-1 expression). [Muramatsu, R., Kubo, T., Mori, M., Nakamura, Y., Fujita, Y., Akutsu, T., Okuno, T., Taniguchi, J., Kumanogoh, A., Yoshida, M., et al. (2011). RGMa modulates T cell responses and is involved in autoimmune encephalomyelitis. Nat. Med. 17, 488-494] This finding highlights a possible role for the RGMa-Neogenin signaling pathway in immune cell priming and activation.

RGMa has been further implicated in immune regulation through its ability to transiently (for 8 hours) hinder leukocyte extravasation in an in vivo model of Zymosan-A-induced peritonitis. RGMa is expressed in cytokeratin-positive epithelial cells in addition to polymorphonuclear leukocytes that expressed both RGMa and Neogenin. [Mirakaj V, et al. (2011) Repulsive guidance molecule-A (RGM-A) inhibits leukocyte migration and mitigates inflammation. *Proceedings of the National Academy of Sciences of the United States of America* 108(16):6555-6560] Moreover, Neogenin knockout animals lost the ability to develop immune response following an acute peritonitis model further suggest that the RGMa/Neogenin signaling pathway plays a role in acute inflammation. [Konig K, et al. (2012) The axonal guidance receptor neogenin promotes acute inflammation. *PloS one* 7(3):e32145] Taken together, the expression of RGMa on peripheral immune cells can modulate immune activation through dendritic cell-T cell signaling, or by inhibiting the infiltration of immune cells through epithelial cells. The potential of RGMa signaling in MS goes far beyond immune modulation. Inhibition of RGMa signaling promotes axonal regeneration in several spinal cord injury models as well as optic nerve injury models. [Hata K, et al. (2006) RGMa inhibition promotes axonal growth and recovery after spinal cord injury. *The Journal of Cell Biology* 173(0:47-58] Despite the recent focus on RGMa and its role as an immune modulator, the mechanism by which RGMa mediates its actions on the immune system is still poorly understood.

Thus, while RGMa and its interaction with Neogenin have been shown to play a crucial role in immune activation and priming, yet these studies fail to identify the role of soluble RGMa in the development of MS. Likewise, RGMc is also processed and co-exists with soluble RGMa in the serum. Both soluble proteins were shown to mediate their signal through their interactions with Neogenin.

The examples below evidence that the interplay between levels of RGMa and RGMc is crucial for the development of autoimmune diseases, such as MS. The role of RGMc in the development of autoimmune diseases was examined in the context of a mouse animal model of MS, i.e., EAE. Specifically: (1) if RGMc and RGMa levels are altered in the sera of EAE-induced mice, (2) the relationship between RGMa and RGMc in the development of EAE, (3) if RGMc modulates the molecular activation of the adaptive immune system in the development of EAE, and (4) if RGMc and/or RGMa modify the blood brain barrier (BBB) was examined.

As detailed in the Examples, the present inventors show that sRGMa present in the serum is up regulated following the induction of EAE and is able to increase the blood-brain EC barrier permeability, thereby increasing the infiltration of leukocytes within the CNS. The third member of the RGM family, RGMc, undergoes post-translational processing to generate soluble fragments present in the serum. As detailed in the Examples, a previously uncharacterized function for the iron regulatory protein RGMc is identified, whereby its expression in the sera of EAE-induced mice is significantly down regulated. Over-expression of sRGMc reduced the clinical severity in EAE-induced mice. RGMc knockout animals develop a worse disease progression that their wild-type control. Moreover, sRGMc treatment both diminished the extent of blood-borne proteins and the amount of leukocytes extravasating in the CNS. Lastly, it is shown in the Examples that this effect is mediated through the competition of these proteins for their receptor Neogenin on the endothelium of the BBB. Together, this data evidences a novel molecular interplay between two members of the RGM family and their regulation in the development of EAE.

As shown in the Examples, following the induction of EAE, both RGMa and RGMc levels are modulated prior to the onset of symptoms. In particular, sRGMc levels are significantly reduced in the sera of EAE mice. Thus, sRGMc levels are associated with disease progression, as exogenous expression of sRGMc in these EAE mice reverts the clinical severity.

That a complex physiological interplay exists between sRGMa and sRGMc is supported by the observation that sRGMa co-treatment completely abolishes EAE paralysis in sRGMc-treated mice. Using an in vitro competition assay a novel molecular interplay between these molecules was identified whereby both proteins compete for the same receptor, Neogenin. The binding site of RGMa (FNIII$_{(3-4)}$) differs from that of RGMc on Neogenin (FNIII$_{(5-6)}$). Thus, without being bound by a theory, it is believed that these molecules must regulate each other's binding through either negative allosteric modulation or by steric hindrance on Neogenin.

The data provided in the Examples evidences that sRGMc reduces BBB permeability as shown by a decrease in endogenous fibrinogen extravasation in EAE mice. Without being bound by a theory, it is proposed that sRGMa increases BBB permeability by activating the small GTPase RhoA. This small GTPase family comprising of RhoA, Rac1, and CDC42 links membrane receptors to cytoskeletal remodeling via actin assembly and disassembly. Indeed, the repulsive function of RGMa on projecting growth cones is mediated by the downstream activation of RhoA. [Hata K, et al. (2006) RGMa inhibition promotes axonal growth and recovery after spinal cord injury. *The Journal of Cell Biology* 173(1):47-58] In addition, numerous axon guidance molecules have been shown to activate the Rho signaling pathway to mediate their guidance cues. [Mueller B K, Mack H, & Teusch N (2005) Rho kinase, a promising drug target for neurological disorders. *Nature Reviews. Drug Discovery* 4(5):387-398] The direct downstream effector of RhoA is Rho kinase (ROCK), which is a serine/threonine protein kinase.

The work presented in the Examples is the first to identify the role of RGMc in the development of EAE. An observation that soluble RGM fragments possess contrasting expression patterns during the course of EAE led to an investigation of the role of exogenous sRGMc in the development of EAE. sRGMc-treated animals developed a delayed onset, a decreased percentage of incidence, and a diminished clinical severity of the disease course. Moreover, RGMc knockout animals developed a more severe disease progression than wild-type animals. As detailed in the Examples, an in vitro competition assay uncovered a molecular mechanism whereby sRGMc was shown to compete with sRGMa for the binding to Neogenin. This observation was confirmed in vivo by treating RGMC-treated animals in conjunction with sRGMa and observing a worsening disease phenotype. These findings prompted investigation of a role for RGMc in the infiltration of leukocytes within the CNS. Further, it was demonstrated that RGMc strengthened the integrity of the BBB in EAE.

Based on the published literature, the role of RGMc was exclusively believed to regulate iron expression. The Examples below provide evidence for the role of this protein in mediating RGMa signaling. The finding that sRGMc is able to protect and stabilize the BBB provides wider implications than MS as several disorders exhibit a breach of the BBB.

The blood-brain barrier (BBB) is a highly selective permeability barrier that separates the circulating blood from the brain extracellular fluid in the CNS. The BBB, which is formed by brain endothelial cells, allows the passage of water, some gases, and lipid-soluble molecules by passive diffusion, as well as the selective transport of molecules such as glucose and amino acids that are crucial to neural function, while restricting the diffusion of microscopic objects (e.g., bacteria or cells such as leukocytes) and large or hydrophilic molecules into the cerebrospinal fluid (CSF). Most pharmaceutical agents cannot pass through the BBB presenting delivery challenges.

As used herein "increasing the permeability of the BBB" refers to increasing the amount or size of molecules or microscopic objects transported across the blood brain barrier, while conversely "decreasing the permeability of the blood brain barrier" refers to decreasing the amount or size of molecules or microscopic objects transported across the BBB.

Stabilizing or restoring the BBB in a subject refers to stopping or retarding the rate of increases (stabilizing) or reversing increases (restoring) in BBB permeability.

As used herein, "polypeptide" and "protein" are used interchangeably and mean proteins, protein fragments, modified proteins, amino acid sequences and synthetic amino acid sequences. As used herein, a "variant" describes a peptide or polypeptide that differs from a referenced peptide or polypeptide in amino acid sequence by insertion, deletion, or conservative substitution of amino acids, or in post-translational processing, but that retains the relevant biological activity of the referenced peptide or polypeptide.

In certain embodiments, the method may modulate the interaction between RGMa and Neogenin. The agent may be an antibody, a peptide agent, a cholesterol-lowering agent, or any combination thereof. The peptide agent may be an RGMa peptide, a Neogenin peptide, a Noggin peptide, fragment thereof, variant thereof, or any combination thereof.

The Neogenin peptide may include fragments of Neogenin, variants of Neogenin, or any combination thereof. The Neogenin peptide may include two immunoglobulin-like domains of Neogenin, fragments thereof, variants thereof, or any combination thereof. The Neogenin peptide may include three immunoglobulin-like domains of Neogenin, fragments thereof, variants thereof, or any combination thereof. The Neogenin peptide may include four immunoglobulin-like domains of Neogenin, fragments thereof, variants thereof, or any combination thereof. Four immunoglobulin-like domains of Neogenin may also be referred to herein as the 4Ig domain of Neogenin. Accordingly, the Neogenin peptide may include the 4Ig domain, fragment thereof, variant thereof, or any combination thereof.

The RGMa peptide may include fragments of RGMa, variants of RGMa, or any combination thereof. The RGMa peptide may be any fragment of RGMa that interacts with the 4Ig domain of Neogenin. The RGMa peptide may contain any secondary structure that may be required for the cis interaction to occur between RGMa and Neogenin.

The RGMa peptide sequence is publicly available and accessible at http://www.uniprot.org/uniprot/Q96B86 for *H. sapiens* and http://www.uniprot.org/uniprot/Q6PCX7 for *M. musculus*. In certain embodiments, a functional fragment of RGMa may be used, which can comprise a fragment of RGMa at least 50 amino acids in length that interacts with Neogenin. sRGMa can be prepared according to methods described in Tassew N G, Charish J, Seidah N G, Monnier P P. SKI-1 and Furin generate multiple RGMa fragments that regulate axonal growth. *Dev Cell*. 2012 Feb. 14; 22(2):391-402. doi: 10.1016/j.devce1.2011.11.022. PubMed PMID: 22340500.

Peptides that act similar to the RGMa peptide, i.e., blocking or disrupting the interaction between RGMa and Neogenin, may include a peptide from RGMc.

The RGMc peptide sequence is publicly available and is accessible using Uniprot AC/ID identifier Q6ZVN8 on the Uniprot website for *H. sapiens* and using Uniprot AC/ID identifier Q7TQ32 on the Uniprot website for *M. musculus*. In certain embodiments, a functional fragment of RGMc may be used, which can comprise a fragment of RGMc at least 50 amino acids in length that interacts with Neogenin.

The method may modulate the interaction between RGMa and Neogenin by administering the Noggin peptide to the subject. The Noggin peptide may disrupt or block the cis interaction.

The Noggin peptide may include fragments of Noggin, variants of Noggin, or any combination thereof. The Noggin peptide may include the amino acid sequence of Accession No. AAA83259.

The cholesterol-lowering agent may be, but is not limited to, methyl^-cyclodextrin (MpCD), cholesterol oxidase (CO), AY-9944, a statin, a subtisilin/kexin type 9 (PCK9) inhibitor, nystatin, filipin, proprotein convertase, BM 15.766, alkylphospholipid analogs (e.g., miltefosine, edelfosine, and perifosine), or any combination thereof.

The antibody may be directed against the RGMa peptide described above. This RGMa peptide contains any secondary structure that may be required for the cis interaction to occur between RGMa and Neogenin. Accordingly, the antibody directed against the RGMa peptide may specifically recognize and selectively bind this secondary structure.

The antibody may specifically recognize and selectively bind the 4Ig domain of Neogenin. The antibody may specifically recognize and selectively bind amino acids 1 to 383 of Accession No. AAC59662 or amino acids 1 to 417 of Accession No. AAI43272.

In certain embodiments, methods may modulate the interaction between RGMc and Neogenin. Agents for use in such methods can include RGMa, sRGMa, a functional fragment, variant or mimic thereof or an agent that stimulates RGMa production or enhances RGMa binding to Neogenin.

In other embodiments, methods as disclosed herein may be effected through gene therapy, for example, by up regulating the expression of RGMc to decrease the permeability of the BBB or by down regulating the expression of RGMa to increase the permeability of the BBB.

Multiple sclerosis is generally characterized as an immune-mediated disease in which infiltrating immune cells damage myelin resulting in a loss of mobility and morbidity. However, in a subset of patients with primary progressive multiple sclerosis (PPMS), neurodegeneration occurs in the absence of immune-involvement. Treatments that can promote regeneration of myelin and neuronal survival would be of value in treating PPMS and a number of other disorders associated with neurodegeneration. The Examples evidence that soluble RGMc can promote remyelination in vitro and in vivo and therefore can be an effective treatment option for patients with PPMS and other neurodegenerative disorders.

As used herein, the term "treatment" refers to administering a composition of the invention to effect an alteration or improvement of a disease or condition. Prevention, amelioration, and/or treatment may require administration of multiple doses at regular intervals, or prior to onset of the disease or condition to alter the course of the disease or condition. Moreover, a single agent may be used in a single individual for each of prevention, amelioration, and treatment of a condition or disease sequentially, or concurrently.

"Modulate", as used herein, refers to a stimulatory or inhibitory effect on the intracellular process of interest relative to the level or activity of such a process in the absence of a treatment as described herein.

As used herein, "pharmaceutically acceptable carrier or excipient" includes any and all solvents, dispersion media, coatings, antibacterial and antifungal agents, isotonic and absorption delaying agents, fillers and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The pharmaceutical compositions as described herein may be administered in a number of ways and, in one embodiment, the mode of administration is not particularly restricted and, for example, administration may be by inhalation or in the form of ophthalmic or otic compositions; enteral, such as orally; or parenteral, including e.g. subcutaenous, intravenous, intra-arterial or intra-muscular. In one embodiment, administration is intravenous.

Various embodiments are disclosed including:
1. A method of decreasing the permeability of the blood brain barrier in a subject comprising administering to the subject a therapeutically effective amount of Repulsive Guidance Molecule C (RGMc), soluble RGMc (sRGMc) or a functional fragment, variant or mimic thereof.
2. A method of stabilizing or restoring the blood brain barrier in a subject comprising administering to the subject a therapeutically effective amount of RGMc, sRGMc or a functional fragment, variant or mimic thereof.
3. A method of decreasing the permeability of the blood brain barrier in a subject comprising administering to the subject a therapeutically effective amount of an agent that inhibits Repulsive Guidance Molecule A (RGMa).
4. A method of stabilizing or restoring the blood brain barrier in a subject comprising administering to the subject a therapeutically effective amount of an agent that inhibits RGMa.
5. The method of embodiment 3 or 4, wherein the agent inhibits binding between RGMa and Neogenin or promotes binding between RGMc and Neogenin.
6. The method of embodiment 5, wherein the agent is an antibody, a peptide agent, a cholesterol-lowering agent, or any combination thereof.
7. The method of embodiment 6, wherein the peptide agent is a RGMc peptide, a Neogenin peptide, a Noggin peptide, fragment thereof, variant thereof, or any combination thereof.
8. The method of embodiment 3 or 4, wherein the agent is a functional fragment of RGMc of at least 50 amino acids in length that interacts with Neogenin.

9. The method of embodiment 8, wherein the functional fragment of RGMc is at least 50 amino acids in length and has a sequence comprising an amino acid sequence found in SEQ ID NO: 1 or 3.

10. The method of embodiment 7, wherein the peptide is sRGMc.

11. The method of any one of embodiments 1 to 10, wherein the method prevents or reduces immune cell infiltration into the central nervous system (CNS).

12. The method of any one of embodiments 1 to 11 for treating a disease associated with disruption of the blood brain barrier.

13. The method of any one of embodiments 1 to 12 for treating a disease or condition, wherein the disease or condition is multiple sclerosis (MS), ischemia (stroke), spinal cord injury, Alzheimer's disease, Parkinson's disease, brain cancer, epilepsy, depression, or an ocular condition, including glaucoma or retinitis pigmentosa (RP).

14. The method of embodiment 13, wherein the disease or condition is MS.

15. A method for disrupting blood brain barrier integrity in a subject, comprising administering to the subject a therapeutically effective amount of an agent that inhibits RGMc.

16. A method for disrupting blood brain barrier integrity in a subject, comprising administering to the subject a therapeutically effective amount of an agent, wherein the agent is RGMa, sRGMa, a functional fragment, variant or mimic thereof or stimulates RGMa.

17. A method for increasing the permeability of the blood brain barrier of a subject to a molecule present in the blood stream of the subject comprising co-administering to said subject an effective amount of an agent that inhibits RGMc.

18. A method for increasing the permeability of the blood brain barrier of a subject to a molecule present in the blood stream of the subject comprising co-administering to said subject a therapeutically effective amount of an agent, wherein the agent is RGMa, sRGMa, a functional fragment, variant or mimic thereof or stimulates RGMa.

19. The method of any one of embodiments 15 to 18, wherein the molecule and the agent are administered concomitantly.

20. The method of any one of embodiments 15 to 18, wherein the agent is administered prior to the molecule.

21. The method of embodiment 20, wherein the agent is administered about one day, more than one day, within about 23, 22, 21, 20, 19, 18, 17, 16, 15, 14, 13, 12, 11, 10, 9, 8, 7, 6, 5, 4, 3, 2, 1 or within one hour prior to administration of the molecule.

22. The method of any one of embodiments 15 to 21 further comprising administering a therapeutically effective amount of RGMc, sRGMc, or a functional fragment, variant or mimic thereof to the subject after administration of the molecule to decrease the permeability of the blood brain barrier.

23. The method of embodiment 22, wherein the therapeutically effective amount of RGMc, sRGMc, or a functional fragment, variant or mimic thereof is administered within 1, 2, 3, 4, 5, 6, 7, 8, 9, 10, 11, 12, 13, 14, 15, 16, 17, 18, 19, 20, 21, 22, 23 or 24 hours or is administered more than one day after administration of the molecule.

24. The method of any one of embodiments 15 to 22 further comprising administering a therapeutically effective amount of an agent that inhibits RGMa to the subject after administration of the molecule to decrease the permeability of the blood brain barrier.

25. The method of embodiment 24, wherein the therapeutically effective amount of the agent that inhibits RGMa is administered within 1, 2, 3, 4, 5, 6, 7, 8, 9, 10, 11, 12, 13, 14, 15, 16, 17, 18, 19, 20, 21, 22, 23 or 24 hours or is administered more than one day after administration of the molecule.

26. The method of embodiment 24 or 25, wherein the agent that inhibits RGMa inhibits binding between RGMa and Neogenin or promotes binding between RGMc and Neogenin.

27. The method of embodiment 26, wherein the agent is an antibody, a peptide agent, a cholesterol-lowering agent, or any combination thereof.

28. The method of embodiment 27, wherein the peptide agent is an RGMc peptide, a Neogenin peptide, a Noggin peptide, fragment thereof, variant thereof, or any combination thereof.

29. The method of any one of embodiments 15 to 28, wherein the molecule is an imaging agent.

30. The method of any one of embodiments 15 to 28, wherein the molecule is a pharmaceutical.

31. The method of embodiment 30, wherein the pharmaceutical is an anaesthetic, antipsychotic, antidepressant, an antiemetic, or an anticonvulsant.

32. The method of embodiment 30, wherein the pharmaceutical is for the treatment of a disease or condition selected from MS, ischemia (stroke), spinal cord injury, Alzheimer's disease, epilepsy, depression, or an ocular condition, including glaucoma or RP, or a movement disorder, including Parkinson's disease.

33. The method of embodiment 30, wherein the pharmaceutical is an anti-cancer drug.

34. The method of any one of embodiments 1 to 33 wherein the subject is human.

35. A method of determining the prognosis of a patient suffering from a disease or condition associated with disruption of the blood brain barrier comprising:
determining the level of sRGMc and sRGMa in a patient sample;
comparing the level of sRGMc and sRGMa in the patient sample to average levels in a population sample of patients suffering from said disease or condition, wherein a level of sRGMc below the average and a level of sRGMa above the population sample average is predictive of a higher than average severity of the disease or condition.

36. The method of embodiment 35 wherein the disease or condition is MS, ischemia (stroke), spinal cord injury, Alzheimer's disease, Parkinson's disease, brain cancer, epilepsy, depression, or an ocular condition, including glaucoma or RP.

37. The method of embodiment 35 or 36 wherein the sample is a blood sample.

38. The method of any one of embodiments 35 to 37 further comprising treating the patient by a method of any one of embodiments 1 to 14.

39. Use of a therapeutically effective amount of RGMc, sRGMc or a functional fragment, variant or mimic thereof for decreasing the permeability of the blood brain barrier in a subject.

40. Use of a therapeutically effective amount of RGMc, sRGMc or a functional fragment, variant or mimic thereof for stabilizing or restoring the blood brain barrier in a subject.

41. Use of a therapeutically effective amount of an agent that inhibits RGMa for decreasing the permeability of the blood brain barrier in a subject.
42. Use of a therapeutically effective amount of an agent that inhibits RGMa for stabilizing or restoring the blood brain barrier in a subject.
43. The use of embodiment 41 or 42, wherein the agent inhibits binding between RGMa and Neogenin.
44. The use of embodiment 43, wherein the agent is an antibody, a peptide agent, a cholesterol-lowering agent, or any combination thereof.
45. The use of embodiment 44, wherein the peptide agent is a RGMc peptide, a Neogenin peptide, a Noggin peptide, fragment thereof, variant thereof, or any combination thereof.
46. The use of embodiment 41 or 42, wherein the agent is a functional fragment of RGMc of at least 50 amino acids in length that interacts with Neogenin.
47. The use of embodiment 46, wherein the functional fragment of RGMc is at least 50 amino acids in length and has a sequence comprising an amino acid sequence found in SEQ ID NO: 1 or 3.
48. The use of embodiment 45, wherein the peptide is sRGMc.
49. The use of any one of embodiments 39 to 48, wherein the use prevents or reduces immune cell infiltration into the CNS.
50. The use of any one of embodiments 39 to 49 for treating a disease associated with disruption of the blood brain barrier.
51. The use of any one of embodiments 39 to 50 for treating a disease or condition, wherein the disease or condition is MS, ischemia (stroke), spinal cord injury, Alzheimer's disease, Parkinson's disease, brain cancer, epilepsy, depression, or an ocular condition, including glaucoma or RP.
52. The use of embodiment 51, wherein the disease or condition is MS.
53. Use of a therapeutically effective amount of an agent that inhibits RGMc for disrupting blood brain barrier integrity in a subject.
54. Use of a therapeutically effective amount of an agent, wherein the agent is RGMa, sRGMa, a functional fragment, variant or mimic thereof or stimulates RGMa, for disrupting blood brain barrier integrity in a subject.
55. Use of a therapeutically effective amount of an agent that inhibits RGMc for increasing the permeability of the blood brain barrier of a subject to a molecule present in the blood stream of the subject.
56. Use of a therapeutically effective amount of an agent, wherein the agent is RGMa, sRGMa, a functional fragment, variant or mimic thereof or stimulates RGMa, for increasing the permeability of the blood brain barrier of a subject to a molecule present in the blood stream of the subject.
57. The use of any one of embodiments 53 to 56, wherein the molecule and the agent are administered concomitantly.
58. The use of any one of embodiments 53 to 56, wherein the agent is administered prior to the molecule.
59. The use of embodiment 58, wherein the agent is administered about one day, more than one day, within about 23, 22, 21, 20, 19, 18, 17, 16, 15, 14, 13, 12, 11, 10, 9, 8, 7, 6, 5, 4, 3, 2, 1 or within one hour prior to administration of the molecule.
60. The use of any one of embodiments 53 to 59 further comprising administering a therapeutically effective amount of RGMc, sRGMc, or a functional fragment, variant or mimic thereof to the subject after administration of the molecule to decrease the permeability of the blood brain barrier.
61. The use of embodiment 60, wherein the therapeutically effective amount of RGMc, sRGMc, or a functional fragment, variant or mimic thereof is administered within 1, 2, 3, 4, 5, 6, 7, 8, 9, 10, 11, 12, 13, 14, 15, 16, 17, 18, 19, 20, 21, 22, 23 or 24 hours or is administered more than one day after administration of the molecule.
62. The use of any one of embodiments 53 to 59 further comprising administering a therapeutically effective amount of an agent that inhibits RGMa to the subject after administration of the molecule to decrease the permeability of the blood brain barrier.
63. The use of embodiment 62, wherein the therapeutically effective amount of the agent that inhibits RGMa is administered within 1, 2, 3, 4, 5, 6, 7, 8, 9, 10, 11, 12, 13, 14, 15, 16, 17, 18, 19, 20, 21, 22, 23 or 24 hours or is administered more than one day after administration of the molecule.
64. The use of embodiment 62 or 63, wherein the agent inhibits binding between RGMa and Neogenin or promotes binding between RGMc and Neogenin.
65. The use of embodiment 64, wherein the agent is an antibody, a peptide agent, a cholesterol-lowering agent, or any combination thereof.
66. The use of embodiment 65, wherein the peptide agent is an RGMc peptide, a Neogenin peptide, a Noggin peptide, fragment thereof, variant thereof, or any combination thereof.
67. The use of any one of embodiments 53 to 66, wherein the molecule is an imaging agent.
68. The use of any one of embodiments 53 to 66, wherein the molecule is a pharmaceutical.
69. The use of embodiment 68, wherein the pharmaceutical is an anaesthetic, antipsychotic, antidepressant, an antiemetic, or an anticonvulsant.
70. The use of embodiment 68, wherein the pharmaceutical is for the treatment of a disease or condition selected from MS, ischemia (stroke), spinal cord injury, Alzheimer's disease, epilepsy, depression, or an ocular condition, including glaucoma or RP, or a movement disorder, including Parkinson's disease.
71. The use of embodiment 68, wherein the pharmaceutical is an anti-cancer drug.
72. The use of any one of embodiments 39 to 71 wherein the subject is human.
73. Use of RGMc, sRGMc, or a functional fragment, variant or mimic thereof in the manufacture of a medicament for decreasing the permeability of the blood brain barrier in a subject.
74. Use of RGMc, sRGMc, or a functional fragment, variant or mimic thereof in the manufacture of a medicament for stabilizing or restoring the blood brain barrier in a subject.
75. Use of an agent that inhibits RGMa in the manufacture of a medicament for decreasing the permeability of the blood brain barrier in a subject.
76. Use of an agent that inhibits RGMa in the manufacture of a medicament for stabilizing or restoring the blood brain barrier in a subject.
77. The use of embodiment 75 or 76, wherein the agent inhibits binding between RGMa and Neogenin or promotes binding between RGMc and Neogenin.
78. The use of embodiment 77, wherein the agent is an antibody, a peptide agent, a cholesterol-lowering agent, or any combination thereof.

79. The use of embodiment 78, wherein the peptide agent is a RGMc peptide, a Neogenin peptide, a Noggin peptide, fragment thereof, variant thereof, or any combination thereof.
80. The use of embodiment 75 or 76, wherein the agent is a functional fragment of RGMc of at least 50 amino acids in length that interacts with Neogenin.
81. The use of embodiment 80, wherein the functional fragment of RGMc is at least 50 amino acids in length and has a sequence comprising an amino acid sequence found in SEQ ID NO: 1 or 3.
82. The use of embodiment 79, wherein the peptide is sRGMc.
83. The use of any one of embodiments 73 to 82, wherein the use prevents or reduces immune cell infiltration into the CNS.
84. The use of any one of embodiments 73 to 83 for treating a disease associated with disruption of the blood brain barrier.
85. The use of any one of embodiments 73 to 84 for treating a disease or condition, wherein the disease or condition is MS, ischemia (stroke), spinal cord injury, Alzheimer's disease, Parkinson's disease, brain cancer, epilepsy, depression, or an ocular condition, including glaucoma or RP.
86. The use of embodiment 85, wherein the disease or condition is MS.
87. Use of an agent that inhibits RGMc in the manufacture of a medicament for disrupting blood brain barrier integrity in a subject.
88. Use of an agent, wherein the agent is RGMa, sRGMa, a functional fragment, variant or mimic thereof or stimulates RGMa, in the manufacture of a medicament for disrupting blood brain barrier integrity in a subject.
89. Use of an agent that inhibits RGMc in the manufacture of a medicament for increasing the permeability of the blood brain barrier of a subject to a molecule present in the blood stream of the subject.
90. Use of an agent, wherein the agent is RGMa, sRGMa, a functional fragment, variant or mimic thereof or stimulates RGMa, in the manufacture of a medicament for increasing the permeability of the blood brain barrier of a subject to a molecule present in the blood stream of the subject.
91. The use of any one of embodiments 87 to 90, wherein the molecule and the agent are for administration concomitantly.
92. The use of any one of embodiments 87 to 90, wherein the agent is for administration prior to the molecule.
93. The use of embodiment 92, wherein the agent is for administration about one day, more than one day, within about 23, 22, 21, 20, 19, 18, 17, 16, 15, 14, 13, 12, 11, 10, 9, 8, 7, 6, 5, 4, 3, 2, 1 or within one hour prior to administration of the molecule.
94. The use of any one of embodiments 87 to 93 in combination with a therapeutically effective amount of RGMc, sRGMc, or a functional fragment, variant or mimic thereof for administration to the subject after administration of the molecule to decrease the permeability of the blood brain barrier.
95. The use of embodiment 94, wherein the therapeutically effective amount of RGMc, sRGMc, or a functional fragment, variant or mimic thereof is for administration within 1, 2, 3, 4, 5, 6, 7, 8, 9, 10, 11, 12, 13, 14, 15, 16, 17, 18, 19, 20, 21, 22, 23 or 24 hours or is for administration more than one day after administration of the molecule.
96. The use of any one of embodiments 87 to 93 in combination with a therapeutically effective amount of an agent that inhibits RGMa for administration to the subject after administration of the molecule to decrease the permeability of the blood brain barrier.
97. The use of embodiment 96, wherein the therapeutically effective amount of the agent that inhibits RGMa is for administration within 1, 2, 3, 4, 5, 6, 7, 8, 9, 10, 11, 12, 13, 14, 15, 16, 17, 18, 19, 20, 21, 22, 23 or 24 hours or is for administration more than one day after administration of the molecule.
98. The use of embodiment 96 or 97, wherein the agent inhibits binding between RGMa and Neogenin or promotes binding between RGMc and Neogenin.
99. The use of embodiment 98, wherein the agent is an antibody, a peptide agent, a cholesterol-lowering agent, or any combination thereof.
100. The use of embodiment 99, wherein the peptide agent is a RGMc peptide, a Neogenin peptide, a Noggin peptide, fragment thereof, variant thereof, or any combination thereof.
101. The use of any one of embodiments 87 to 100, wherein the molecule is an imaging agent.
102. The use of any one of embodiments 87 or 100, wherein the molecule is a pharmaceutical.
103. The use of embodiment 102, wherein the pharmaceutical is an anaesthetic, antipsychotic, antidepressant, an antiemetic, or an anticonvulsant.
104. The use of embodiment 102, wherein the pharmaceutical is for the treatment of a disease or condition selected from MS, ischemia (stroke), spinal cord injury, Alzheimer's disease, epilepsy, depression, or an ocular condition, including glaucoma or RP or a movement disorder, including Parkinson's disease.
105. The use of embodiment 102, wherein the pharmaceutical is an anti-cancer drug.
106. The use of any one of embodiments 73 to 105 wherein the subject is human.
107. A pharmaceutical composition comprising RGMc, sRGMc or a functional fragment, variant or mimic thereof and a pharmaceutically acceptable carrier or excipient for decreasing the permeability of the blood brain barrier in a subject.
108. A pharmaceutical composition comprising RGMc, sRGMc or a functional fragment, variant or mimic thereof and a pharmaceutically acceptable carrier or excipient for stabilizing or restoring the blood brain barrier in a subject.
109. A pharmaceutical composition comprising an agent that inhibits RGMa and a pharmaceutically acceptable carrier or excipient for decreasing the permeability of the blood brain barrier in a subject.
110. A pharmaceutical composition comprising an agent that inhibits RGMa and a pharmaceutically acceptable carrier or excipient for stabilizing or restoring the blood brain barrier in a subject.
111. The pharmaceutical composition of embodiment 109 or 110, wherein the agent inhibits binding between RGMa and Neogenin or promotes binding between RGMc and Neogenin.
112. The pharmaceutical composition of embodiment 111, wherein the agent is an antibody, a peptide agent, a cholesterol-lowering agent, or any combination thereof.
113. The pharmaceutical composition of embodiment 112, wherein the peptide agent is a RGMc peptide, a Neogenin peptide, a Noggin peptide, fragment thereof, variant thereof, or any combination thereof.

114. The pharmaceutical composition of embodiment 109 or 110, wherein the agent is a functional fragment of RGMc of at least 50 amino acids in length that interacts with Neogenin.
115. The pharmaceutical composition of embodiment 114, wherein the functional fragment of RGMc is at least 50 amino acids in length and has a sequence comprising an amino acid sequence found in SEQ ID NO: 1 or 3.
116. The pharmaceutical composition of embodiment 113, wherein the peptide is sRGMc.
117. The pharmaceutical composition of any one of embodiments 107 to 116, wherein the pharmaceutical composition prevents or reduces immune cell infiltration into the CNS.
118. The pharmaceutical composition of any one of embodiments 107 to 117 for treating a disease associated with disruption of the blood brain barrier.
119. The pharmaceutical composition of any one of embodiments 107 to 118 for treating a disease or condition, wherein the disease or condition is MS, ischemia (stroke), spinal cord injury, Alzheimer's disease, Parkinson's disease, brain cancer, epilepsy, depression, or an ocular condition, including glaucoma or RP.
120. The pharmaceutical composition of embodiment 119, wherein the disease or condition is MS.
121. A pharmaceutical composition comprising an agent that inhibits RGMc and a pharmaceutically acceptable carrier or excipient for disrupting blood brain barrier integrity in a subject.
122. A pharmaceutical composition comprising an agent, wherein the agent is RGMa, sRGMa, a functional fragment, variant or mimic thereof or stimulates RGMa and a pharmaceutically acceptable carrier or excipient, for disrupting blood brain barrier integrity in a subject.
123. A pharmaceutical composition comprising an agent that inhibits RGMc and a pharmaceutically acceptable carrier or excipient, for increasing the permeability of the blood brain barrier of a subject to a molecule present in the blood stream of the subject.
124. A pharmaceutical composition comprising an agent, wherein the agent is RGMa, sRGMa, a functional fragment, variant or mimic thereof or stimulates RGMa and a pharmaceutically acceptable carrier or excipient for increasing the permeability of the blood brain barrier of a subject to a molecule present in the blood stream of the subject.
125. The pharmaceutical composition of any one of embodiments 121 to 124, wherein the molecule and the agent are for administration concomitantly.
126. The pharmaceutical composition of any one of embodiments 121 to 124, wherein the agent is for administration prior to the molecule.
127. The pharmaceutical composition of embodiment 126, wherein the agent is for administration about one day, more than one day, within about 23, 22, 21, 20, 19, 18, 17, 16, 15, 14, 13, 12, 11, 10, 9, 8, 7, 6, 5, 4, 3, 2, 1 or within one hour prior to administration of the molecule.
128. The pharmaceutical composition of any one of embodiments 121 to 127 in combination with a further pharmaceutical composition comprising a therapeutically effective amount of RGMc, sRGMc, or a functional fragment, variant or mimic thereof and a pharmaceutically acceptable carrier or excipient for administration to the subject after administration of the molecule to decrease the permeability of the blood brain barrier.
129. The pharmaceutical composition of embodiment 128, wherein said further pharmaceutical composition is for administration within 1, 2, 3, 4, 5, 6, 7, 8, 9, 10, 11, 12, 13, 14, 15, 16, 17, 18, 19, 20, 21, 22, 23 or 24 hours or is for administration more than one day after administration of the molecule.
130. The pharmaceutical composition of any one of embodiments 121 to 127 in combination with a further pharmaceutical composition comprising a therapeutically effective amount of an agent that inhibits RGMa and a pharmaceutically acceptable carrier or excipient for administration to the subject after administration of the molecule to decrease the permeability of the blood brain barrier.
131. The pharmaceutical composition of embodiment 130, wherein the further pharmaceutical composition is for administration within 1, 2, 3, 4, 5, 6, 7, 8, 9, 10, 11, 12, 13, 14, 15, 16, 17, 18, 19, 20, 21, 22, 23 or 24 hours or is for administration more than one day after administration of the molecule.
132. The pharmaceutical composition of embodiment 130 or 131, wherein the agent inhibits binding between RGMa and Neogenin or promotes binding between RGMc and Neogenin.
133. The pharmaceutical composition of embodiment 132, wherein the agent is an antibody, a peptide agent, a cholesterol-lowering agent, or any combination thereof.
134. The pharmaceutical composition of embodiment 133, wherein the peptide agent is an RGMc peptide, a Neogenin peptide, a Noggin peptide, fragment thereof, variant thereof, or any combination thereof.
135. The pharmaceutical composition of any one of embodiments 121 to 134, wherein the molecule is an imaging agent.
136. The pharmaceutical composition of any one of embodiments 121 or 134, wherein the molecule is a pharmaceutical.
137. The pharmaceutical composition of embodiment 136, wherein the pharmaceutical is an anaesthetic, antipsychotic, antidepressant, an antiemetic, or an anticonvulsant.
138. The pharmaceutical composition of embodiment 136, wherein the pharmaceutical is for the treatment of a disease or condition selected from MS, ischemia (stroke), spinal cord injury, Alzheimer's disease, epilepsy, depression, or an ocular condition, including glaucoma or RP or a movement disorder, including Parkinson's disease.
139. The pharmaceutical composition of embodiment 136, wherein the pharmaceutical is an anti-cancer drug.
140. The pharmaceutical composition of any one of embodiments 107 to 139 wherein the subject is human.
141. A method of promoting re-myelination in a subject comprising administering to the subject a therapeutically effective amount of Repulsive Guidance Molecule C (RGMc), soluble RGMc (sRGMc) or a functional fragment, variant or mimic thereof.
142. A method of preventing de-myelination in a subject comprising administering to the subject a therapeutically effective amount of Repulsive Guidance Molecule C (RGMc), soluble RGMc (sRGMc) or a functional fragment, variant or mimic thereof.
143. The method of embodiment 141 or embodiment 142, in which the subject has primary progressive multiple sclerosis.
144. Use of a therapeutically effective amount of RGMc, sRGMc or a functional fragment, variant or mimic thereof for promoting re-myelination in a subject.

145. Use of a therapeutically effective amount of RGMc, sRGMc or a functional fragment, variant or mimic thereof for preventing de-myelination in a subject.
146. The use of embodiment 144 or embodiment 145, in which the subject has primary progressive multiple sclerosis.
147. A pharmaceutical composition comprising RGMc, sRGMc or a functional fragment, variant or mimic thereof and a pharmaceutically acceptable carrier or excipient for promoting re-myelination in a subject.
148. A pharmaceutical composition comprising RGMc, sRGMc or a functional fragment, variant or mimic thereof and a pharmaceutically acceptable carrier or excipient for preventing de-myelination in a subject.
149. The composition of embodiment 147 or embodiment 148 for the treatment of MS optionally primary progressive MS, ischemia (stroke), spinal cord injury, Alzheimer's disease, Parkinson's disease, brain cancer, epilepsy, depression, or an ocular condition including optic neuritis, glaucoma or RP.

EXAMPLES

Example 1

The documents referenced herein are incorporated by reference where permitted, however, it should be appreciated that any patent, publication, or other disclosure material, in whole or in part, that is incorporated by reference herein is incorporated only to the extent that the incorporated material does not conflict with definitions, statements, or other disclosure material set forth in this disclosure. As such, and to the extent necessary, the disclosure as explicitly set forth herein supersedes any conflicting material incorporated herein by reference.

Materials and Methods for Examples 2-10

Provided herein are in Example 1 are materials and methods that were used in the experiments described below in Examples 2-10

Experimental Autoimmune Encephalomyelitis Mouse Model.

Figure 2:
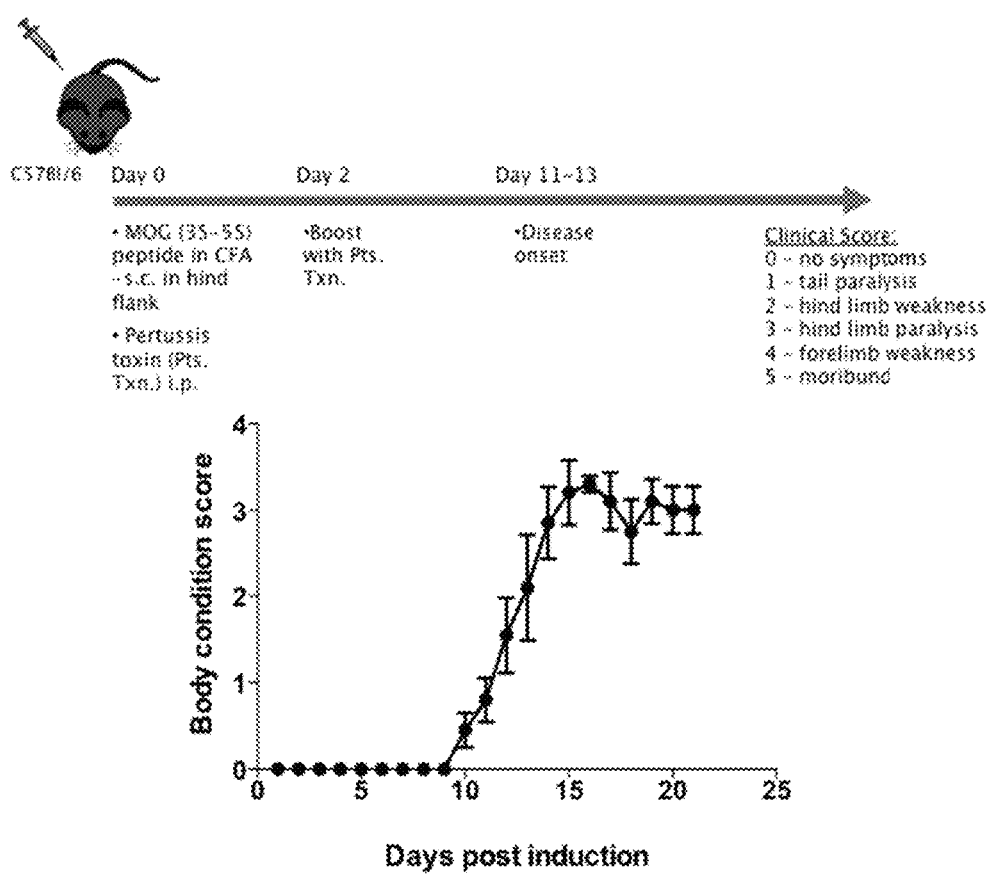
FIG. 2—FIG. 2 shows generation of the experimental autoimmune encephalomyelitis (EAE) model. As seen on the timeline, an initial injection of MOG (35-55), in an emulsion with CFA, is injected s.c. in the hind flank of mice. Subsequently mice are injected with an i.p. injection of pertussis toxin at day 0 and day 2-post-induction of EAE. The typical initial symptoms arise at days 10-12 following induction. This model leads to an acute ascending paralysis (tail>forelimb), which typically progresses and eventually plateaus by day 20-22 post induction.

Six to eight week-old female C57BL/6 mice (Harlan laboratories) or 129S-Hfe2$^{tm1Nca}$/J (stock. No. 017788, Jackson Laboratories) and their wild type control 129S1/SvImJ (stock. No. 002448, Jackson Laboratories) were immunized by subcutaneous (s.c.) injection of 50 µg myelin oligodendrocyte glycoprotein (MOG) amino acids 35-55 (Sheldon Biotech, Montreal, QC) in incomplete Freund's adjuvant (Sigma) supplemented with 1 mg of *Mycobacterium tuberculosis* (CFA) (Difco, Detroit, Mich.). 400 ng of pertussis toxin (List Biologicals) was administered intraperitoneally (i.p.) on days 0 and 2 post-immunization (FIG. 2). The animals were scored behaviorally using a well-established body condition score (BCS) using the following scale: 0, no paralysis; 1, loss of tail-tone reflex; 2, loss of righting reflex; 3, complete hind limb paralysis; 4, forelimb weakness; 5, moribund or dead. Intermediate scores (0.5) were given to animals that did not meet the upper scale of paralysis. A mean cumulative score was obtained from two reading per day at 12 h intervals.

Administration of sRGMc and sRGMa.

To investigate the role of sRGMc, 20 mM of either purified sRGMc, sRGMa, or vehicle (PBS) were administered to mice induced with EAE by intra-venous (i.v.) injection at days 3, 6 and 9 or intra-peritoneally every 3d for the duration of the disease. To elucidate the physiological interaction between sRGMc and sRGMa in the EAE model, a combination of sRGMc (20 mM) in conjunction with 2 volumes of sRGMa (40 mM) was administered to EAE mice intra-peritoneally every 3d until the time of sacrifice.

sRGMc cloning in the Psectag2B Vector.

Membrane-bound full-length mouse RGMc was used for further cloning. The full-length annotated mouse sequence including the GPI-anchor can be found using Uniprot AC/ID identifier Q7TQ32 on the Uniprot website. The full-length annotated sequence in *Homo Sapiens* including the GPI-anchor can be found using Uniprot AC/ID identifier Q6ZVN8 on the Uniprot website. To replicate endogenous soluble RGMc, present in serum, the GPI anchor sequence of RGMc was removed, generating a truncated form of RGMc (sRGMc). The resulting protein is targeted to the membrane using the Psectag2B signaling sequence and is released out of the cell, into the medium, as a soluble protein (human and mouse soluble proteins are provided as SEQ ID NOs: 1 and 3, respectively, and their coding sequences as SEQ ID NOs: 2 and 4, respectively). sRGMC was generated using the following primers:

Forward primer: 5' cttggtacccatcatcatcatcatcagtgcaagatcctccgctg 3' (SEQ ID NO: 5)

Reverse primer: 5' gcgtctagacactcgagcgtcgagctgcccagctgtctgtc 3' (SEQ ID NO: 6)

Polymerase Chain Reaction (PCR) was performed using TAQ polymerase to generate an RGMc DNA fragment of 1175 base pairs in length containing a KpnI restriction site (5' end) and an EcorI site (3'end) (New England Biolabs). The PCR product was then purified and ligated into a T-vector which was subsequently digested with the above-mentioned restriction enzymes, inserted into a pSecTag2B expression vector (Invitrogen, Thermo Fisher Scientific) and the construct was sequenced to ensure the protein was in the correct frame. The pSecTag 2B vector contains a T7 promoter binding site and an Igk lead signal peptide for the specific targeting of the inserted sRGMc sequence to the cellular membrane.

Cell Culture.

Human Embryonic Kidney cells (HEK293) and murine brain-derived Endothelial cells (b.end3) were cultured at 37° C. and 5% $CO_2$. Cells were maintained in Dulbecco's Modified Eagle Medium (Sigma-Aldrich or ATCC) containing 10% fetal bovine serum (FBS) (Gibco) and 1% penicillin/streptomycin (p/s) (Gibco).

sRGMc Expression.

sRGMc pSecTag2b plasmid was transiently transfected into HEK293 cells using polyethylenimine (PEI, Polysciences Inc.). Cells were transfected with 9 µg of DNA for 6 h at 37° C. and 5% $CO_2$, washed using Dulbecco-Phosphate Buffered Saline (D-PBS, Sigma-Aldrich) and media with reduced serum (OPTI-MEM, Gibco) was then added to the cells and incubated at 37° C. and 5% $CO_2$ for 48 h. The media was then harvested, centrifuged at 300 rcf for 5 min and supernatants were extracted and sRGMc was visualized by SDS-PAGE.

Neogenin Expression.

To verify Neogenin expression in endothelial cells, b.End3 cell membranes were prepared as previously described. [Tassew N et al. (2014). Modifying Lipid Rafts Promotes Regeneration and Functional Recovery. *Cell Rep* 8:1146-1159] Briefly, cells were washed with chilled PBS, homogenized on ice using G27.5/G30 needles in homogenizing buffer (10 mM HEPES, 25 mM KCl, 5 mM $MgCl_2$, pH 7.3) with protease inhibitors. The homogenate was overlaid on a 50% and 5% sucrose gradient, centrifuged at 28,000 rpm in SW 60Ti rotor (Beckman) for 10 min at 4° C. The membranes were then extracted using a 21G needle and centrifuged at 13,000 rpm for 10 min at 4° C. The supernatant was removed and the membrane pellets were re-suspended to the appropriate concentration in PBS. The membranes were then prepared for Western Blotting analysis.

sRGMc and sRGMa Proteins.

Mouse RGMa and RGMc were cloned with His tag replacing the GPI-anchor to allow secretion and subsequent purification of the proteins. HEK293 cells (95% confluent) grown in antibiotic-free media were transfected with sRGMc or sRGMa using Lipofectamine 2000 (Invitrogen) according to manufacturer's instructions. At 24 h post-transfection, cells were passaged at a 1:3 ratio (37° C.) and at 48 h post-transfection, selection media (10% FBS, 1% p/s, 250 µg/mL Zeocin) was added to the cells. Each specific colony was then picked and expanded. The expression of sRGMc and sRGMa was verified using western blot analysis. Media from transfected cells were collected 48 h later and purified on Ni-NTA beads according to manufacturer's protocols (Qiagen). Proteins were dialyzed in PBS before being used in all assays.

Western Blot Analysis.

Cell lysates from mouse serum, cells, conditioned medium, and reduced-serum medium were incubated for 72 h and lysed using RIPA buffer and protease inhibitor cocktail. Western blots were performed as previously described. [Tassew N et al. (2014). Modifying Lipid Rafts Promotes Regeneration and Functional Recovery. *Cell Rep* 8:1146-1159] and probed with primary antibodies (anti-RGMa AF-2459, R&D; anti-RGMc, AF-3636, R&D; anti-transferrin Sc-3-159, Santa Cruz; anti-Neogenin Sc-15337, Santa Cruz). Donkey anti-mouse, goat anti-mouse, donkey anti-goat secondary IRDye 800CW antibodies were used as appropriate (LI-COR BioSciences) for 1 h at room temperature. Coomassie staining was performed to ascertain equal total protein loading for each condition.

In Vitro Competition Binding Assay.

Using a 96-well microtiter plate (Corning), wells coated with 100 µl (10 µg/mL) of Poly-L-Lysine (Sigma-Aldrich) incubated at 4° C. overnight were then washed 3× with 100 µl of PBST (+0.02% Tween-20). His-tagged proteins (2.5 µg/mL of extracellular-Neogenin or sRGMa or sRGMc) were then coated onto each well for 1 h at 37° C., washed 3× with 100 µl PBST, blocked with 300 µl of 3% BSA in PBST for 1 h at 37° C. and 50 µl (1.0 µg/mL) Alkaline Phosphatase (AP)-tagged proteins (extracellular Neogenin or RGMa or RGMc) in 1% BSA+PBST were added to each well and incubated at 37° C. for 1 h. Each well was washed 3× with 100 µl PBST and equilibrated with AP developing buffer (100 mM $NaHCO_3$, 1 mM $MgCl_2$). The reaction was initiated using AP developing buffer supplemented with p-nitrophenyl phosphate (pNPP, Sigma-Aldrich) and then stopped following color development by adding 50 µl (0.1M) NaOH. The absorbance of each reaction was measured using a microplate autoreader (BioTek EL311 Auto-Reader) at 405 nm.

Enzyme-Linked Immunoabsorbant Assay (ELISA).

Blood collected from the saphenous veins of mice induced with EAE at 0, 5, 10, 18 and 30 days in Microvette® CB300 capillary tubes (Starstedt) was spun down at 2000 rcf for 10 min and stored at −80° C. sRGMa and sRGMc in the sera were detected using ELISA kits for sRGMa (MRG-MAO, R&D) and sRGMc (MRGMCO, R&D) according to manufacturer's instructions.

To measure the expression of endogenous RGMc in mouse serum, prior to and 18 days post-EAE induction, blood was extracted from the saphenous vein of mice and allowed to coagulate for 2 h at room temperature. The blood samples were then centrifuged at 2000 rcf for 20 min and subsequently stored at −80° C. A 0.75 mm 4% stacking/12% SDS gel was run as previously described. The transferred nitrocellulose membrane was blocked using 5% bovine serum albumin (BSA) (BioShop) in PBS. Blots were scanned and visualized using an Odyssey infrared imaging system. Protein levels were determined using densitometric analysis. RGMc protein levels were then normalized to their corresponding transferrin protein levels (loading control).

Immune Cells Preparation.

Mice were euthanized at day 10 post-induction of EAE. Freshly isolated spleens and draining caudal lymph nodes (LN) were pressed using a syringe plunger through a 70 µm cell strainers and washed twice using 2 mL of 2% FBS in complete RPMI-1640 medium (Invitrogen) supplemented with 243 Mercaptoethanol, L-glutamine, p/s, and non-essential amino acids. Single-cell suspensions were lysed with 7 mL of red blood cell (RBC) lysing buffer (Life Technologies) and centrifuged at 700 rcf for 5 mins. After washing three times with 2% RPMI-1640 medium, cells were counted and cultured as described below or were subjected to cell surface staining.

Flow Cytometry (FACS) and Intracellular Cytokine Analysis.

The expression of cell-surface markers and cytokine expression on splenocytes and LN cells were characterized by flow cytometry. For analysis of naïve cells, $5 \times 10^5$ RBC depleted splenocytes and LN cells were plated in 96-well V-bottom plates (Starstedt) and blocked with 50 µl of 1% mouse IgG in 2% FBS PBS supplemented with azide ($PFN_3$) for 20 min at 4° C. Cells were then stained with the following primary conjugated antibodies from BioLegend for 30 min on ice: CD5 (53-7.3), CD3 (145-2C11), CD4 (GK1.5), CD8 (53-6.7), CD19 (6D5), CD11b (M1/70), CD11c (N418), CD80 (16-10A1), CD86 (GL-1), CD44 (IM7), MHCII (M5/114.15.12), CD62L (MEL-14), ICAM-1/CD54 (3E2), IL-17A (TC11-18H10.41), IFN-γ (XMG1.2). All antibodies were re-suspended in $PFN_3$. When required, cells were washed twice with 100 µl of $PFN_3$ and stained with secondary SA-APC, SA-APC-Cy7, SA-PeCy7, or SA-Percp-Cy5.5 for 30 min on ice. Cells were then washed twice with $PFN_3$ and re-suspended in a $PFN_3$ solution containing propidium iodide (PI) before proceeding to FACS analysis.

To examine intracellular cytokine production, $0.5 \times 10^6$ RBC-depleted splenocytes and LN cells were plated on 96-well flat bottom plates (BD Biosciences) in 10% FBS in complete RPMI-1640 in the presence of 0.5 µg/mL phorbol 12-myrisate 13-acetate (PMA), 0.5 µg/mL Ionomycin, and Golgistop (BD Biosciences) for 4 h. Cells were subsequently washed in PBS and stained with Near-Infrared Live Dead (Life Technologies) as described in the manufacturer's protocol. Cells were then washed twice in $PFN_3$ and stained for cell surface markers as described previously. Cells were then fixed with 100 µl of Cytofix/Cytoperm solution as per manufacturer's protocol. For intracellular staining, cells were then stained with anti-IL-17A, and anti-IFN-γ for 30 min on ice, washed twice, and re-suspended in $PFN_3$ before proceeding to FACS acquisition. Nonspecific background staining was determined by using fluorochrome-matched isotype antibodies and fluorescence minus one control. Samples were acquired in a BD LSRII or FACS CantoII cytometer (BD Biosciences). For each experiment, at least 100,000 live events were acquired and analyzed using Flowjo software (Tree Star Inc.).

MOG-Specific Cytokine Expression and Proliferation.

Mice were sacrificed on day 10 post-induction and single cells suspension of splenocytes were harvested as described above. Cells ($1\times10^6$) were cultured in 10% FBS RPMI-1640 in the presence of 0 µg/mL, 30 µg/mL, or 100 µg/mL of MOG peptide for 15 h. Cells were then treated with GolgiStop (BD Biosciences) and incubated an additional 3 h and were subsequently stained.

Cytokine Analysis.

Briefly, $2\times10^6$ splenocytes were re-suspended in 1 mL of 10% FBS RPMI-1640 medium and incubated in 24-well plates (BD Biosciences) with 0 or 30 µg/mL MOG for 72 h (37° C., 5% $CO_2$). Plates were centrifuged at 1800 rpm for 5 min and the media was then harvested and stored at −80 C until analysis. Cytokine secretion of IL-17a, IL-6, TNF-α, and IFN-γ were assessed using the BD cytometric Bead Array (CBA) (BD Biosciences) according to the manufacturer's guidelines. Splenocyte proliferation was determined using CellTrace™ CFSE Cell Proliferation Kit for flow cytometry (Life Technologies) according to manufacturer's instructions. Briefly, $1\times10^6$ cells were suspended in warm PBS/0.1% BSA and stained with CFSE solution at a final concentration of 5 µM and incubated at 37° C. for 10 min. The staining was quenched using 5 volumes of ice-cold culture media, incubated for 5 min on ice, centrifuged at 700 rcf for 5 min, washed twice using culture medium, and re-suspended in 10% FBS complete RPMI-1640. Cells were then cultured in 0 µg/mL or 30 µg/mL of MOG(35-55) peptide for 72 h at 37° C., 5% $CO_2$. Cells were then harvested, washed, and stained with anti-CD3, -CD4, -CD5. Proliferation was analyzed by flow cytometry following staining in the presence of PI.

Immunohistochemistry.

At 2 weeks post-induction of EAE, mice were sacrificed and trans-cardially perfused with 20 mL PBS followed by 20 mL 4% paraformaldehyde in PBS (PFA) (Electron Microscopy Sciences). Spinal cords were isolated and post-fixed with 4% PFA overnight at 4° C., washed 3× with PBS and soaked in 30% sucrose in PBS for 48 h. Tissues were then embedded in Optimal Cutting Temperature (OCT) compound. Frozen sections of spinal cords were cut at 10-30 µm with a cryostat, mounted on gelatinized slides, dried for 2 h and stored at −80° C. Sections were then re-hydrated in PBS for 5 min and permeabilized with PBST (0.3% Triton X-100 in PBS) for 5 min. The tissues were then blocked (PBS, 0.3% Triton X-100, 3% FBS) for 1 h at room temperature and incubated with the following primary antibodies overnight at 4° C. in a humidified chamber: anti-CD3 (145-2C11, BioLegend); CD11b (M1/70, BioLegend); B220 (RA3-6B2, BioLegend), DAPI (MMS-435P, Sigma), Fibrinogen (D9542, Innovative Research).

Histological Staining.

At day 18 post-EAE induction, mice were trans-cardially perfused with 20 mL PBS followed by 20 mL 4% paraformaldehyde in PBS (PFA) (Electron Microscopy Sciences) and 30 µm spinal cord cryosections were stained. The slides were washed in PBS for 3 min, followed by a 30 s wash in 50% ethanol (EtOH) and incubated overnight in Luxol Fast Blue (LFB) at 60° C. The sections were washed in 95% EtOH for 5 min, distilled water for 5 min prior to de-staining with $LiCO_2$ for 10 min, and were then washed in 70% EtOH for 30 s, 5 min in MilliQ $H_2O$, and sections were immersed in Harris Hematoxylin (Sigma-Aldrich) for 20 min and were rinsed in warm water to remove excess stain. Samples were dehydrated in 95% EtOH, immersed in alcoholic eosin Y (Sigma-Aldrich) for 15 s, dehydrated twice in 95% EtOH for 5 min, 100% EtOH for 5 min and xylene for 5 min. Slides were mounted with Permount (Fisher Scientific) and air-dried overnight at room temperature. Luxol Fast Blue (LFB) staining was quantified using relative staining intensity using Image J software. All intensities were normalized to a sham mouse spinal cord.

Cellular infiltration was quantified using an inflammatory index: 0, no inflammation; 1, cellular infiltration only in the perivascular areas and meninges; 2, mild cellular infiltration in the parenchyma (<10 cells); 3, moderate cellular infiltration in the parenchyma (10-49 cells); 4, moderate cellular infiltration in the parenchyma (50-99 cells); and 5, severe cellular infiltration in parenchyma (>100 cells).

In Vitro BBB Permeability.

b.End3 endothelial cells were used to generate an in vitro model of the human EC barrier lining the choroid plexus. Briefly, b.end3 cells were plated on polyethylene-coated 0.4 µm pore size Boyden chambers (Corning) at a density of $2\times10^5$ cells per well in DMEM, and were allowed to grow for 72 h to reach confluency (verified using crystal violet staining). After 72 h, cells were serum starved for 6 h and pre-treated for 4 h with 10 µg/mL sRGMc, 10 µg/mL C3 Transferase or 10 µM Y27632. RGMa was then added to the wells for 18 h. The transwells were then transferred to a new plate containing 500 µl of HBSS and 200 µl 4-KDa Dextran-FITC (25 mg/ml; Sigma-Aldrich) was added to the upper chambers. Tracer diffusion across the EC monolayer was assessed in 30 min intervals for a period of 1.5 h. FITC signal, which represented the amount of extravasation through the monolayer was analyzed with using a microplate reader.

In Vivo BBB Permeability.

To establish the role of RGMc on BBB permeability, 6-8 week old C57Bl/6 female mice induced with EAE and treated with sRGMc or vehicle (n=6 animals per group) were anesthetized 18 days post induction and trans-cardially perfused with 20 mL PBS followed by 20 mL 4% paraformaldehyde in PBS (PFA) (Electron Microscopy Sciences). Spinal cords were cryo-sectioned at 10 µm thickness and stored at −80° C. The sections were stained for Fibrinogen (Innovative Research); CD31 (Invitrogen); and DAPI (Sigma-Aldrich). All images were obtained using a BX61 confocal microscope (Olympus). CellSens software was used for quantification of cell area and pixel intensity. The area (number of pixels) and fluorescent intensity (mean pixel intensity) of the extravasation markers were measured using CellSens software (Olympus). The relative extent of fluorescent extravasation and BBB disruption was then calculated by multiplying the area with the fluorescent intensity.

BBB Permeability.

Mice injected with BSA, RGMc, RGMa, or RGMa+RGMc. Widefield imaging was then carried out under an Olympus microscope (BX6 1WI) prior to and following the i.v. injection of Texas red dye (100 µL, 5 mg/ml); images were captured using 100-300 ms exposure. Leakage of Texas red dye was quantified by a blind experimenter measuring the number of leakage sites/$mm^2$. Recording was performed from 0 min to 35 min post-injection.

Adoptive Transfer.

EAE was passively induced in 6-8 week old C57Bl/6 mice were subsequently treated every 3 days with either RGMc or Vehicle (PBS) until sacrifice. Briefly, donor animals were immunized with 100 ug MOG(35-55) and sacrificed at day 10. Splenocytes were harvested and re-stimulated for 3 days with 33 ug/mL MOG(35-55) in the presence of 20 ng/ml rmIL-23. Cells were then labelled with CellVue Maroon and injected into recipient animals treated with RGMc or vehicle as well as PTx on day 0 and day 2. Recipient animals were treated every 3 days and sacrificed on day 8 and spinal cords sectioned for immunofluorescence staining.

Statistical Analyses.

Data were analyzed using GraphPad Prism software. Student's t-tests and two-way ANOVA were used for direct comparisons between two groups. For comparisons between multiple groups, one-way ANOVA with Bonferroni post-hoc correction for multiple comparisons was utilized. Significance was set at $p<0.05$ (*); $p<0.01$ (); $p<0.001$ (*). Data are presented as mean and SEM.

Example 2

RGMc is Downregulated in EAE

Figures 3A, 3B:
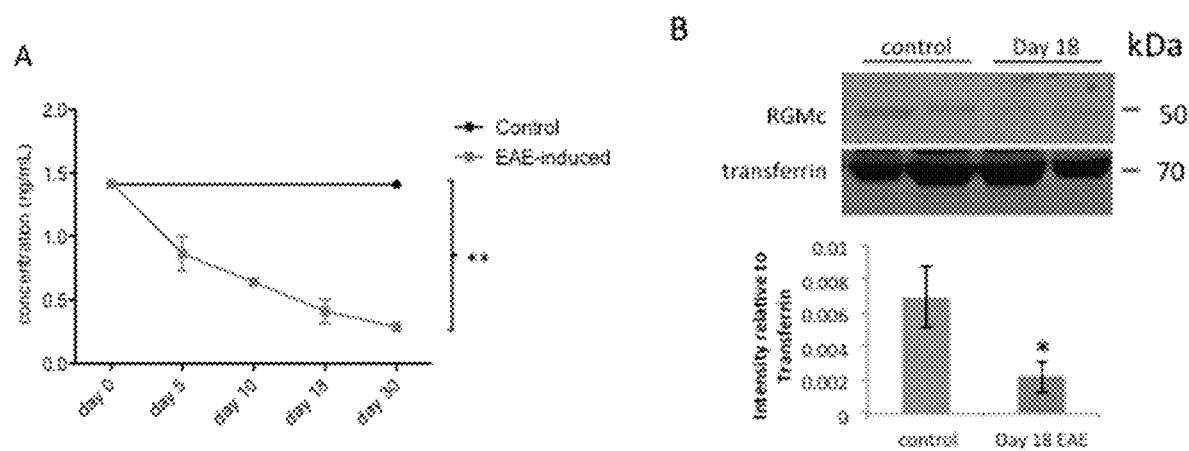

To determine if levels of RGMc were affected by EAE, serum collected from the saphenous vein of 3 EAE-induced mice at days 0, 5, 10, 18, and 30 post-induction were analyzed for RGMc using a commercially available RGMc ELISA kit and compared to control. Compared to control animals, RGMc levels were significantly reduced by day 5 post-induction and remained decreased for the duration of the disease course, reaching a 4-fold decrease at 30 days post induction (FIG. 3A). This finding was confirmed by Western blot analysis (FIG. 3B). Thus, a significant relationship was demonstrated between early development of EAE and reduced levels of circulating RGMc in EAE animals.

Example 3

RGMc Over-Expression Ameliorates the Clinical Severity of EAE-Induced Mice

Figures 4A, 4B, 4C, 4D, 4E, 4F:
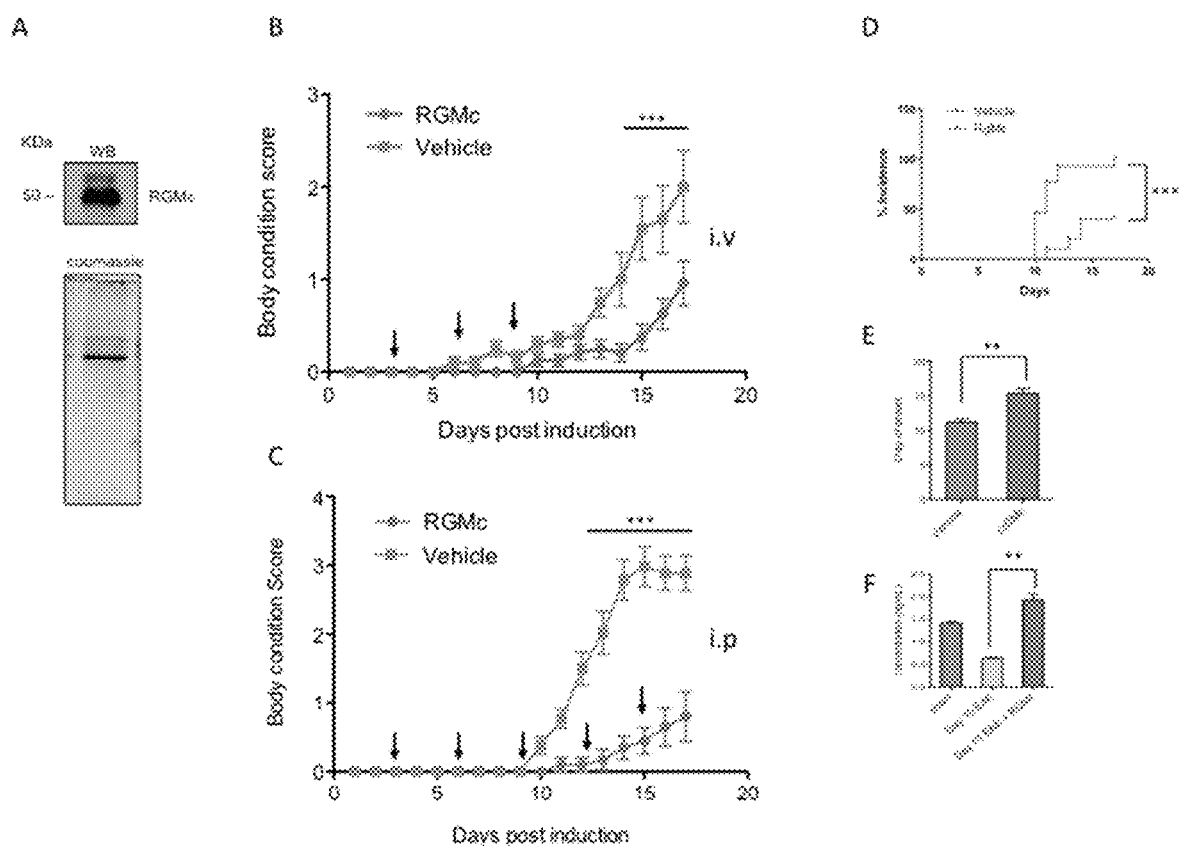

The observation that RGMc protein levels were significantly reduced following induction of EAE led us to further investigate its role in the EAE model. Mice induced with EAE were treated with intravenous injections of sRGMc at days 3, 6, and 9 post-induction. The sRGMc construct was generated as described in Materials and Methods; FIG. 4A shows that sRGMc has a predicted molecular weight of ~50 KDa in non-reducing conditions.

To ensure that over-expression of sRGMc was efficient, sera from 3 RGMc-treated mice were collected and compared to 3 vehicle-treated mice at 24 h post-treatment by ELISA. Mice treated with sRGMc showed a 3-fold increase in sRGMc levels compared to vehicle-treated animals. The mice were then observed and scored twice daily at 12 h intervals for 18 days. RGMc treatment resulted in a significant decrease in clinical severity of the disease (FIG. 4B), but these animals developed clinical symptoms by day 14 post-induction. Whether intra-peritoneal (i.p) injections of RGMc could overcome the transient effects observed with intravenous administration of this protein was explored. Indeed, ip injections of RGMc significantly abrogated disease severity, decreased the incidence of EAE onset (FIG. 4C), and delayed the onset of disease (FIG. 4D). Next the levels of RGMc in the sera of sham-treated animals and mice induced with EAE at day 10 as well as in EAE animals (day 10) that were injected with RGMc were analyzed. As shown in FIG. 4E, compared to sham-treated animals, RGMc levels were significantly reduced in EAE mice, which were restored with RGMc injection. Thus, EAE reduced RGMc levels and over-expression of sRGMc in EAE-induced mice is beneficial in reducing the incidence and the severity as well as delaying the onset of disease.

Figures 5A, 5B, 5C:
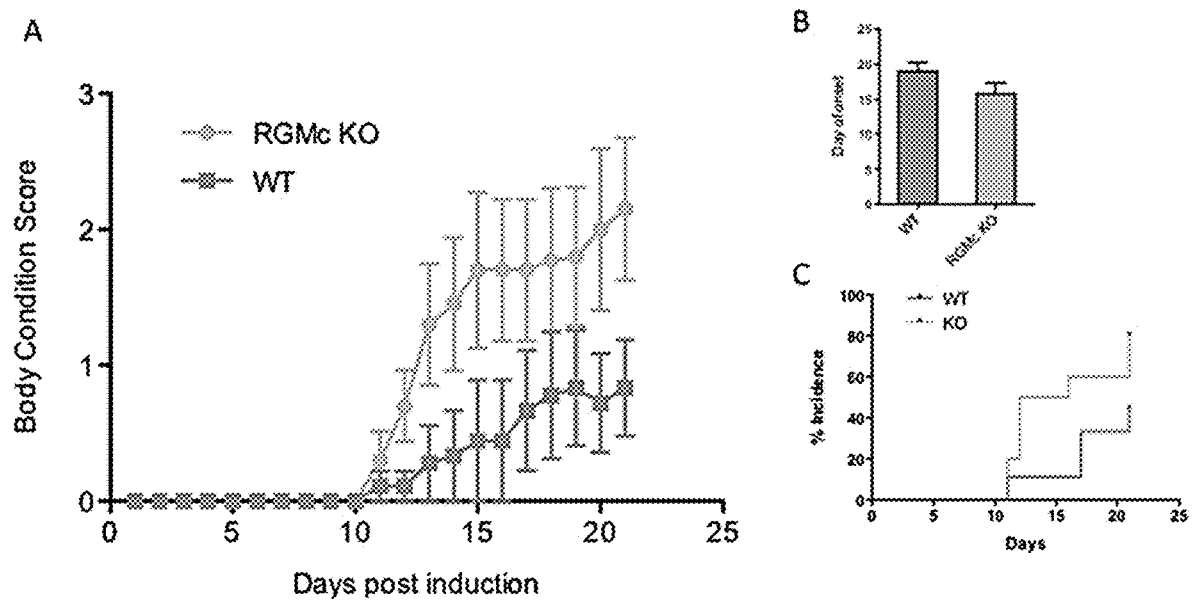

To assess the role of RGMc in the development of EAE, EAE was induced 6-9 week old female mice with a selective homozygous deletion of RGMc (129S-Hfe2$^{tm1Nca}$/J). These mice recapitulate symptoms of JH, with early onset iron overload as well as low hepcidin levels. Deletion of RGMc was associated with a trend (p=0.06) towards an increase in disease severity as well as percentage of incidence (FIG. 5). Thus, evidencing that genetic neutralization of RGMc can result in an exacerbated disease phenotype marked by an increased paralysis and a higher incidence of the disease.

Example 4 sRGMa is Upregulated in EAE and is Crucial in the Development of the Disease.

Figure 6:
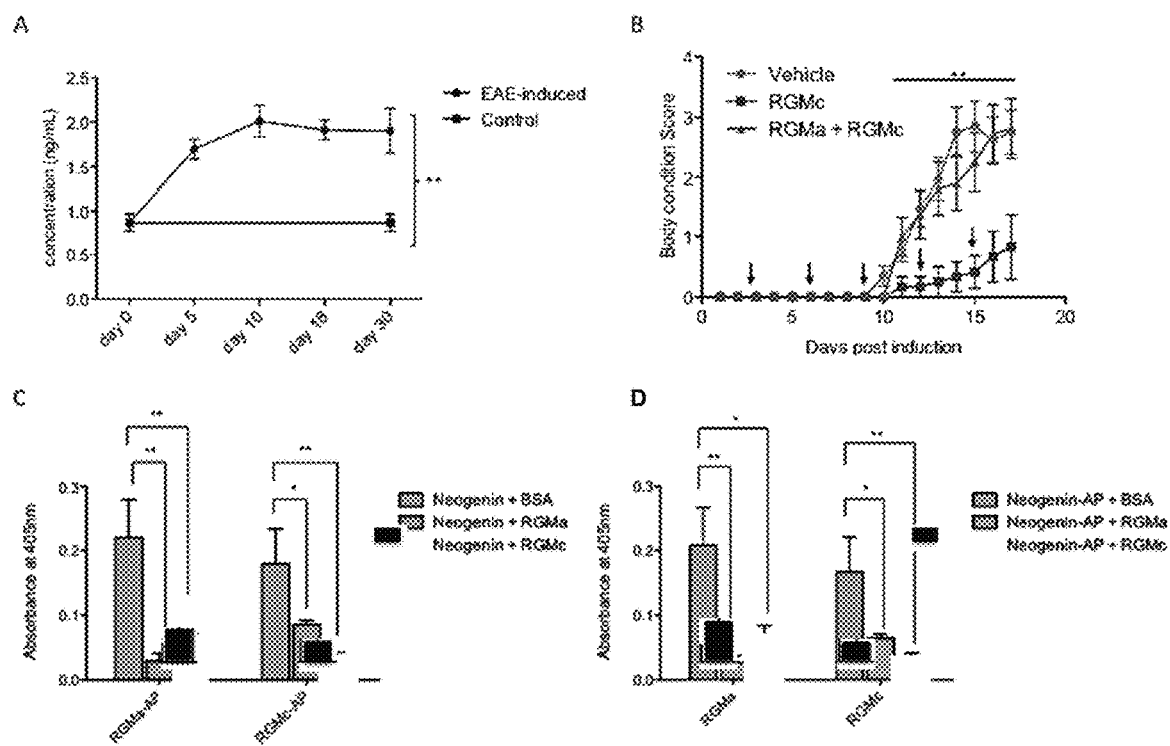

Following the onset of EAE, membrane-bound RGMa is up-regulated on the surface of immune cells, which increased their activation and subsequent extravasation to the CNS. [Muramatsu, R., Kubo, T., Mori, M., Nakamura, Y., Fujita, Y., Akutsu, T., Okuno, T., Taniguchi, J., Kumanogoh, A., Yoshida, M., et al. (2011). RGMa modulates T cell responses and is involved in autoimmune encephalomyelitis. Nat. Med. 17, 488-494; Konig K, et al. (2012) The axonal guidance receptor neogenin promotes acute inflammation. *PloS one* 7(3):e32145] RGMa has been shown to undergo complex post-translational processing resulting in many biologically active soluble fragments. [Tassew N G, Charish J, Seidah N G, & Monnier P P (2012) SKI-1 and Furin generate multiple RGMa fragments that regulate axonal growth. *Developmental Cell* 22(2):391-402] Thus, the levels of RGMa in the sera of mice induced with EAE at days 5, 10, 18 and 30 post-EAE induction were analyzed. A dramatic increase (5-fold) in the levels of RGMa in the sera of EAE-induced mice was observed, which remained elevated for the entire duration of the disease (FIG. 6A). Thus, both sRGMa and sRGMc (FIG. 5F) are both present in mouse sera and possess contrasting expression levels in EAE-induced mice.

To further analyze the role of sRGMc and sRGMa physiologically, whether the interaction of these proteins in mouse sera were crucial in the development of EAE was tested. Mice induced with EAE were treated with either PBS (vehicle), sRGMc or with sRGMc in conjunction with sRGMa. As shown in FIG. 6B, clinical severity was markedly reduced in sRGMc-treated animals compared to control. Simultaneous treatment of animals with sRGMc with RGMa abolished the beneficial effects of RGMc (FIG. 6B) suggesting that RGMc and RGMa have contrasting effects on the clinical severity of EAE.

The possibility that RGMa and RGMc could interfere with each other's signaling by competing with binding to Neogenin was investigated. Pre-incubation of sRGMa with Ec-Neogenin-AP resulted in a 3-fold reduction binding intensity of RGMc to Neogenin when compared to BSA control (FIG. 6C). The reversal experiment (FIG. 6D) showed a similar abrogation of binding intensity to Neogenin. Overall, these results suggest that sRGMa is able to interfere with sRGMc by interacting on non-overlapping binding sites in Neogenin and vice-versa. Thus, the present inventors have shown for the first time that two molecules from the same protein family are able to compete and regulate each other's binding to their receptor and, furthermore, that sRGMa is critical in the development of EAE.

Example 5 sRGMc has No Impact on Naïve Immune Cells.

Figure 7:
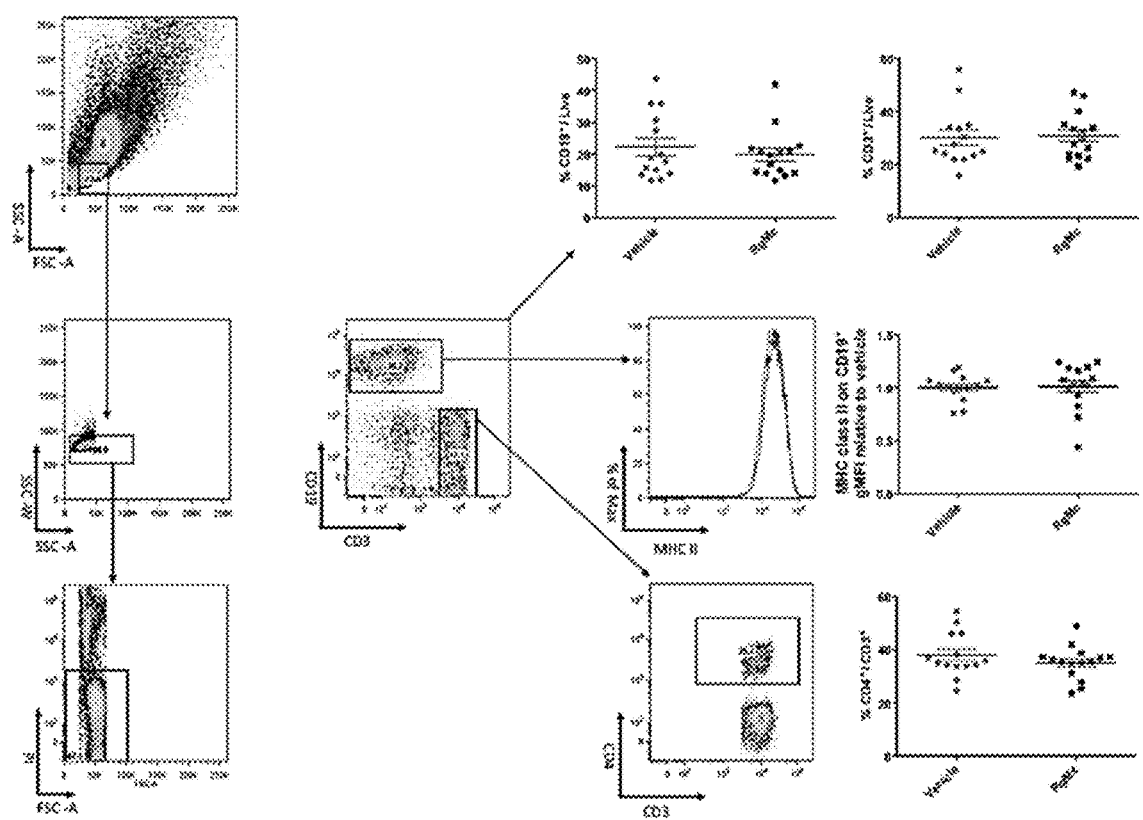
FIG. 7—FIG. 7 shows sRGMc treatment has no effect on naïve immune cell populations. Mice induced with EAE were sacrificed at 10 days post-induction and splenocytes were harvested and stained as described in the Examples. No difference was observed in the percentage of B cells, T cells, or MHC II on B cells in RGMc-treated versus vehicle-treated animals (n=15)
Figures 8A, 8B, 8C, 8D:
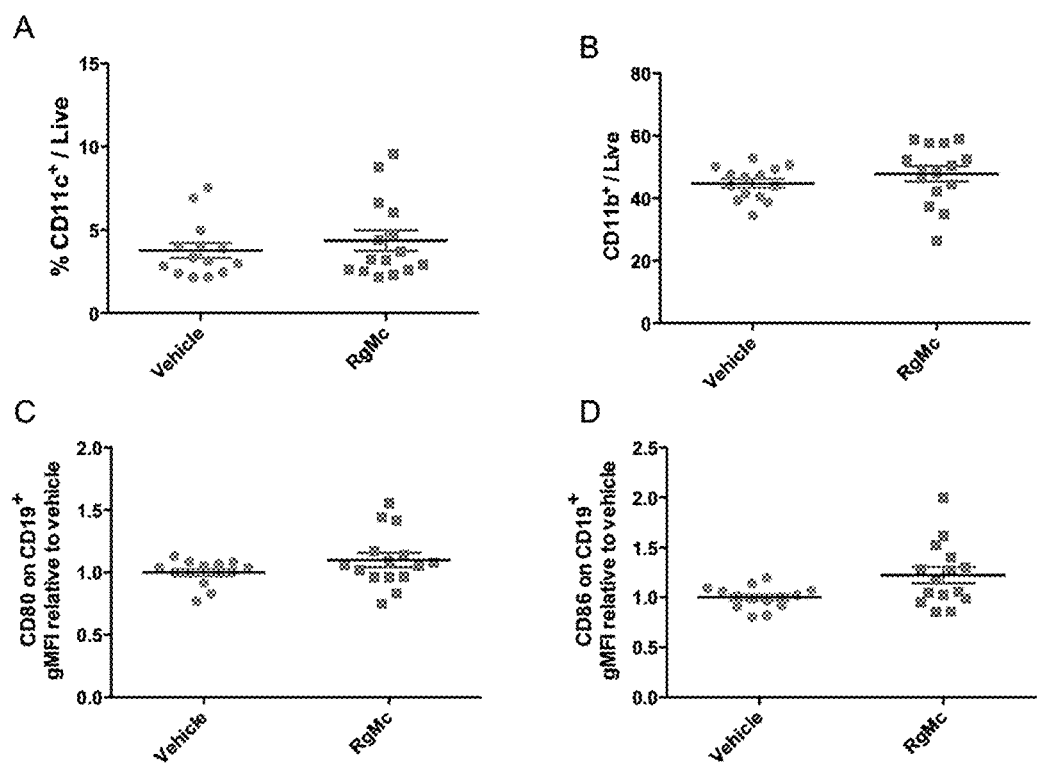
Figures 9A, 9B, 9C:
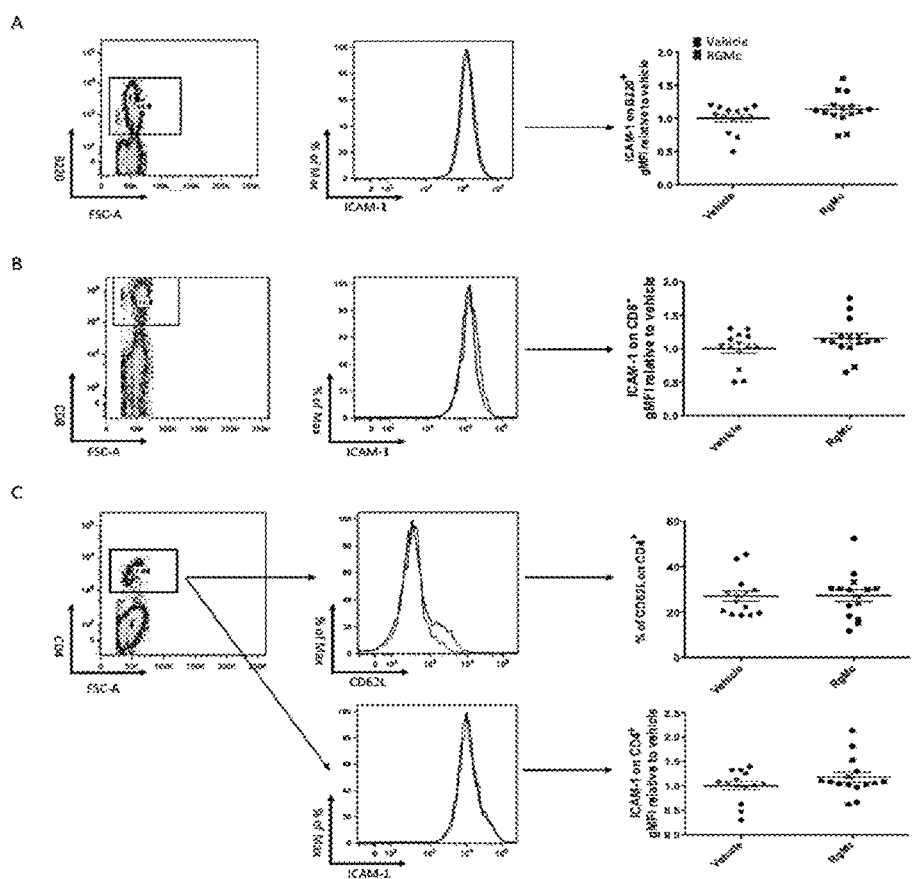

Recent reports show that the RGMa-Neogenin signaling pathway is able to modulate T cell priming and promote their activation by up-regulating small GTPases such as Rap1. Activation of Rap1 increases the adhesion profile of T cells as well as their infiltration within the CNS. [Muramatsu, R., Kubo, T., Mori, M., Nakamura, Y., Fujita, Y., Akutsu, T., Okuno, T., Taniguchi, J., Kumanogoh, A., Yoshida, M., et al. (2011). RGMa modulates T cell responses and is involved in autoimmune encephalomyelitis. *Nat. Med.* 17, 488-494] Results showing that sRGMc interferes with the interaction between sRGMa and Neogenin in vitro prompted investigation of its role in modulating the immune system. To assess whether sRGMc alters the priming of immune cells, both the distribution and activation of naïve immune cells of EAE-induced mice was analyzed. Splenocytes from day 10 RGMc-treated mice were analyzed by flow cytometry and compared to the vehicle-treated group. As shown in FIGS. 7 and 8, sRGMc treatment in EAE animals does not alter the distribution of effector cells ($CD3^+$, $CD8^+$, and $CD4^+$ T cells). Moreover, both the distributions and activation of dendritic cells (CD11c+) and B cells (MHC II, $CD80^+/CD86^+$) were also unaltered. The infiltration of leukocytes into the CNS is a key stage in the acute phase of EAE. As a result, whether sRGMc could alter the ability of T cells to migrate into the CNS was investigated. In order to migrate into the parenchyma, immune cells must overexpress a variety of cellular adhesion proteins. Here, the expression of adhesion markers (ICAM-1 and CD62L) in both naive splenocytes and lymph node cells was analyzed. As depicted in FIG. 9, sRGMc treatment in EAE animals does not affect the expression of adhesion markers on the surface of $CD4^+$ and $CD8^+$ T cells as well as B cells.

Figures 10A, 10B:
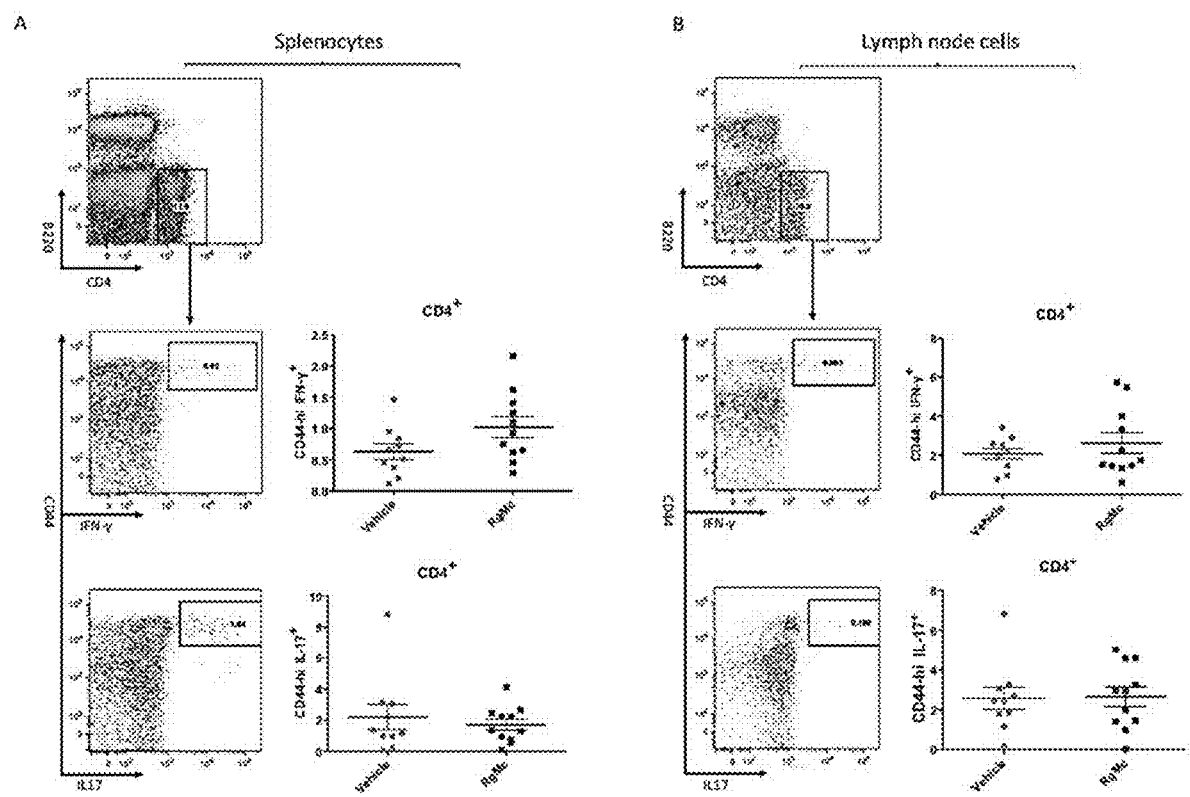
Figures 11A, 11B:
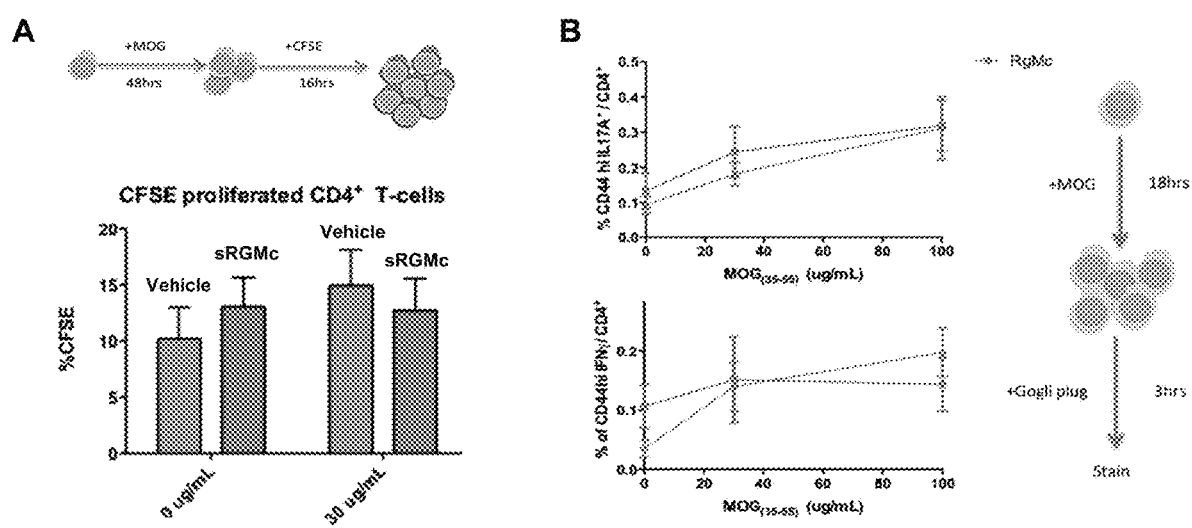
Figure 12:
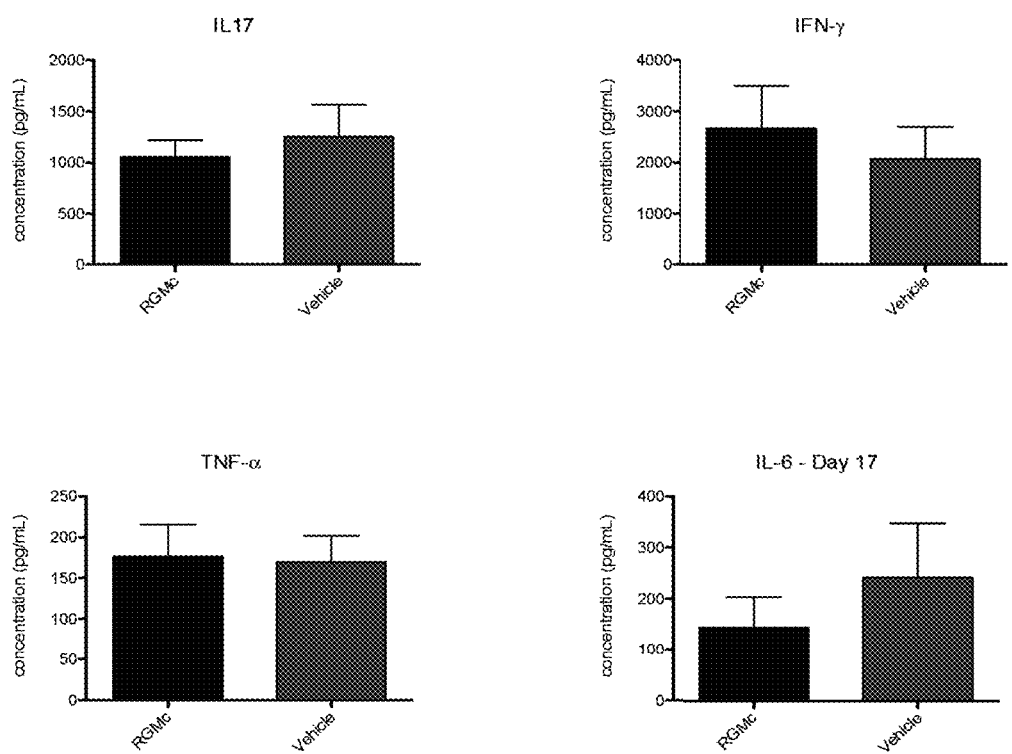
FIG. 12—FIG. 12 shows sRGMc treatment does not alter the cytokine secretion of MOG-pulsed splenocytes. Concentrations of IL17, IFN-γ, TNFα, and IL6 measured in splenocytes harvested from EAE-induced mice treated with either PBS (Vehicle) or RGMc and pulsed with MOG for 96 h. Cytokine secretion was analyzed using an ELISA as described in the Examples. Data are means±SEM (n=15 animals per group).

Expression of RGMa on the surface of bone marrow-derived dendritic cells was previously shown to prime and activate $CD4^+$ T cells through its interaction with Neogenin and treatment with a polyclonal RGMa-antibody reduced this activation demonstrated by reduced secretion of IL-17 and IFN-γ. [Muramatsu, R., Kubo, T., Mori, M., Nakamura, Y., Fujita, Y., Akutsu, T., Okuno, T., Taniguchi, J., Kumanogoh, A., Yoshida, M., et al. (2011). RGMa modulates T cell responses and is involved in autoimmune encephalomyelitis. *Nat. Med.* 17, 488-494] Here, the present inventors showed that sRGMc interferes with RGMa for its binding to Neogenin (FIG. 6C). Consequently, whether treating EAE mice with sRGMc could alter the activation profile of immune cells was explored. sRGMc was shown to have no effect on the expression profile of IL-17 and IFN-γ secreted by $CD4^+$ T cells in EAE mice (FIG. 10). In the EAE model used, $CD4^+$ T cells are specifically primed towards $MOG_{(35-55)}$ peptide. Since the activation profile of immune cells is dependent on their antigen recognition, whether presenting sRGMc-treated immune cells with $MOG_{(35-55)}$ peptide would modulate the activation potential splenocytes when compared to controls was tested. C57/BL6 mice were immunized with $MOG_{(35-55)}$, followed by treatment with either sRGMc or vehicle and harvested splenocytes 10 days post induction. Splenocytes were then re-stimulated with $MOG_{(35-55)}$ peptide for 18 hrs and analyzed their cytokine profile. Again, no apparent effect was seen in RGMc-treated mice when compared to control mice (FIG. 11). These findings were confirmed using an ELISA on media collected from splenocytes pulsed with MOG(35-55) for 3 days (FIG. 12).

Example 6 sRGMc Alters Leukocyte Infiltration into the CNS

Figures 13A, 13B, 13C:
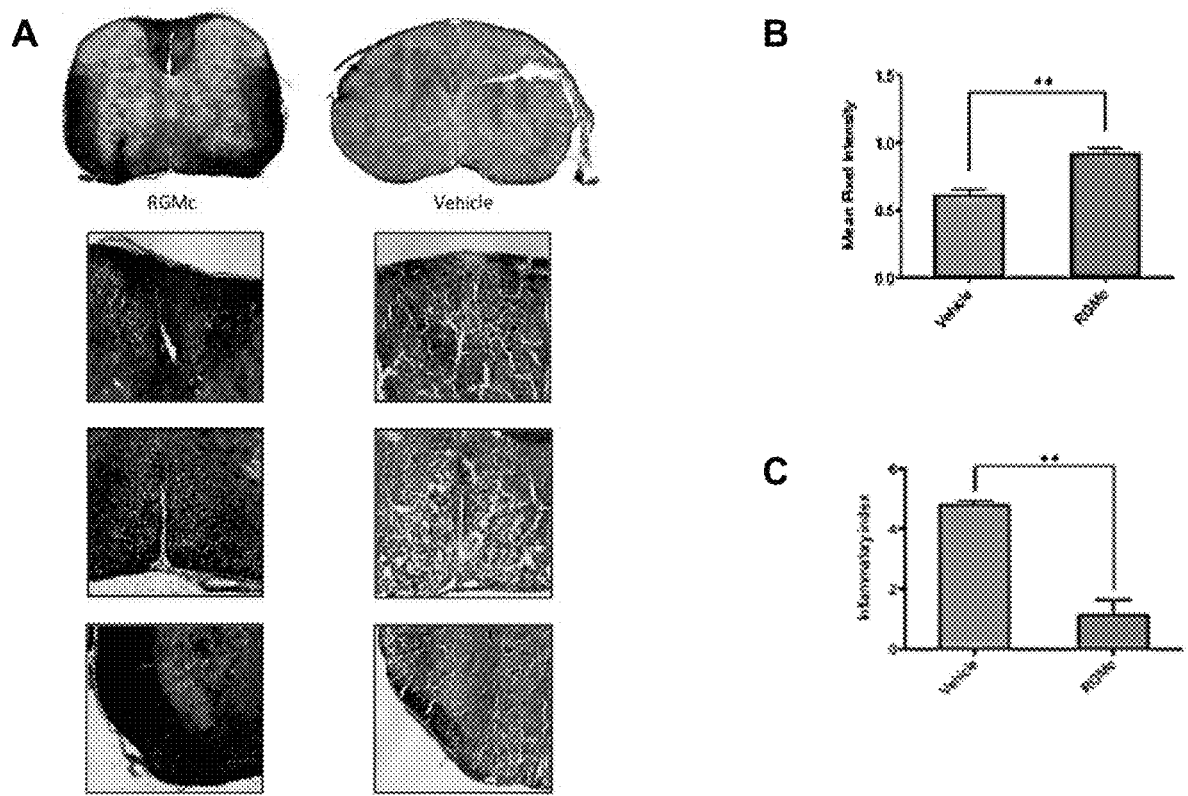

EAE is characterized by broad infiltration of immune cells within the CNS followed by de-myelination, both of which contribute to the clinical severity of the disease. [Gold R, Linington C, & Lassmann H (2006) Understanding pathogenesis and therapy of multiple sclerosis via animal models: 70 years of merits and culprits in experimental autoimmune encephalomyelitis research. *Brain: a Journal of Neurology* 129(Pt 8):1953-1971] Therefore whether sRGMc treatment alters leukocyte presence within the CNS of EAE-induced mice was explored. The histological and inflammatory profiles of cervical spinal cord sections isolated from vehicle- and RGMc-treated EAE animals were assessed. Strikingly, both the extent of cellular infiltrates and de-myelination of sRGMc-treated animals were significantly reduced when compared to vehicle-treated animals (FIGS. 13A and B). Furthermore, the inflammatory index score was significantly lower in RGMc-treated animals (FIG. 13C).

To further characterize the profile of cellular infiltrates within the spinal cords of EAE-induced mice treated with RGMc, spinal cords were stained for CD3 (pan T cell marker), B220 (pan B cell marker) and CD11b (pan myeloid cell marker). In order to analyze the extravasation pattern of each cell type within the spinal cord of EAE-induced mice, spinal cords were divided into 7 patterns of infiltration (data not shown). As shown in FIG. 14, infiltration of $CD3^+$, $B220^+$, and $Cd11b^+$ cells into cervical spinal cords harvested from EAE animals that received sRGMc treatment was significantly reduced, suggesting that sRGMc treatment lessens the extent of leukocyte infiltration into the CNS in EAE-induced mice. Furthermore, sRGMc treatment is associated with a preserved myelination profile in contrast to vehicle-treated animals.

Example 7 sRGMc Reduces BBB Permeability in Endothelial Cells.

Figures 15A, 15B, 15C, 15D:
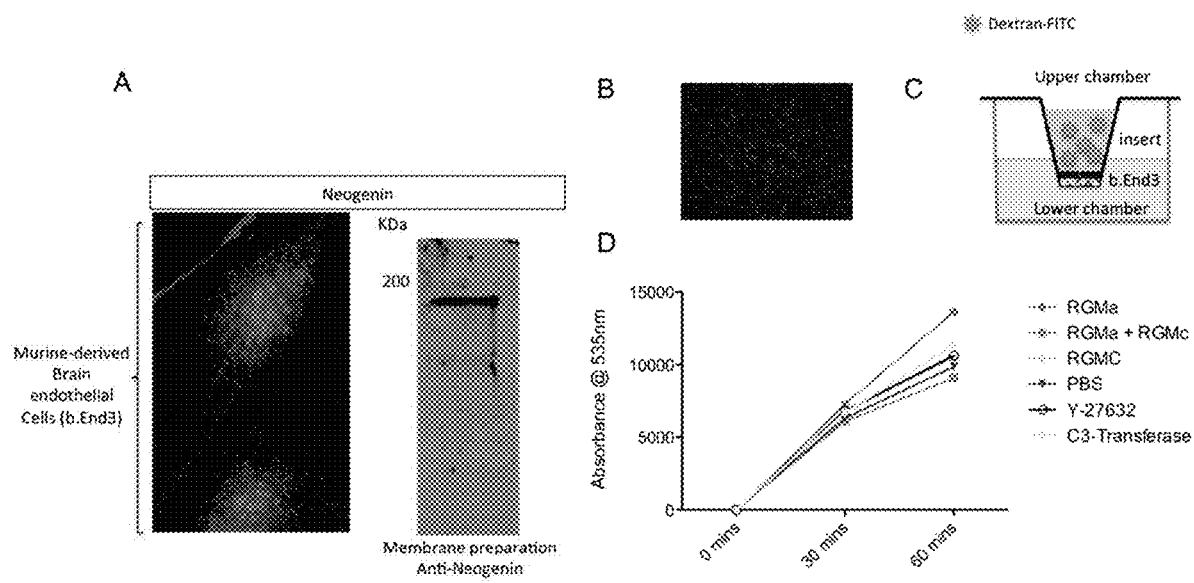

RGMa signaling is dependent on its interaction with Neogenin by activating downstream cytoskeletal remodeling proteins, such as RhoA. [Conrad S, Genth H, Hofmann F, Just I, & Skutella T (2007) Neogenin-RGMa signaling at the growth cone is bone morphogenetic protein-independent and involves RhoA, ROCK, and PKC. *The Journal of Biological Chemistry* 282(22):16423-16433]. Notably, RhoA signaling has extensively been shown to modulate the integrity of the blood-brain EC barrier. The BBB synchronizes the homeostasis of the CNS, regulating the passage of leukocytes into the parenchyma. Moreover, BBB disruption is a key feature in both EAE and MS, which leads to the subsequent infiltration of immune cells within the CNS. [Persidsky Y, et al. (2006) Rho-mediated regulation of tight junctions during monocyte migration across the blood-brain barrier in HIV-1 encephalitis (HIVE). *Blood* 107(12):4770-4780] Moreover, the BBB could represent a site for therapeutic target in CNS diseases. Based on observations that sRGMc interferes with sRGMa binding to Neogenin and that sRGMc treatment curtails leukocyte infiltration into the CNS in EAE-induced mice, the possibility sRGMc could restore BBB integrity by interfering with sRGMa actions was tested. To test this theory, a murine brain-derived cell line (b.end3) was obtained to replicate an in vitro model of the blood-brain EC barrier. Using both immunohistochemistry and western blot analysis of b.end3 cells, it was shown that Neogenin is strongly expressed on the surface of these cells, as shown in FIG. 15A. Next the role of sRGMa on BBB permeability was assessed using a 4-KDa Dextran conjugated to a FITC fluorochrome (Dextran-FITC). b.end3 cells were allowed to form a monolayer on Boyden chambers (FIGS. 14B and C) and were subsequently treated with sRGMa, sRGMa blocking peptides for 4 h and extravasation of Dextran-FITC was assessed. Treatment of sRGMa increased the extravasation of Dextran-FITC when compared to vehicle-treated wells. Treatment with either C3 Transferase (Rho inhibitor) or Y27632 (Rho Kinase inhibitor) reduced the extravasation of Dextran-FITC (FIG. 15D). Because sRGMc reproduced the RhoA/RhoK inhibitor effect, the present inventors concluded that sRGMc by blocking RGMa-mediated Rho/RhoK activation diminishes blood-brain EC barrier permeability, thus preventing infiltration of leukocytes in the CNS.

To confirm the role of sRGMc in maintaining blood-brain EC barrier integrity in vivo, whether Neogenin was expressed in endothelial cells lining the BBB of mice was first examined. A sham mouse spinal cord was stained with anti-CD31 to localize the presence of endothelial cells, DAPI to localize the nuclei of cell, as well as Neogenin. As shown in FIG. 16, Neogenin is widely expressed in the spinal cord and co-localizes with CD31 staining confirming that Neogenin is expressed on the surface of endothelial cells in the mouse spinal cord. Next, the present inventors explored if sRGMc treatment alters the integrity of the BBB following the induction of EAE. Spinal cords isolated from RGMc- or vehicle-treated mice were stained with three markers: 1) Fibrinogen: a small plasma protein unable to cross the BBB under normal conditions 2) CD31 and 3) DAPI. In sharp contrast to EAE animals treated with vehicle, animals treated with sRGMc showed a significant decrease in fibrinogen extravasation (FIGS. 17A and B) indicative of a preserved BBB integrity.

Example 8

RGMc Protects BBB Integrity

Next, the BBB permeability was assessed by injecting mice with BSA, RGMa, RGMa plus RGMc and subsequently followed by assessment of Texas dye leakage using widefield imaging as an indication of BBB integrity. RGMa significantly disrupted BBB integrity, which was suppressed by the RGMc addition (FIG. 18). Having shown that Neogenin is expressed by endothelial cells in human and murine tissues and because RGMa/c regulate BBB integrity, the present inventors considered whether RGMc regulates Claudin 5 levels, which is a tight junction protein critical for BBB maintenance. Thus, Claudin 5 expression following RGMa/c treatments of murine-derived brain endothelial cells (b.End3) was studied. B.En3 cells were grown up to 80% confluency and were treated with overnight incubation with RGM proteins. Incubation with RGMc did affect Claudin5 levels, but RGMa led to a 2-fold reduction in Claudin 5 levels in these cells (FIG. 19). Strikingly, when RGMa and RGMc were added concurrently to cells, Claudin 5 levels were similar to PBS Controls. Thus, RGMa induced down-regulation of Claudin 5 can be prevented by RGMc (FIG. 19). These data evidence a mechanism by which RGMa and RGMc compete for binding to Neogenin, thereby regulating Claudin5 levels and BBB integrity.

Example 9

RGMc Regulation of Cellular Infiltration

Having shown that RGMc levels regulate the extravasation of molecules through the BBB, its role on cellular infiltration was evaluated. To do so, adaptive transfer using spleenocyte cells from MOG treated animals was performed. After collection of splenocyte cells were re-stimulated for 3 days with MOG, stained with Cellvue Maroon and injected into recipient mice treated with pertussis toxin. Following injection, animals received either PBS (Control) or RGMc every 3 days. Eight days after transfer animals were sacrificed and cellular infiltration was monitored using Cellvue-reporter. Examination of spinal cord sections of PBS animals revealed an accumulation of fluorescent (Cellvue+) infiltrates that co-localized with T cell marker CD4 (FIG. 20). This was in contrast with RGMc treated animals that did not show accumulation of Cellvue+ cells within the cord. Thus, treatment with RGMc prevented T cell infiltration towards the CNS.

Example 10

Effects of RGMc, RGMa and Immunoglobulin Domain in Neogenin (4Ig) on BBB

The effects of RGMc, RGMa and the immunoglobulin domain in Neogenin (4Ig peptide) in modulating BBB integrity was explored by assessing Texas red dye leakage. To further assess the role of RGMc in modifying BBB integrity, Texas dye leakage was also assessed in RGMc knockout (KO) mice. As observed in vitro, RGMa injection into mice disrupted BBB integrity with significantly elevated leakage of Texas Red dye, which was ameliorated by RGMc or by blocking RGMa binding with Neognin (4Ig) (FIG. 21). Furthermore, similar experiments conducted in RGMc knockout mice showed significantly less Texas Red dye leakage compared to wild type animals (FIG. 21). Collectively, our data show that elevated RGMa disrupts BBB integrity, which can be restored by either RGMc or by blocking the interaction of RGMa with its receptor, Neogenin.

Example 11

Effects of sRGMc on Remyelination in Cerebellar Organotypic Cultures

To assess the ability of sRGMc to function as a remyelinating agent, its function in in vitro cerebellar explant cultures was investigated. Briefly, cultures were demyelinated using lysolecithin, a detergent, and then cultured in the presence of sRGMc for 14 days.

Myelination-demyelination-remyelination studies were performed in mouse cerebellar organotypic cultures. The cerebella of postnatal 6 day old pups were dissected and sectioned at 400 µm thickness using vibratome. Cerebellar sections were then plated on insert plates (Corning, Wilkes Barre, Pa.) and allowed to attach. Media was replaced every 2-3 days and cultures were maintained for 7 days. To induce demyelination, 0.5 mg/ml lysolecithin (1'-monoacyl-1-3-glycerylphosphorylcholine; Sigma) was added to the culture medium for 18 hr, after which it was removed and replaced with fresh medium containing sRGMc (500 ng/ml) or control protein and the cultures maintained for 14 more days. Media was replaced every 2-3 days. Demyelination-remyelination was assessed by staining explants with myelin basic protein antibody MBP (Cell Signaling).

Treatment with sRGMc (FIG. 22) was able to promote remyelination as assessed by staining with myelin basic protein. This finding evidences that sRGMc can be of therapeutic value in diseases impacted by loss of myelin, including primary progressive multiple sclerosis.

Example 12

Effects of sRGMc on Nerve Regeneration in an Optic Nerve Crush and Regeneration Model Optic nerve crush experiments were performed on animals and recovery assessed by staining for axonal fibres. The optic nerves of adult mice were crushed using fine self-closing forceps. sRGMc (1 µg/ml) or control solution was injected intraocularly at 3 and 10 days after injury. Animals were sacrificed at day 21 and optic nerves were dissected and fixed in 4% PFA. The optic nerves were sectioned longitudinally at 14 microns and stained with GAP43 antibody to stain newly regenerating axons. The data showed that treatment with sRGMc, and not control proteins, could promote the regeneration of axonal fibres at the site of injury, as was revealed upon staining with GAP43 (FIG. 23).

Example 13

Effects of RGMc in Stroke, as Modeled in a Middle Cerebral Artery Occlusion (MCAO) Model The possibility that RGMc may also restore BBB integrity following stroke was also tested. Middle Cerebral Artery Occlusion (MCAO) was performed in rats, which were treated with a daily tail vein injection of 70 µg of RGMc or PBS (control). Seven days following MCAO, animals received injection of Evans blue to monitor BBB integrity (FIG. 24). To measure BBB integrity, the amount of Evans Blue Dye/g of brain tissue was measured. Animals that received RGMc showed a 3-fold reduction in Evans Blue levels in the brain compared to PBS-treated animals. Upon visual inspection of the extent of Evans Blue dye for both sets of brains, it was seen that RGMc treatment strongly reduced Evans Blue extravasation into the CNS as compared to control (FIG. 24, A). This effect was also quantitated: brains were homogenized and the amount of Evans Blue quantified per gram of wet brain (FIG. 24, B). These data are congruent with those from the EAE models, thus supporting our hypothesis that RGMc can prevent BBB disruption in CNS injured animals.

In a separate experiment, whether RGMc treatment, which prevents BBB disruption following stroke, could lead to functional recovery (FIG. 25) was studied. Rats were subjected to MCAO and treated with either tail-vein injection of 70 µg of RGMc or control (PBS). Blinded behavioral assessment of neurological deficit (Bederson test) was performed over a 7 day period, the results of which showed that treatment with RGMc led to a significant (*p<0.05) improvement of functional scores when compared to control. Our data suggest that RGMc, by preventing loss of BBB integrity and function, leads to restoration of neurological function following stroke.

What is claimed is:

1. A method of decreasing the permeability of the blood brain barrier in a subject comprising administering to the subject a therapeutically effective amount of an agent comprising four immunoglobulin domains of Neogenin (4Ig).

2. The method of claim 1 in which the agent comprises residues 1-417 of GenBank accession AAI43272.

3. The method of claim 1 in which the agent has at least about 80% similarity to the amino acid sequence comprising amino acids 1 to 383 of Accession No. AAC59662.

4. The method of claim 1 for treating a disease or condition associated with disruption of the blood brain barrier.

5. The method of claim 4 in which the disease is multiple sclerosis (MS), ischemia (stroke), spinal cord injury, Alzheimer's disease, Parkinson's disease, brain cancer, epilepsy, depression, or an ocular condition, including glaucoma or retinitis pigmentosis (RP).

6. The method of claim 5 in which the disease or condition is MS.

7. The method of claim 6 in which the agent promotes re-myelination or prevents de-myelination in the subject.

8. The method of claim 4 in which the subject has primary progressive multiple sclerosis.

9. The method of claim 4 in which the method prevents or reduces immune cell infiltration into the central nervous system (CNS).

10. The method of claim 1 comprising, prior to administration of the agent comprising 4Ig, administering an agent that increases the permeability of the blood brain barrier to a molecule in the bloodstream of the subject.

11. The method of claim 10 in which the agent that increases the permeability of the blood brain barrier is Repulsive Guidance Molecule A (RGMa), soluble RGMa (sRGMa), a functional fragment, variant or mimic thereof or stimulates RGMa.

12. The method of claim 10 wherein the agent comprising 4Ig is administered within 24 hours after administration of the agent that increases the permeability of the blood brain barrier.

13. The method of claim 10 in which the molecule is a pharmaceutical or an imaging agent.

14. The method of claim 13 in which the pharmaceutical or imaging agent is co-administered with or is administered after the agent that increases the permeability of the blood brain barrier.

15. The method of claim 14 in which the pharmaceutical is an anaesthetic, antipsychotic, antidepressant, antiemetic, anticonvulsant, or anti-cancer drug.

16. The method of claim 13 in which the pharmaceutical is for treatment of a disease or condition selected from MS, ischemia (stroke), spinal cord injury, Alzheimer's disease, epilepsy, depression, or an ocular condition, including glaucoma or RP, or a movement disorder, including Parkinson's disease.

17. The method of claim 1 in which the subject is human.

18. The method of claim 1 in which the agent is a tagged peptide.

19. A method of stabilizing or restoring the blood brain barrier in a subject comprising administering to the subject a therapeutically effective amount of an agent comprising an immunoglobulin domain four immunoglobulin domains of Neogenin (4Ig).

* * * * *